US012778818B2

(12) United States Patent
Bewick-Sonntag et al.

(10) Patent No.: US 12,778,818 B2
(45) Date of Patent: Nov. 3, 2026

(54) ABSORBENT ARTICLE FOR FLUID MANAGEMENT

(71) Applicant: The Procter & Gamble Company, Cincinnati, OH (US)

(72) Inventors: Christopher Philip Bewick-Sonntag, Cincinnati, OH (US); Gueltekin Erdem, Cincinnati, OH (US); John David Norcom, Cincinnati, OH (US); Naka Seidel, Frankfurt am Main (DE); Shirdish Poondru, Cincinnati, OH (US); Matthew Howard Wasson, Cincinnati, OH (US); Rong Deng, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 320 days.

(21) Appl. No.: 18/198,306

(22) Filed: May 17, 2023

(65) Prior Publication Data

US 2023/0381036 A1 Nov. 30, 2023

Related U.S. Application Data

(60) Provisional application No. 63/480,335, filed on Jan. 18, 2023, provisional application No. 63/413,636,
(Continued)

(51) Int. Cl.

| | |
|---|---|
| ***A61F 13/539*** | (2006.01) |
| ***A61F 13/15*** | (2006.01) |
| ***A61F 13/53*** | (2006.01) |

(52) U.S. Cl.

CPC ...... *A61F 13/539* (2013.01); *A61F 13/15203* (2013.01); *A61F 2013/15317* (2013.01);
(Continued)

(58) Field of Classification Search

CPC .............. A61F 13/539; A61F 13/15203; A61F 2013/15317; A61F 2013/15357;
(Continued)

(56) References Cited

U.S. PATENT DOCUMENTS

| | | | |
|---|---|---|---|
| 3,494,821 | A | 2/1970 | Evans |
| H163 | H | 11/1986 | Spraker et al. |

(Continued)

FOREIGN PATENT DOCUMENTS

| | | | |
|---|---|---|---|
| CA | 2182570 | C | 8/2000 |
| CA | 2239516 | C | 5/2002 |

(Continued)

OTHER PUBLICATIONS

PCT Search Report and Written Opinion for PCT/US2023/022453 dated Aug. 7, 2023, 13 pages.
(Continued)

*Primary Examiner* — Susan S Su
*Assistant Examiner* — Erin A Kim
(74) *Attorney, Agent, or Firm* — Anna E. Haller; Amanda Herman Berghauer

(57) ABSTRACT

A disposable absorbent article having a topsheet, a backsheet, and an absorbent core structure disposed therebetween. The absorbent core structure includes an upper nonwoven layer comprising polymer fibers, a lower nonwoven layer comprising polymer fibers, and an inner core layer disposed between the upper and lower nonwoven layers. The inner core layer includes from about 50% to about 85% cellulosic fibers, by weight of the inner core layer, and superabsorbent particles. The inner core layer is contained within the nonwoven layers by substantially sealing at least a left side region and a right side region of the upper and lower nonwoven layers. The absorbent article has a CD Dry Bending Stiffness between about 10 to about 30 N·mm$^2$ as
(Continued)

measured according to the Wet and Dry CD and MD 3 Point Bend Method and a Total IFF+SFF value of between about 20 and about 200 mg as measuring according to the Acquisition Time and Rewet Method.

20 Claims, 18 Drawing Sheets

Related U.S. Application Data filed on Oct. 6, 2022, provisional application No. 63/413,634, filed on Oct. 6, 2022, provisional application No. 63/345,582, filed on May 25, 2022.

(52) U.S. Cl.
CPC ............... *A61F 2013/15357* (2013.01); *A61F 2013/15373* (2013.01); *A61F 2013/15406* (2013.01); *A61F 2013/15414* (2013.01); *A61F 2013/530343* (2013.01); *A61F 2013/530489* (2013.01)

(58) Field of Classification Search
CPC .. A61F 2013/15373; A61F 2013/15406; A61F 2013/15414; A61F 2013/530343; A61F 2013/530489; A61F 13/475; A61F 13/537; A61F 13/53
See application file for complete search history.

(56) References Cited

U.S. PATENT DOCUMENTS 4,938,754 A 7/1990 Mesek
5,275,591 A 1/1994 Mavinkurve
5,458,592 A 10/1995 Abuto et al.
5,567,260 A 10/1996 Mcfall
5,591,148 A 1/1997 Mcfall et al.
5,611,790 A 3/1997 Hines et al.
5,756,039 A 5/1998 Mcfall
5,810,800 A 9/1998 Hunter et al.
5,928,452 A 7/1999 Mcfall et al.
D413,669 S 9/1999 Mcfall et al.
5,964,689 A 10/1999 Mcfall et al.
6,045,544 A 4/2000 Hershberger et al.
6,183,587 B1 2/2001 Mcfall et al.
6,203,654 B1 3/2001 Mcfall et al.
6,261,277 B1 7/2001 Osborn, III et al.
6,316,688 B1 11/2001 Hammons
6,432,096 B1 8/2002 Mcfall et al.
6,437,214 B1 8/2002 Everett et al.
6,475,199 B1 11/2002 Gann et al.
6,570,058 B1 5/2003 Fuchs et al.
6,582,411 B1 6/2003 Carstens et al.
6,702,796 B2 3/2004 Mcfall et al.
6,899,701 B2 5/2005 Carstens et al.
7,056,404 B2 6/2006 Mcfall et al.
7,704,241 B2 4/2010 Rosenfeld et al.
8,512,305 B2 8/2013 Dziezok et al.
8,979,815 B2 3/2015 Roe et al.
9,060,904 B2 6/2015 Hundorf et al.
9,259,363 B2 2/2016 Dziezok et al.
9,406,478 B2 8/2016 Birnbach et al.
10,137,039 B2 11/2018 Stelzig et al.
10,772,772 B2 9/2020 Michiels et al.
11,464,385 B2 10/2022 Davis et al.
2001/0014795 A1 8/2001 Kurata et al.
2001/0026861 A1* 10/2001 Takai .................... A61F 13/512 428/167
2001/0031358 A1 10/2001 Tan et al.
2002/0151857 A1* 10/2002 Bast ...................... A61F 13/495 604/378
2003/0040242 A1* 2/2003 Pike ......................... D04H 1/54 442/352
2003/0200991 A1 10/2003 Keck
2005/0080391 A1* 4/2005 Yoshimasa ............ A61F 13/534 604/385.01
2006/0135932 A1 6/2006 Abuto et al.
2007/0044903 A1 3/2007 Wisneski et al.
2007/0087169 A1 4/2007 Mcfall
2007/0224903 A1 9/2007 Chakravarty et al.
2007/0250026 A1* 10/2007 Venturino ......... A61F 13/15634 604/383
2008/0167634 A1 7/2008 Kouta et al.
2009/0131896 A1 5/2009 Ebitsuka et al.
2010/0312206 A1 12/2010 Fujioka
2011/0087185 A1* 4/2011 Wohlke ............... A61F 13/8405 604/367
2011/0089593 A1 4/2011 Miyauchi et al.
2013/0066290 A1 3/2013 Kawakami et al.
2013/0211358 A1 8/2013 Kikkawa et al.
2015/0351976 A1* 12/2015 Viens ................ A61F 13/51121 604/378
2017/0119589 A1 5/2017 Bewick-Sonntag
2018/0001591 A1* 1/2018 Dutkiewicz ............... B32B 5/24
2019/0105424 A1* 4/2019 Saevecke ................ A61L 15/26
2020/0297554 A1 9/2020 Petersen et al.
2020/0315859 A1 10/2020 Denti et al.
2020/0315871 A1 10/2020 Viens et al.
2020/0315873 A1 10/2020 Viens et al.
2020/0323709 A1 10/2020 Sillerström et al.
2021/0292973 A1 9/2021 Rouse et al.
2022/0104973 A1 4/2022 Viens et al.
2022/0168158 A1 6/2022 Miller et al.
2022/0387227 A1 12/2022 Kreisel et al.

FOREIGN PATENT DOCUMENTS

EP 0812171 B1 5/2000
EP 1075244 B1 6/2003
EP 1504741 A1 2/2005
EP 2572687 B1 4/2016
EP 2630939 B1 5/2020
EP 3799848 A1 4/2021
JP 2016112404 A 6/2016
JP 2019034229 A 3/2019
JP 2021062176 A 4/2021
JP 2021083542 A 6/2021
JP 2021097845 A 7/2021
WO 200641507 A1 7/2017
WO 2017115541 A1 7/2017
WO 2017207135 A1 12/2017
WO 2020205946 A1 10/2020

OTHER PUBLICATIONS

All Office Actions; U.S. Appl. No. 18/198,307, filed May 17, 2023.
All Office Actions; U.S. Appl. No. 18/198,303, filed May 17, 2023.
U.S. Appl. No. 18/198,303, filed May 17, 2023, to Christopher Philip Bewick-Sonntag et al.
U.S. Appl. No. 18/198,307, filed May 17, 2023, to Christopher Philip Bewick-Sonntag et al.

* cited by examiner

ABSORBENT ARTICLE FOR FLUID MANAGEMENT

CROSS REFERENCE TO RELATED APPLICATIONS

This application claims the benefit of U.S. Provisional Application No. 63/413,636, filed Oct. 6, 2022, and U.S. Provisional Application No. 63/345,582, filed May 25, 2022, and U.S. Provisional Application No. 63/413,634, filed Oct. 6, 2022, and U.S. Provisional Application No. 63/480,335, filed Jan. 18, 2023, the entire disclosures of which are fully incorporated by reference herein.

FIELD OF THE INVENTION

The present disclosure relates to an absorbent article having conforming features as well as improved resilient structures, yet still provides fluid acquisition and storage properties.

BACKGROUND OF THE INVENTION

Absorbent articles are widely used among consumers, e.g., diapers, training pants, feminine pads, adult incontinence pads, etc. Generally, absorbent articles such as these comprise a topsheet and a backsheet, with an absorbent core structure disposed therebetween. Historically, for menstrual applications, absorbent articles also include a secondary topsheet to serve to drain the topsheet of fluid in order to help keep the body clean and dry. Previous absorbent articles rely on a capillarity gradient structure (where each layer has increasing capillarity, i.e., density) to effectively pull fluid deep into the absorbent core and away from the body. In these structures, capillarity in the secondary topsheet to clean the body is combined with a densified fluid storage core below to effectively drain the secondary topsheet and thereby enable the secondary topsheet to continue to absorb fluid from the topsheet. Other approaches have used lofty, relatively high caliper nonwoven secondary topsheet materials that are highly permeable in combination with a densified fluid storage core below to drain the secondary topsheet of fluid. In this structure, the secondary topsheet provides temporary fluid storage to absorb a large fluid gush and the strong capillarity gradient below helps to efficiently drive fluid towards the fluid storage core.

As noted above, these approaches rely on densification of the absorbent core to increase capillarity and move the fluid away from the body and deep into the core. However, densifying these absorbent systems comes at the cost of comfort (stiffness) and the ability of the absorbent core structure and/or the absorbent article to readily conform to her unique anatomical geometry. Furthermore, the discrete secondary topsheet layer in these approaches is not ideal for complex viscous fluids, like blood, that need to move over the boundary between the layers because inter-layer boundary effects reduce the efficiency of fluid moving between distinct layers.

As such, there is a need for an absorbent article comprising an absorbent core structure that provides good fluid acquisition and storage yet is conformable and wet resilient.

SUMMARY OF THE INVENTION

The present disclosure solves the problem of uncomfortable, nonconformable densified absorbent articles that wet collapse and have discrete secondary topsheet layers by providing an absorbent core structure that sandwiches liquid absorbent material between two resilient nonwoven layers that can not only carry and manage the mechanical stresses in-use and enable the absorbent core structure to recover its shape as the wearer compresses and deforms the absorbent article in-use, but also provides the functionality of a secondary topsheet to pull fluid away from the body. The absorbent core structure of the present disclosure comprises a low density upper nonwoven layer that does not substantially hold fluid (but allows fluid to pass through quickly) and liquid absorbent materials that are capable of absorbing blood quickly.

An absorbent article comprises a topsheet; a backsheet; and an absorbent core structure disposed between the topsheet and backsheet, wherein the absorbent core structure comprises: (a) an upper nonwoven layer comprising polymer fibers and having a basis weight of from about 35 gsm to about 85 gsm; (b) a lower nonwoven layer comprising polymer fibers and having a basis weight of from about 10 gsm to about 40 gsm; and (c) an inner core layer disposed between the upper nonwoven layer and the lower nonwoven layer, wherein the inner core layer comprises from about 50% to about 85% cellulosic fibers, by weight of the inner core layer, and superabsorbent particles; wherein the inner core layer is contained within the nonwoven layers by substantially sealing at least a left side region and a right side region of the upper nonwoven layer and the lower nonwoven layer; wherein the absorbent article has a CD Dry Bending Stiffness between about 10 N·mm2 to about 30 N·mm2 as measured according to the Wet and Dry CD and MD 3 Point Bend Method and a Total IFF+SFF value of between about 20 mg and about 200 mg as measuring according to the Acquisition Time and Rewet Method.

A disposable absorbent article comprises a topsheet; a backsheet; and an absorbent core structure disposed between the topsheet and backsheet, wherein the absorbent core structure comprises: (a) an upper nonwoven layer comprising polymer fibers; (b) a lower nonwoven layer comprising polymer fibers; and (c) an inner core layer disposed between the upper nonwoven layer and the lower nonwoven layer, wherein the inner core layer comprises a mixture of cellulosic fibers and superabsorbent particles; wherein the inner core layer is contained within the nonwoven layers by substantially sealing at least a left side region and a right side region of the upper nonwoven layer and the lower nonwoven layer; wherein the absorbent article has a CD Dry Bending Stiffness between about 10 N·mm2 to about 30 N·mm2 as measured according to the Wet and Dry CD and MD 3 Point Bend Method and a Light Touch Rewet of from 0 to about 0.15 grams as measured according to the Light Touch Rewet Method.

A disposable absorbent article comprises a topsheet; a backsheet; and an absorbent core structure disposed between the topsheet and backsheet, wherein the absorbent core structure comprises: (a) an upper nonwoven layer comprising polymer fibers, wherein the upper nonwoven layer has a Thickness at 7 g/cm2 pressure of from about 0.3 mm to about 1.3 mm as measured according to the Thickness—Pressure Method; (b) a lower nonwoven layer comprising polymer fibers, wherein the lower nonwoven layer has a Thickness at 7 g/cm2 pressure of from about 0.1 mm to about 1.3 mm as measured according to the Thickness—Pressure Method and a basis weight equal to or less than the basis weight of the resilient upper nonwoven layer; and (c) an inner core layer disposed between the upper nonwoven layer and the lower nonwoven layer; wherein the inner core layer comprises from about 125 gsm to about 400 gsm cellulosic fibers; wherein the absorbent core structure has an average density of between about 0.045 g/cm3 and about 0.15 g/cm3; and wherein the upper nonwoven layer has a Wet Penetration Time of less than about 4 seconds as measured according to the Wet Penetration Time Method.

DETAILED DESCRIPTION OF THE INVENTION

Figure 1:
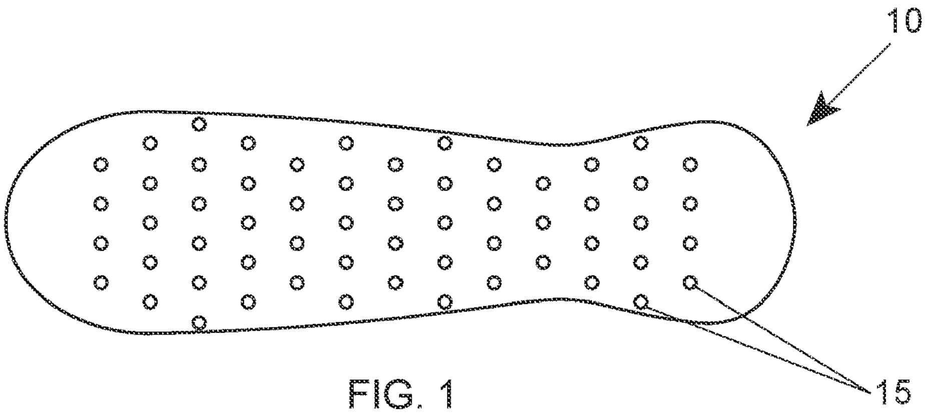
FIG. 1 is a representation of an absorbent core structure in accordance with the present disclosure.

As used herein “disposable absorbent article” or “absorbent article” shall be used in reference to articles such as diapers, training pants, diaper pants, refastenable pants, adult incontinence pads, adult incontinence pants, feminine hygiene pads, cleaning pads, and the like, each of which are intended to be discarded after use.

As used herein “absorbent core structure” shall be used in reference to the upper nonwoven layer, the lower nonwoven layer, and the inner core layer disposed between the upper nonwoven layer and the lower nonwoven layer.

As used herein “hydrophilic” and “hydrophobic” have meanings as well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic, will increase the contact angle of water on the surface of a material while compositions which are hydrophilic will decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

As used herein, “machine direction” refers to the direction in which a web flows through an absorbent article converting process. For the sake of brevity, may be referred to as “MD”. As used herein, “cross machine direction” refers to the direction which is perpendicular to the MD. For the sake of brevity, may be referred to as “CD”.

As used herein, “resilient” refers to a material that tends to retain its shape both in the dry and wet states and when subjected to a compression force tends to recover its original, pre-compression shape when such force is removed. In some aspects, the upper and/or lower nonwoven layers described herein may be resilient.

As used herein, “wearer-facing” (sometimes referred to herein as body-facing) and “outward-facing” (sometimes referred to herein as garment-facing) refer respectively to the relative location of an element or a surface of an element or group of elements. “Wearer-facing” implies the element or surface is nearer to the wearer during wear than some other element or surface. “Outward-facing” implies the element or surface is more remote from the wearer during wear than some other element or surface (i.e., element or surface is proximate to the wearer’s garments that may be worn over the absorbent article).

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The disposable absorbent articles described herein may comprise a topsheet, a backsheet, and an absorbent core structure disposed therebetween. The absorbent core structure may comprise an upper nonwoven layer and lower nonwoven layer, with an inner core layer disposed between the upper nonwoven layer and lower nonwoven layer. The inner core layer may be contained within the nonwoven layers by substantially sealing at least the left side region and right side region of the upper and lower nonwoven layers at a perimeter seal. In some configurations, the upper and lower nonwoven layers may be joined at a perimeter seal which extends around the entire perimeter of the inner core layer.

In some aspects, the disposable absorbent article may comprise the following structure (from a wearer-facing surface to an outward-facing surface): a topsheet, an upper nonwoven layer, an inner core layer, a lower nonwoven layer, and a backsheet. In some aspects, the topsheet may be in direct contact with the upper nonwoven layer, the upper nonwoven layer may be in direct contact with the inner core layer, and/or the inner core layer may be in direct contact with the lower nonwoven layer. By "direct contact", it is meant that there is no further intermediate component layer between the respective layer in direct contact thereto. It is however not excluded that an adhesive material may be disposed between at least a portion of the layers described above.

Figure 3:
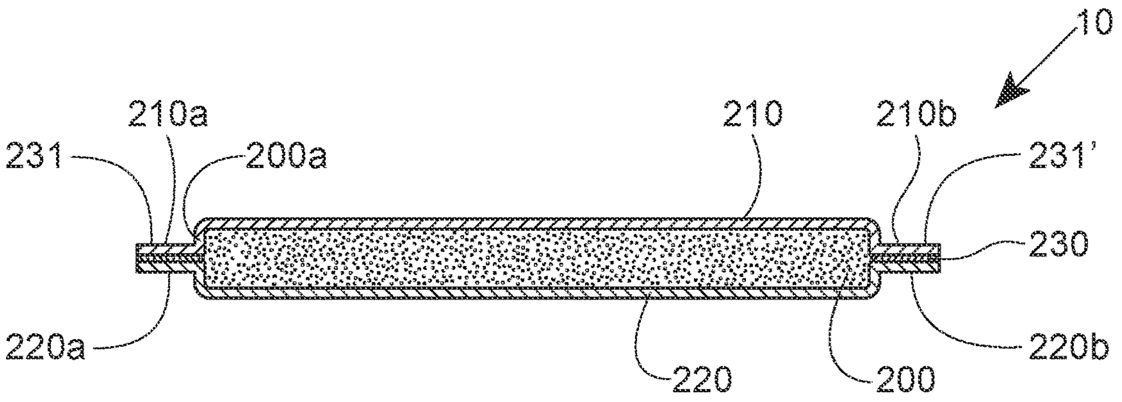
FIG. 3 is a cross section of the absorbent core structure.

As shown in FIGS. 1 and 3, absorbent core structure 10 may comprise an upper nonwoven layer 210 and a lower nonwoven layer 220 (also referred to herein collectively as upper and lower nonwoven layers or upper and lower nonwovens) and an inner core layer 200 disposed between the upper nonwoven layer 210 and the lower nonwoven layer 220. The absorbent core structure 10 may comprise inner core layer 200 comprising a liquid absorbent material. Without being limited by theory, it is believed that the absorbent core structure may recover its shape dry or wet across a range of bodily movements and compressions. The liquid absorbent material may comprise a matrix comprising cellulosic fibers and superabsorbent particles, sometimes referred to herein as "fluff/AGM". The upper and lower nonwoven layers 210, 220 may be joined together at a perimeter seal 230 with glue or other conventional bonding methods including, but not limited to, ultrasonic bonding, fusion bonding, crimping, and combinations thereof.

The flexibility and/or resiliency of the absorbent core structure results in an absorbent article that comfortably conforms to the wearer's anatomical geometry while efficiently managing the fluid as it exits the body. This can, unexpectedly, be achieved without typical densification stiffening (for wet integrity) by leveraging resilient upper and lower nonwovens composed of resilient polymers located above and below the loosely packed fluff/AGM matrix of the inner core layer. This absorbent core structure is able to carry the structural load and recover shape without physically being stiff or losing the desired structural properties when the absorbent core structure becomes wet.

It is believed that wet integrity/shape stability in a cellulose rich absorbent core structure without substantial densification and stiffening results when select resilient upper and lower nonwovens 210, 220 are positioned above and below the fluff/AGM matrix of the inner core layer and joined to and around the fluff/AGM matrix. The upper and lower nonwovens require sufficient recovery force to carry the fluff/AGM matrix back to the original state or a stable fiber orientation state following compression. Wrapping or encapsulating a cellulose rich fluff core with a simple cellulose tissue or less resilient nonwoven material may not exhibit sufficient recovery energy to recover shape in-use and particularly when wetted. Structural, wet resilient nonwovens detailed herein may exhibit recovery energies following compression that are sufficient to recover the cellulose rich fiber matrix and are chosen to deliver high compression recovery, with relatively low stiffness, in both dry and wet state.

It was further found that an absorbent core structure could be created without the need for a distinct secondary topsheet layer by integrating fluid handling functionality into the upper nonwoven layer. By directly integrating the upper nonwoven layer and the fluff/AGM matrix during manufacturing (versus combining with a distinct secondary topsheet layer and a separately wrapped core), inter-layer boundary effects that reduce the efficiency of fluid movement may be avoided. As a result, fluid drainage from the upper nonwoven layer into the lower fluff/AGM matrix may be achieved without requiring densification.

Suitable upper nonwoven layers may have a basis weight of from about 30 gsm to about 85 gsm, or from about 35 gsm to about 70 gsm, or from about 40 to about 60 gsm. The upper nonwoven layer may have a Tensile Stiffness of from about 0.3 N/mm to about 1.6 N/mm. The upper nonwoven layer may have a Strain to Break of greater than about 10%, or from about 10% to about 50%, or from about 20% to about 40%. The upper nonwoven layer may have a Permanent Strain of about 0.005 to about 0.013 mm/mm, alternatively from 0.005 to about 0.0090 mm/mm.

Suitable lower nonwoven layers may have a basis weight of from about 10 to about 40 gsm, or from about 15 to about 20 gsm. The lower nonwoven layer may have a Tensile Stiffness of from about 0.2 N/mm to about 1.6 N/mm. The lower nonwoven layer may have a Strain to Break of greater than about 10%, or from about 10% to about 50%, or from about 20% to about 40%. The lower nonwoven layer may have a Permanent Strain of about 0.005 to about 0.013 mm/mm.

The upper and lower nonwoven layers may comprise polymer fibers. Suitable upper and lower nonwoven fibers may be selected from PET (polyethylene terephthalate), PP (polypropylene), a BiCo (Bicomponent fiber) selected from PE/PP (PE sheath and PP core) and/or PE/PET (PE sheath PET core), PLA (polylactic acid), and combinations thereof.

Suitable upper nonwovens may comprise from about 60 to about 100%, or from about 70% to about 100% synthetic fibers, and from about 0 to about 40%, or from about 0 to about 30% regenerated cellulosic fibers, such as rayon and/or viscose.

The upper nonwoven layer may comprise fibers having a staple length of greater than about mm, or greater than about 25 mm, or from about 10 mm to about 100 mm, or from about 20 mm to about 75 mm, or from about 25 mm to about 50 mm. The upper nonwoven layer may comprise fibers having a fiber diameter of from about 1.3 DTex to about 10

DTex, alternatively from about 1.3 DTex to about 6.0 DTex, or from about 2.0 DTex to about 5.0 DTex. In some configurations, the upper nonwoven layer may comprise fibers, wherein the fibers are a blend of staple fibers having a fiber diameter of from about 2.0 DTex to about 10 DTex.

The lower nonwoven layer may comprise fibers having a length of greater than about 10 mm, or greater than about 25 mm, or from about 10 mm to about 100 mm, or from about 20 mm to about 75 mm, or from about 25 mm to about 50 mm. In some configurations, the lower nonwoven layer may comprise continuous fibers. The lower nonwoven layer may comprise fibers having a fiber diameter of from about 1.3 DTex to about 5.0 DTex, alternatively from about 1.3 DTex to about 3.3 DTex, alternatively from about 1.3 DTex to about 2.2 DTex, alternatively from about 2.0 DTex to about 10 DTex. In some configurations, the lower nonwoven layer may comprise fibers, wherein the fibers are a blend of fibers having a fiber diameter of from about 0.1 DTex to about 6.0 DTex.

In some configurations, suitable fiber combinations may include upper nonwoven polymer fibers having a diameter of from about 2.0 DTex to about 10 DTex and lower nonwoven polymer fibers having a diameter of from about 1.7 DTex to about 5 DTex. In some configurations, suitable fiber combinations may include upper nonwoven polymer fibers having a diameter of from about 1.3 DTex to about 2.2 DTex and lower nonwoven polymer fibers having a diameter of from about 1.7 DTex to about 5 DTex.

Figure 2A:
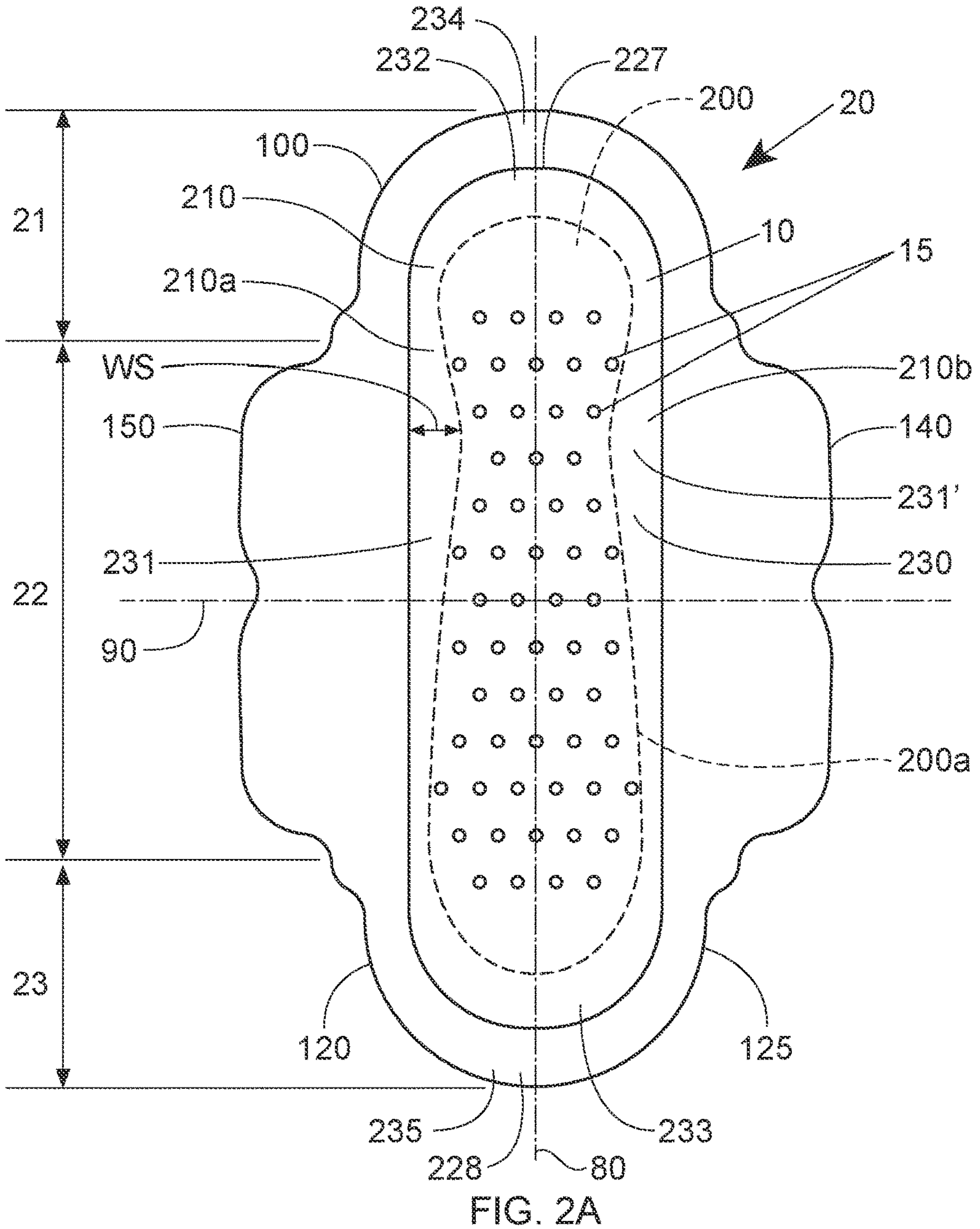
FIG. 2A is a representation of an absorbent article in accordance with the present disclosure.

Referring to FIGS. 2A and 3, absorbent article 20 comprises an absorbent core structure 10 comprising an upper nonwoven layer 210 and a lower nonwoven layer 220 with an inner core layer 200 disposed therebetween. FIG. 2A is a top view of absorbent article 20 with the topsheet removed for simplicity. FIG. 3 is a cross section view of absorbent core structure 10.

Absorbent article 20 and absorbent core structure 10 each include a front region 21, a back region 23, and a middle region 22 disposed intermediate the front region and the back regions. Upper nonwoven layer 210 may comprise a left side region 210*a* and a right side region 210*b*, and lower nonwoven layer 220 may comprise a left side region 220*a* and a right side region 220*b*. The upper and lower nonwoven layers 210, 220 may extend outwardly from an inner core layer perimeter 200*a* and may be joined together to form a perimeter seal 230. In some configurations, the entire inner core layer 200 may be located inboard of the perimeter seal 230. The perimeter seal 230 may help to seal the liquid absorbent material of the inner core layer 200 inside the upper and lower nonwoven layers 210, 220. Perimeter seal 230 may comprise at least a first lateral seal region 231 and a second lateral seal region 231'. In some configurations, perimeter seal 230 may further comprise a front perimeter seal region 232 and/or a back perimeter seal region 233. In some configurations, the perimeter seal 230 may extend around the entire inner core layer perimeter 200*a*. In some configurations, the perimeter seal 230 may extend partially around the inner core layer perimeter 200*a*.

In some configurations, the inner core layer 200 may be contained within the upper nonwoven layer 210 and the lower nonwoven layer 220 by substantially sealing at least a left side region 210*a*, 220*a* and a right side region 210*b*, 220*b* of the upper nonwoven layer 210 and the lower nonwoven layer 220. In some configurations, the inner core layer 200 may be contained within the upper nonwoven layer 210 and the lower nonwoven layer 220 by sealing at least a portion of the left side region 210*a*, 220*a* and the right side region 210*b*, 220*b* of the upper nonwoven layer 210 and the lower nonwoven layer 220.

The perimeter seal 230 may have a seal width WS of between about 1 mm and about 10 mm, or between about 2 mm and about 8 mm, or between about 3 mm and 6 mm. The seal width WS may be uniform or may vary about the perimeter of the inner core layer.

In some configurations, the absorbent article 20 may also comprise a front end seal 234 positioned in a front end region 227 of the absorbent article and a back end seal 235 positioned in a back end region 228 of the absorbent article. The front end seal 234 and/or back end seal 235 may seal the topsheet, upper nonwoven layer, lower nonwoven layer, and the backsheet together. In some configuration, the front end seal 234 and/or the back end seal 235 may seal the topsheet and the backsheet. In some configurations, the front end seal 234 and/or the back end seal 235 may be a crimp seal.

In some configurations, the upper and lower nonwoven layers 210, 220 may be discrete materials that can be cut to approximately the size and shape of the inner core layer 200 so as to fit between the topsheet and backsheet but may not extend substantially into either the front end seal 234 or the back end seal 235. In some configurations, the inner core layer 200, upper nonwoven layer 210 and/or lower nonwoven layer 220 may be shaped, meaning it is non-rectangular. In some configurations, the upper and/or lower nonwoven layers 210, 220 may extend from the front end region 227 of the absorbent article to the back end region 228 of the absorbent article.

Nonwoven layers comprising polymer fibers may hold their shape and resist plasticizing when wet when attached to the fluff/AGM matrix through the application of a core construction adhesive that is applied either directly to the fluff/AGM matrix or the resilient nonwoven layer via a conventional spray coating application chosen to achieve a bond but not disrupt the flow of fluid to the fluff/AGM matrix. Additionally, the upper and lower nonwoven layers 210, 220 may have at least a partial perimeter seal 230 to better connect the upper and lower nonwoven layers 210, 220 with the inner core layer 200 contained within the upper and lower nonwoven layers 210, 220. The perimeter seal 230 may be positioned in at least the middle region 22 of the absorbent article and/or the absorbent core structure. Without being limited by theory, it is believed that the middle region 22 (located between the wearer's thighs during use) may be subjected to the most frequent and/or highest forces during use. It was found that the presence of at least a partial perimeter seal at a left side region and a right side region of the upper nonwoven layer and the lower nonwoven layer external to the fluff/AGM matrix, where the upper and lower nonwoven layers are bonded by conventional means (e.g., adhesives, polymer welding, and/or strong physical entanglement), may help to ensure the upper and lower nonwovens maintain their structural function during physical deformations without separating, limiting any potential integrity and bunching issues. Creating a perimeter seal may allow for any excess nonwoven material to be removed to enable an absorbent core structure to be shaped to conform to inner thigh geometry.

Suitable upper and lower nonwoven layer materials may bend and recover their original shape following the bending force Flimsy or highly flexible materials readily bend at low peak force (load) and with low bending energy. Unsuitable materials, while readily bending, do not have sufficient recovery energy and so retain a deformed, bent state because of insufficient recovery energy. Suitable materials have sufficient energy to recover their initial pre-bent state. The materials with sufficient bending recovery energy may be considered resilient upper and lower nonwoven layers.

As noted above, the upper and lower nonwovens include polymer fibers. Polymer fibers may be included to help provide structural integrity to the upper and lower nonwovens. The polymer fibers can help increase structural integrity of the upper and lower nonwovens in both a machine direction (MD) and in a cross-machine direction (CD), which can facilitate web manipulation during processing of the upper and lower nonwovens for incorporation into a pad.

Polymer fibers of any suitable composition may be selected. Some examples of suitable polymer fibers may include bi-component fibers comprising polyethylene (PE) and polyethylene terephthalate (PET) components or polyethylene terephthalate and co-polyethylene terephthalate components. The components of the bi-component fiber may be arranged in a sheath-core configuration, a side-by-side configuration, an eccentric sheath-core configuration, a trilobal arrangement, or any other desired configuration. In some configurations, the polymer fibers may include bi-component fibers having PE/PET components arranged in a concentric, sheath-core configuration, wherein the polyethylene component forms the sheath.

While other materials may be useful in creating a resilient structure, it is believed that the stiffness of a PET core component in a sheath-core fiber configuration is useful for imparting resilience to the upper and lower nonwovens. In synergistic combination, a PE sheath component, having a lower melting temperature than the PET core component, may be utilized to provide inter-fiber melt/fusion bonding, effected via heat treatment of the precursor batt. This can help provide tensile strength to the web in both the MD and CD. Such inter-fiber bonds may serve to reduce fiber-to-fiber sliding, and thereby further contribute to imparting shape stability and resiliency to the material even when it is wetted.

Where a relatively higher weight fraction of polymer fibers is included, more connections within the structure may be created via heat treatment. However, too many connection points may impart greater stiffness to the upper and lower nonwovens than may be desirable. For this reason, selecting the weight fraction of the polymer fibers may involve prioritizing and balancing competing needs for stiffness and softness in the upper and lower nonwovens.

As noted above, the upper and lower nonwovens may additionally include polymer fibers which increase resiliency of the upper and lower nonwovens. The resilient polymer fibers may help the upper and lower nonwovens maintain permeability and compression recovery. In some configurations, the upper and lower nonwovens may comprise resilient polymer fibers having varying cross sections, e.g., round and hollow spiral, and/or may comprise resilient fibers having varying sizes.

The polymer fibers may be resilient and may be spun from any suitable thermoplastic resin, such as polypropylene (PP), polyethylene terephthalate (PET), or other suitable thermoplastics known in the art. The average staple length of the resilient polymer fibers may be selected to be in the range of greater than about 10 mm, from about 20 mm to about 100 mm, or about 30 mm to about 50 mm, or about 35 mm to about 50 mm. The resilient polymer fibers may have any suitable structure or shape. For example, the resilient polymer fibers may be round or have other shapes, such as spiral, scalloped oval, trilobal, scalloped ribbon, and so forth. Further, the resilient polymer fibers may be solid, hollow, or multi-hollow. The resilient polymer fibers may be solid and round in shape. In other suitable examples, resilient polymer fibers may include polyester/co-extruded polyester fibers. Other suitable examples of resilient polymer fibers may include bi-component fibers such as polyethylene/polypropylene, polyethylene/polyethylene terephthalate, polypropylene/polyethylene terephthalate bicomponent fibers. These bi-component fibers may have a sheath/core configuration.

The resilient polymer fibers may also be polyethylene terephthalate (PET) fibers, or other suitable non-cellulosic fibers known in the art. PET fibers may be imparted with any suitable structure or shape. For example, the PET fibers may be round or have other shapes, such as spiral, scalloped oval, trilobal, scalloped ribbon, hollow spiral, and so forth. The PET fibers may be solid, hollow or multi-hollow. In one particular example, PET fibers may be hollow in cross section and have a curl or spiral configuration along their lengths. Optionally, the resilient polymer fibers may be spiral-crimped or flat-crimped. The resilient polymer fibers may have an average crimp count of about 4 to about 12 crimps per inch (cpi), or about 4 to about 8 cpi, or about 5 to about 7 cpi, or about 9 to about 10 cpi. Particular non-limiting examples of resilient polymer fibers may be obtained from Wellman, Inc. (Ireland) under the trade designations H1311 and T5974. Other examples of suitable resilient polymer fibers are disclosed in U.S. Pat. No. 7,767,598.

The stiffening polymer fibers and resilient polymer fibers should be carefully selected. For example, while the constituent polymers forming the stiffening polymer fibers and the resilient polymer fibers may have similarities, resilient polymer fiber composition should be selected such that their constituents' melting temperature(s) is/are higher than that of the bondable components of the stiffening polymer fibers. Otherwise, during heat treatment, resilient polymer fibers could bond to stiffening polymer fibers and vice versa, and thereby an overly rigid structure. To avoid this risk where the stiffening polymer fibers include bicomponent fibers, e.g., core-sheath configuration fibers with a sheath component of relatively lower melting temperature at which fusion bonding will occur, the resilient polymer fibers may comprise the constituent chemistry of only the core, which may be a polymer having a relatively higher melting temperature.

Nonwoven performance can be impacted by a combination of the nonwoven fiber polymer choice, fiber properties and how the fibers are arranged or connected. Nonwoven selection can impact the absorbent article's ability to recover its shape following compression, bending and extension (stretching) forces present in-use with body motion. If the fibers are short fibers (less than about 10 mm) then they are likely to irreversibly rearrange under extension and compressive forces. The rearranging (changing their orientation/state) of fibers in a fiber matrix dissipates the tensile (elongation) or compressive forces so that the energy used to affect the deformation is no longer available for recovery to the original shape. Longer fiber networks (typically greater than about 10 mm but less than about 100 mm) can dissipate the tensile/compressive forces typical of bodily motions along the fiber length and across the structure. As a result, the imparted forces are available to recover the structure to its original state. Longer fiber networks composed of finer fibers (less than about 15 to about 20 microns and about 2.0 DTex) more readily elongate and compress. As a result, the fluff/AGM structure can deform more readily (and to a higher degree) but the energy associated with these deformations is relatively small and insufficient to carry the structure back to its original state. Thicker fiber, such as greater than about 2.0 DTex to about 10 DTex, are both flexible under bodily forces but provide sufficient fiber and web recovery energy to return the structure to its original state.

The fiber arrangement in a long fiber network from a structural standpoint can impact the performance of the absorbent articles containing these nonwovens. Long fiber webs of thicker fibers are typically loftier than a conventional thin spunbond nonwoven web composed of continuous fine fibers that are closely spaced and physically bonded together. Creating a web of thicker fibers arranged in a more randomized orientation such as those that can be achieved via carding, hydro-entangling and needling are able to elongate and compress, whereby the fibers only temporary adjust their arrangement (space between the fibers exist for these arrangements) and are able to carry/store the deformation forces and this energy is available for recovering the structural shape.

Additionally finer (less than about 2.0 DTex) synthetic fibers such as BiCo and PP fibers commonly found in spunbond are closely spaced, relatively parallel aligned and closely bonded together. The bonded fibers within these spunbond webs are so interconnected (with closely spaced point bonds) that in tensile (elongation) the fibers at the polymer level are forced to stretch this results in polymer chains within the fiber permanently rearranging and as a result the fibers themselves potentially remaining permanently elongated (permanently strained) and no longer able to recover to their initial state.

In some configurations, the upper nonwoven layer may substantially absorb fluid while minimizing the spreading of the fluid on the surface. Without being limited by theory, it is believed that this can be achieved with the combination of a highly wettable material with an open fiber structure best met with thicker (>2.0 DTex) staple nonwoven fibers. In some aspects, the upper nonwoven layer may have a Wet Penetration Time of less than about 4 seconds, or from about 0.1 to about 4 seconds, or from about 0.5 to about 3 seconds, or from about 0.75 to about 2.5 seconds, as measured according to the Wet Penetration Time Method described herein.

The upper nonwoven layer may have a Capillary Work Potential (CWP) of from about 200 $mJ/m^2$ to about 400 $mJ/m^2$ as measured according to the Pore Volume Distribution (PVD) Method as described herein, or from about 225 $mJ/m^2$ to about 375 $mJ/m^2$.

The upper nonwoven layer may have a Permeability value of from about 150 Darcy to about 1000 Darcy as measured according to the Permeability Measurement Method described hereinafter, or from about 250 Darcy to about 990 Darcy.

In some aspects, the polymer fibers in the upper nonwoven layer and the polymer fibers of the lower nonwoven layer may be different. In some aspects, the polymer fibers in the upper nonwoven layer and the polymer fibers of the lower nonwoven layer may be the same.

In some configurations, the upper and/or lower nonwovens may be airthrough bonded carded nonwovens, highloft nonwovens, hydro-entangled nonwovens, and combinations thereof. The upper nonwoven may be an air through bonded nonwoven or a hydroentangled nonwoven. The lower nonwoven may be an air through bonded nonwoven or a hydroentangled nonwoven.

Suitable nonwoven materials examples may include, but are not limited to, the following materials: (i) a 40 gsm carded resilient nonwoven material produced by Yanjan China (material code; ATB Z87G-40-90) which is a carded nonwoven composed of a blend of 60% 2 DTex and 40% 4 DTex BiCo (PE/PET) fibers. The fibers are bonded (ATB=Through 'hot' Air Bonded) to create a wet resilient network. The material basis weight is 40 gsm and its caliper (under 7 KPa) is about 0.9 mm Without being limited by theory, it is believed that because of the presence of the 4 DTex BiCo fibers and the fiber-to-fiber bonded BiCo network, the material has a low Permanent Strain (less than about 0.013 mm/mm) and a sufficient Dry Recovery Energy (greater than about 0.03 N*mm) in the Wet and Dry CD Ultra Sensitive 3 Point Bending Method. The material has a high void volume to hold a fluid gush and is highly permeable. The material is compressible, so while its initial thickness is high under body pressures (70 $g/m^2$), it can compress and allow for more efficient fluid movement from the topsheet through the material and into the inner core layer; (ii) a 55 gsm resilient spunlace material produced by Sandler Germany (material code: 53FC041001), which is a hydro-entangled nonwoven that is produced via a carding step (like the nonwoven described above) followed by hydro-entangling with an elevated drying step (as described in US Patent Publication No. 2020/0315873A1) that creates both an entangled and BiCo bonded resilient network. It comprises a fiber blend of 30% 10 DTex HS-PET, 50% 2.2 DTex BiCo (PE/PET), and 20% 1.3 DTex rayon. As such the material has a low Permanent Strain (less than about 0.013 mm/mm) and a sufficient Dry Recovery Energy (greater than about 0.03 N*mm) in the Wet and Dry CD Ultra Sensitive 3 Point Bending Method. The presence of high levels of higher Dtex fibers can help to keep the structure open (permeable) and with sufficient void volume (thickness) to hold a gush. The presence of rayon can improve capillarity so that the material can offer a balance of capillarity and permeability without having too strong of a capillarity to compete with the fluff/AGM matrix for fluid; and (iii) a 50 gsm resilient spunlace material produced by Sandler Germany (material code: 53FC041005 opt82), which is a hydro-entangled nonwoven that is produced via a carding step (like the nonwoven described above) followed by hydro-entangling with an elevated drying step (as described in US Patent Publication No. 2020 0315873A1) that creates both an entangled and BiCo bonded resilient network. It comprises a fiber blend of 60% 5.8 DTex BiCo (PE/PET), 20% 3.3 DTex tri-lobal 'structural' rayon, and 20% 1.3 DTex rayon. As such the material has a low Permanent Strain (less than about 0.013 mm/mm) and a sufficient Dry Recovery Energy (greater than about 0.03 N*mm) in the Wet and Dry CD Ultra Sensitive 3 Point Bending Method. While this material has 40% rayon that can soften when wet, the use of structural tri-lobal rayon fibers can help structural stability in the wet state. The presence of the structural tri-lobal rayon can also lead to a higher level of capillarity due to the higher surface to volume of tri-lobal rayon shape while also achieving a high level of permeability.

In combination with adjustment of pore size, volume, and number via selection of appropriate fiber size, basis weight, and extent of consolidation, the manufacturer may wish to select fiber constituents for having particular surface chemistry(ies), e.g., fibers with hydrophobic surfaces, hydrophilic surfaces, or a blend of differing fibers and/or z-direction stratification or gradient thereof. Fibers having hydrophilic surfaces will tend to attract and move aqueous components of menstrual fluid there along in a manner conducive to wicking and rapid fluid acquisition following discharge. At the same time, however, a predominance of hydrophilic fibers surfaces within the topsheet may increase a tendency of the topsheet to reacquire fluid from absorbent components beneath (rewet), which can cause an undesirable wet feel for the user. On the other hand, fibers having hydrophobic surfaces will tend to repel aqueous components of menstrual fluid and/or resist movement of fluid along their surfaces, thereby tending to resist wicking—but also to resist rewetting. The manufacturer may wish to seek an appropriate balance in selecting constituent fibers having hydrophilic surfaces, fibers having hydrophobic surfaces, or a blend and/or z-direction stratification thereof, in combination with fiber size, fiber consolidation level, and resulting topsheet pore size, volume and number, for any particular product design.

The inner core layer is produced in an airlaying process. Streams of cellulose fiber and AGM are carried on a fast moving airstream and deposited into a three dimensionally shaped pocket on a rotating forming drum with a vacuum below to draw the cellulose and AGM into the pocket in a laydown station. This shaped pocket provides the actual physical shape of the absorbent core structure. The upper or lower nonwoven may be first introduced onto the forming drum and under the vacuum the upper or lower nonwoven are drawn into the 3-dimensional pocket shape. In this case, the cellulose and AGM material stream is deposited on the upper (or lower nonwoven material) directly in the forming station. Prior to entering the forming station, the nonwoven is coated with an adhesive to provide a stronger connection of the cellulose and AGM to the nonwoven layer. On exiting the laydown section, the second remaining nonwoven layer is combined with the nonwoven carrying the cellulose and AGM layer exiting the laydown section. This second remaining nonwoven (either upper or lower nonwoven depending on what nonwoven is run through the laydown section) is precoated with adhesive to enable a perimeter seal and to better integrate the cellulose and AGM without hindering the flow of liquid into the cellulose and AGM matrix. In another approach, a nonwoven is not first introduced into the forming station and the cellulose and AGM mass is held on the forming drum under vacuum until it is ejected onto either the upper or lower nonwoven layer that has an adhesive applied as detailed above and then sealed with the second remaining nonwoven to create the absorbent core structure. The width of the upper and lower nonwoven webs are typically chosen to be wider than the maximum width of the shaped cellulose and AGM matrix so as to enable an effective perimeter seal where the two nonwovens connect, at least on the left and right most sides of the absorbent core structure.

The inner core layer may comprise any of a wide variety of liquid absorbent materials commonly used in absorbent articles, such as comminuted wood pulp, which is generally referred to as airfelt. One suitable absorbent core material is an airfelt material which is available from Weyerhaeuser Company, Washington, USA, under Code No. FR516. Examples of other suitable liquid absorbent materials for use in the absorbent core may include creped cellulose wadding; meltblown polymers including coform; chemically stiffened, modified or cross-linked cellulosic fibers; synthetic fibers such as crimped polyester fibers; peat moss; cotton; bamboo; absorbent polymer materials; or any equivalent material or combinations of materials; or mixtures of these.

Absorbent polymer materials for use in absorbent articles typically comprise water-insoluble, water-swellable, hydrogel-forming crosslinked absorbent polymers which are capable of absorbing large quantities of liquids and of retaining such absorbed liquids under moderate pressure.

The absorbent polymer material for the absorbent cores according to the present disclosure may comprise superabsorbent particles, also known as "superabsorbent materials" or as "absorbent gelling materials". Absorbent polymer materials, typically in particle form, may be selected among polyacrylates and polyacrylate based materials, such as for example partially neutralized, crosslinked polyacrylates. The term "particles" refers to granules, fibers, flakes, spheres, powders, platelets and other shapes and forms known to persons skilled in the art of superabsorbent particles. In some aspects, the superabsorbent particles may be in the shape of fibers, i.e., elongated, acicular superabsorbent particles.

In some configurations, the absorbent polymer material may be a superabsorbent particle having an average particle size in a dry state of between about 30μ and about 1,000μ, preferably between about 50μ and about 800μ, more preferably between about 80μ and about 700μ, most preferably between about 100μ and about 600μ. Smaller particle sizes within the preferred ranges above can be advantageous as this results in optimum performance Smaller particle sizes, e.g., below about 100μ, for example between about 30μ and about 100μ, can be beneficial for fluid handling capability, wherein particles of such a small size have to be effectively and stably contained within the structure of the absorbent article. "Particle size" as used herein means the weighted average of the smallest dimension of the individual particles. The average particle size of a material in particulate form, namely for example the absorbent polymer material, can be determined as it is known in the art, for example by means of dry sieve analysis. Optical methods, e.g. based on light scattering and image analysis techniques, can also be used.

According to the present disclosure the absorbent polymer material, typically e.g., in particle form, can be selected among the polyacrylate based polymers described in the PCT Patent Application WO 07/047598, which are polyacrylate based materials very slightly crosslinked, or substantially not crosslinked at all. Suitable superabsorbent particles are also described in U.S. Pat. No. 9,622,916.

In some configurations, the inner core layer may comprise from about 125 gsm to about 400 gsm liquid absorbent material, or from about 150 gsm to about 350 gsm, or from about 175 gsm to about 325 gsm.

In some configurations, the inner core layer may comprise cellulosic fibers and superabsorbent particles. The inner core layer may comprise from about 50% to about 85% cellulosic fibers, or from about 55% to about 80%, or from about 60% to about 75%, all by weight of the inner core layer. The inner core layer may comprise from about 10% to about 50% superabsorbent particles, or from about 15% to about 50%, or from about 20% to about 40%, or from about 25% to about 35%, all by weight of the inner core layer. Preferably, the inner core layer may comprise from about 125 gsm to about 400 gsm cellulosic fibers. The inner core layer may comprise from about 20 gsm to about 100 gsm superabsorbent particles.

In some configurations, the inner core layer may comprise from about 50% to about 85% cellulosic fibers and from about 15% to about 50% superabsorbent particles. The resulting absorbent core structure may have an average density of between about 0.045 g/cm$^3$ and about 0.15 g/3, or between 0.045 g/cm$^3$ and 0.12 g/cm$^3$. The absorbent article may have an average density of between about 0.045 g/cm$^3$ and about 0.16 g/cm$^3$.

The absorbent core structures may compress and recover their original shape following the compression step. Suitable absorbent core structures require a low force to compress (less resistance) and the structure is able to recover its shape as the user, in a cyclic fashion, compresses and releases the compressive force with various body movements. To achieve this the structure sustains sufficient recovery energy following multiple cyclic compressions. Without sufficient recovery energy the structure remains in a compressed bunched state with insufficient force (stored energy) to recover.

As shown in FIGS. 1, 2A-2C, 4, and 5 the absorbent core structure structure may comprise a plurality of structural bond sites 15. The structural bond sites 15 may be symmetric and/or asymmetrical and may be any shape including, but not limited to, circles, ovals, hearts, diamonds, triangles, stars, and/or X shaped. The structural bond sites 15 may be on the absorbent article and/or on the absorbent core structure. In some configurations, the structural bond sites may have a bond area of from about 2 $mm^2$ to about 5 $mm^2$. In some configurations, the total structural bond area may be from about 0.5% to about 5%, or from about 0.75% to about 4.5%, or from about 1% to about 4% of the absorbent core structure, as measured according to the Structural Bond Sites Pattern Spacing and Area Measurement Method. In some configurations, the total structural bond area may be from about 1% to about 4% of the absorbent article as measured according to the Structural Bond Sites Pattern Spacing and Area Measurement Method. The average distance between the structural bond sites may be from about 10 mm to about 32 mm. In some configurations, the average distance between the structural bond sites may be greater than about 20 mm. In some configurations, the structural bond sites may have a maximum width of from about 1 mm to about 6 mm, or from about 1.5 mm to about 5 mm, or from about 2 mm to about 4 mm Without being limited by theory, it is believed that the average distance between structural bond sites and/or the size of the structural bond sites may help to maintain the structural integrity of the absorbent core structure without creating an undesirable stiffness that may inhibit the ability of the absorbent article to conform to the body.

In some configurations, the structural bond sites may be distributed across the absorbent article and/or absorbent core structure or they may be clustered in regions of the absorbent article and/or absorbent core structure. In some configurations, the structural bond sites may be clustered in the middle region 22 of the absorbent article and/or absorbent core structure. In some configurations, the middle region 22 of the absorbent article and/or absorbent core structure may be free from structural bond sites and may be surrounded by an area of structural bond sites and/or embossing. In some configurations, the absorbent article may comprise one or more flex bond channel regions 160, wherein the flex bond channel regions may be a continuous depression and/or a series of individually compressed, closely spaced embossments.

In some configurations, the structural bond sites 15 may join the topsheet 110, the upper nonwoven layer 210, the absorbent core structure 10, and the lower nonwoven layer 220. In some configurations, the structural bond sites 15 may join the upper nonwoven layer 210, the absorbent core structure 10, and the lower nonwoven layer 220.

Suitable absorbent articles and/or absorbent core structures may comprise an upper nonwoven layer and lower nonwoven layer that are closer together in the Z direction at the structural bond sites but are not melted together. Since these structural bond sites are not melted together, they may not be permanent in nature and rather may intermingle the materials within the structural bond site. In some configurations, the structural bond sites may be substantially free of fusion bonds.

While the shape of the structural bond sites can be any shape, suitable shapes may be more detailed shapes such as asymmetrical shapes (versus simple dots).

The absorbent article 20 may be resilient and conformable and may deliver a superior in use experience without bunching and/or compressing. The absorbent article may be exposed to bodily forces and can recover to its original state. The absorbent article may have a CD Dry Modulus of between about 0.07 and 0.30 N/$mm^2$ as measured in the Wet and Dry CD and MD 3 Point Bend Method, or from about 0.10 to about 0.25 N/$mm^2$, or from about 0.10 to about 0.20 N/$mm^2$.

The absorbent article may have a of Dry Caliper between about 2.0 mm and about 6.0 mm, or from about 2.0 mm and about 4.5 mm, or from about 2.50 mm to about 4.0 mm, or from about 2.75 mm to about 3.5 mm, as measured according to the Wet and Dry CD and MD 3-Point Method. In some configurations, the absorbent article may have a CD Dry Modulus of between about 0.07 and 0.30 N/$mm^2$ and a Dry Caliper between about 2.0 mm and about 4.5 mm as measured according to the Wet and Dry CD and MD 3-Point Method, or a CD Dry Modulus of between from about 0.10 to about 0.25 N/$mm^2$ and a Dry Caliper of from about 2.50 mm to about 4.0 mm, or a CD Dry Modulus of between about from about 0.10 to about 0.20 N/$mm^2$ and a Dry Caliper of from about 2.75 mm to about 3.5 mm. The absorbent article may have a CD Dry Bending Stiffness of between about 10.0 to about 30.0 N*$mm^2$ as measured in the Wet and Dry CD and MD 3 Point Bend Method, or about 10.0 and about 25.0 N*$mm^2$, or about 10 to about 20 N*$mm^2$, or about 13 to about 20 N*$mm^2$. Particularly suitable absorbent articles include those having a CD Dry Bending Stiffness of between about 10.0 and about 30.0 N*$mm^2$ and a Dry Caliper of from about 2.5 mm to about 4.0 mm as measured according to the Wet and Dry CD and MD 3-Point Method, or a CD Dry Bending Stiffness of about 10 to about 25 N*$mm^2$ and a Dry Caliper of between about 2.5 and 4.0 mm, or a CD Dry Bending Stiffness about 13 to about 30 N*$mm^2$ and a Dry Caliper of from about 2.75 mm to about 3.5 mm.

The absorbent article may have a $5^{th}$ Cycle Wet Energy of Recovery of from about 1.0 to about 3.5 N*mm, or about 1.5 to about 3.0 N*mm, or about 1.5 to about 2.8 N*mm Particularly suitable absorbent articles may have a $5^{th}$ Cycle Wet Energy of Recovery of between about 1.0 and 3.5 N*mm and a $5^{th}$ Cycle Wet % Recovery of from about 29% to about 40%, or a $5^{th}$ Cycle Wet Energy of Recovery of from about 1.5 to about 3.0 N*mm and a $5^{th}$ Cycle Wet % Recovery of from about 29% to about 40%, or a $5^{th}$ Cycle Wet Energy of Recovery from about 1.5 to about 2.75 N*mm and a $5^{th}$ Cycle Wet % Recovery of from about 29% to about 40%.

Absorbent articles composed of the absorbent core structures as disclosed within may also need to deliver a dry touch to the consumer following the addition of fluid as measured by the Light Touch Rewet Method. Absorbent core structures and absorbent articles meeting the above characteristics are designed to comfortably and gently conform more closely and more completely to the wearer's complex anatomical genital shape. Such absorbent articles therefore may also need to be dry to the touch following discharge so as not to irritate the sensitive genital tissues. As such absorbent articles described herein may also maintain a Light Touch Rewet value of less than about 0.15 grams, or less about 0.12 grams, or from about 0 to about 0.15 grams, or from about 0 to about 0.12 grams.

The absorbent article may have a Total Interfacial Free Fluid and Surface Free Fluid value (referred to herein as "Total IFF+SFF") of from about 20 mg to about 200 mg as measured according to the Acquisition and Rewet Test described herein, alternatively from about 40 mg to about 190 mg.

The absorbent article may have a Surface Free Fluid (SFF) value of from about 15 mg to about 175 mg as measured according to the Acquisition and Rewet Test described herein.

The absorbent article may have an Interfacial Free Fluid (IFF) value of from about 12 mg to about 50 mg as measured according to the Acquisition and Rewet Test described herein.

The absorbent article may have a Total Gush Absorbency Time of from about 12 seconds (sec) to about 25 sec as measured according to the Acquisition and Rewet Test described herein.

Figure 2C:
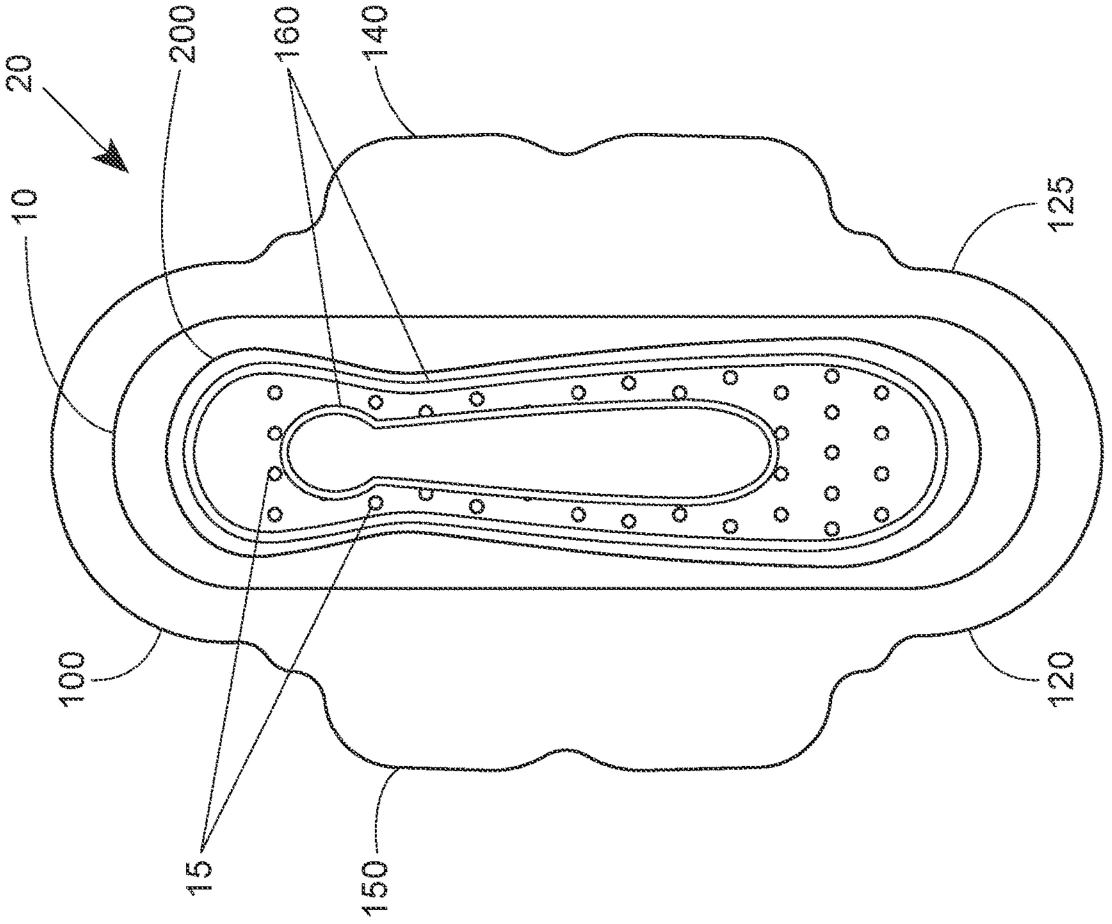
FIG. 2C is another representation of an absorbent article in accordance with the present disclosure.
Figure 2B:
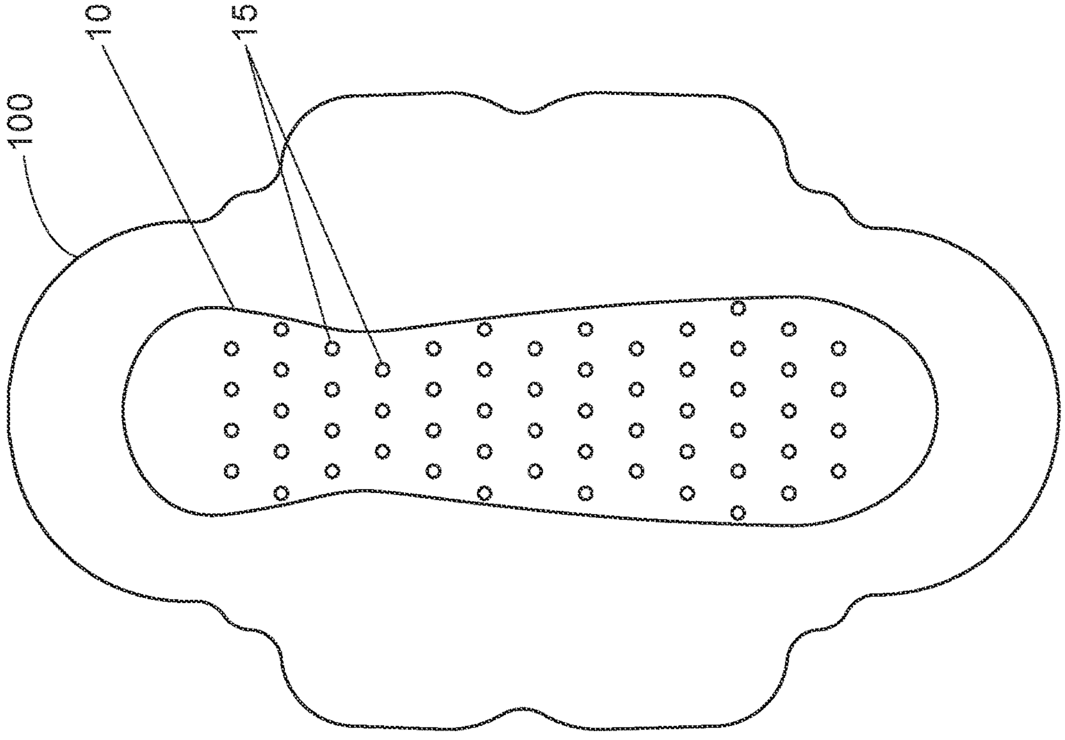
FIG. 2B is another representation of an absorbent article in accordance with the present disclosure.

As shown in FIGS. 2A-2C, the absorbent article 20 further comprises a chassis 100 comprising an absorbent core structure 10. As shown, the absorbent core structure 10 and/or inner core layer 200 may comprise a generally hourglass shape. However, any suitable shape may be utilized. Some examples include offset hourglass (one end is wider than an opposite end and a narrowed mid-section between the ends), bicycle seat shape (one end and central portion are narrower than second end), etc. Side edges 120 and 125 may follow the general contour of the absorbent core structure. So where, the absorbent core structure has an hourglass shape the side edges of the absorbent article 120, 125 may be arranged in an hourglass shape as well. However, forms are contemplated where the side edges 120 and 125 are generally straight or slightly curved such that they do not follow the contour of the absorbent core structure. Additional details are discussed hereafter. The absorbent article 20 may be symmetric about the longitudinal centerline 80 or asymmetric about the longitudinal centerline 80. Similarly, the absorbent article 20 may be symmetric about the lateral centerline 90 or asymmetric about the lateral centerline 90.

Topsheet

Figure 6:
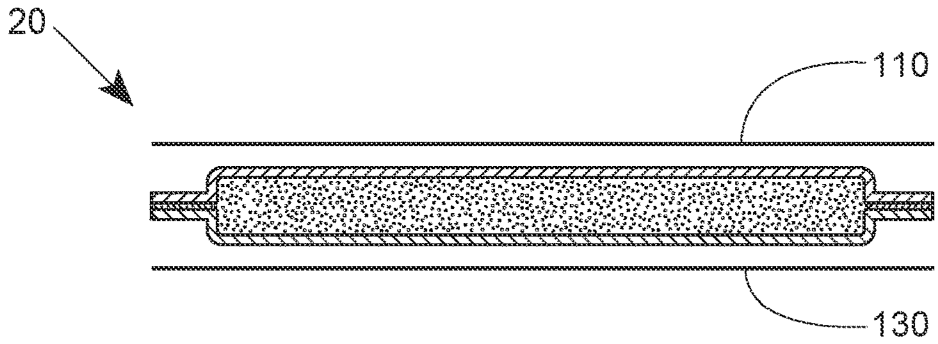
FIG. 6 is a cross section of an absorbent article in accordance with the present disclosure.

Topsheet 110 may be formed of any suitable nonwoven web or formed film material (see FIG. 6). Referring back to the figures, the topsheet 110 is positioned adjacent a wearer-facing surface of the absorbent article 20 and may be joined thereto and to the backsheet 130 by any suitable attachment or bonding method. The topsheet 110 and the backsheet 130 may be joined directly to each other in the peripheral regions outside the perimeter of the absorbent core structure and may be indirectly joined by directly joining them respectively to wearer-facing and outward-facing surfaces of the absorbent article or additional optional layers included with the absorbent article.

The absorbent article 20 may have any known or otherwise effective topsheet 110, such as one which is compliant, soft feeling, and non-irritating to the wearer's skin. A suitable topsheet material will include a liquid pervious material that is comfortable when in contact with the wearer's skin and permits discharged menstrual fluid to rapidly penetrate through it. Some suitable examples of topsheet materials include films, nonwovens, laminate structures including film/nonwoven layers, film/film layers, and nonwoven/nonwoven layers.

Nonlimiting examples of nonwoven web materials that may be suitable for use to form the topsheet 110 include fibrous materials made from natural fibers, modified natural fibers, synthetic fibers, or combinations thereof. Some suitable examples are described in U.S. Pat. Nos. 4,950,264; 4,988,344; 4,988,345; 3,978,185; 7,785,690; 7,838,099; 5,792,404; and 5,665,452.

The topsheet 110 may be compliant, soft feeling, and non-irritating to the wearer's skin. Further, the topsheet 110 may be liquid pervious permitting liquids (e.g., urine, menses) to readily penetrate through its thickness. Some suitable examples of topsheet materials include films, nonwovens, laminate structures including film/nonwoven layers, film/film layers, and nonwoven/nonwoven layers. Other exemplary topsheet materials and designs are disclosed in U.S. Patent Application Publication Nos. 2016/0129661, 2016/0167334, and 2016/0278986.

In some examples, the topsheet 110 may include tufts as described in U.S. Pat. Nos. 8,728,049; 7,553,532; 7,172,801; 8,440,286; 7,648,752; and 7,410,683. The topsheet 20 may have a pattern of discrete hair-like fibrils as described in U.S. Pat. No. 7,655,176 or U.S. Pat. No. 7,402,723. Additional examples of suitable topsheet materials include those described in U.S. Pat. Nos. 8,614,365; 8,704,036; 6,025,535; and US Patent Publication No. 2015/041640. Another suitable topsheet may be formed from a three-dimensional substrate as detailed in US 2017/0258647. The topsheet may have one or more layers, as described in US Patent Publication Nos. 2016/0167334; US 2016/0166443; and US 2017/0258651.

In some examples a topsheet 110 may be formed of a nonwoven web material of a spunbond web including single-component continuous fibers, or alternatively, bi-component or multi-component fibers, or a blend of single-component fibers spun of differing polymer resins, or any combination thereof. The topsheet may also be a formed nonwoven topsheet as disclosed in US Patent Publication No. 2019/0380887.

In order to ensure that fluid contacting the top (wearer-facing) surface of a topsheet will move suitably rapidly in a z-direction to the bottom (outward-facing) surface of the topsheet where it can be drawn into the absorbent article, it may be important to ensure that the nonwoven web material forming the topsheet has an appropriate weight/volume density, reflecting suitable presence of interstitial passageways (sometimes known as "pores") among and between the constituent fibers, through which fluid may move within the nonwoven material. In some circumstances a nonwoven material with fibers that are consolidated too densely will have insufficient numbers and/or volumes and/or sizes of pores, and the nonwoven will obstruct rather than facilitate rapid downward z-direction fluid movement. On the other hand, a nonwoven with fibers that are too large and/or not consolidated enough to provide a certain level of opacity (for purposes of concealing absorbed fluid in the layers beneath) and a substantial appearance may be negatively perceived by users.

The caliper of the topsheet material may be controlled, to balance competing needs for opacity and loft (which call for a higher caliper) vs. a limitation on the z-direction distance that discharged fluid travels through the topsheet from the wearer-facing surface to the outward-facing surface, to reach the absorbent core components below. Thus, it may be desired that the manufacture of the topsheet material be controlled to produce a topsheet material having a caliper of from about 0.20 mm to about 1.0 mm, or from about 0.25 mm to about 0.80 mm, or from about 0.30 mm to about 0.60 mm.

The absorbent article may include an anti-stick agent applied, to at least a portion of the wearer-facing surface of the topsheet. The anti-stick agent may comprise a polypropylene glycol (PPG) material and a carrier. It is believed that an applied anti-stick agent may serve functions that include reducing adherence of menstrual fluid to the user/wearer's skin and/or facilitation of migration of menstrual fluid from the wearer-facing surface of the topsheet, down therethrough to the fluid management and/or absorbent structure layers beneath. Serving these functions can enhance user/wearer perceptions of cleanliness of her skin and of the topsheet, especially after repeated discharges of menstrual fluid.

The anti-stick agents contemplated herein may comprise a PPG material at a level of about 0.1% to about 100%, by weight of the anti-stick agent. In some aspects, the anti-stick agent may include less than about 10%, preferably from about 0.5% to about 8%, and more preferably from about 1% to about 5%, of a PPG material, by weight of the anti-stick agent. In some configurations, the anti-stick agent may include at least about 50%, preferably about 75% to about 100%, and more preferably about 90% to about 100%, of a PPG material, by weight of the anti-stick agent. The anti-stick agents contemplated herein may include a carrier at a total carrier concentration ranging from about 60% to about 99.9%, preferably about 70% to about 99.5%, more preferably about 80% to about 99% by weight of the anti-stick agent.

Examples of a suitable anti-stick agents and/or surfactants useful therein are disclosed in U.S. Patent Publication 2009/0221978 (wherein the composition is called a "lotion"), U.S. Pat. No. 8,178,748, and U.S. Patent Application No. 63/256,164. A particularly preferred example of a suitable polypropylene glycol material is PPG-15 stearyl ether, such as the product sold as CETIOL E, by BASF Corporation (Florham Park, New Jersey, USA) and/or BASF SE (Ludwigshafen, Germany). A particularly preferred example of a suitable carrier is caprylic/capric triglyceride, for example, MYRITOL 318, a product of BASF Corporation (Florham Park, New Jersey, USA) and/or BASF SE (Ludwigshafen, Germany).

Secondary Topsheet (STS)

An STS layer may be included, in some circumstances, between the topsheet and the absorbent core structure to enable the absorbent core structure to readily receive a sudden discharge of fluid, and after receipt, to wick it along x- and y-directions to distribute it across the underlying absorbent core structure.

If included, an STS may be a nonwoven fibrous structure which may include cellulosic fibers, non-cellulosic fibers (e.g., fibers spun from polymer resin(s)), or a blend thereof. To accommodate the folding and lateral gathering of the absorbent article 20, and of the absorbent core structure 10, as described herein, the STS may be formed of a material that is relatively pliable (i.e., has relatively low bending stiffness).

A number of particular examples of suitable STS compositions and structures, as well as combinations thereof with suitable topsheet compositions and structures, are further described in U.S. Apps. Ser. Nos. 16/831,862; 16/831,854; 16/832,270; 16/831,865; 16/831,868; 16/831,870; and Ser. No. 16/831,879; and U.S. Provisional Apps. Ser. Nos. 63/086,610 and 63/086,701. Additional suitable examples are described in U.S. Pat. No. 9,504,613; WO 2012/040315; and US 2019/0021917.

In some configurations, the absorbent article may be free of a secondary topsheet.

Backsheet

The backsheet 130 may be positioned beneath or subjacent an outward-facing surface of the absorbent core structure 10 and may be joined thereto by any suitable attachment methods. For example, the backsheet 130 may be secured to the absorbent core structure 10 by a uniform continuous layer of adhesive, a patterned layer of adhesive, or an array of separate lines, spirals, or spots of adhesive. Alternatively, the attachment method may include heat bonds, pressure bonds, ultrasonic bonds, dynamic mechanical bonds, or any other suitable attachment mechanisms or combinations thereof. In other examples, it is contemplated that the absorbent core structure 10 is not joined directly to the backsheet 130.

The backsheet 130 may be impermeable or substantially impermeable by aqueous liquids (e.g., urine, menstrual fluid) and may be manufactured from a thin plastic film, although other flexible liquid impermeable materials may also be used. As used herein, the term "flexible" refers to materials which are compliant and will readily conform to the general shape and contours of the human body. The backsheet 130 may prevent, or at least substantially inhibit, fluids absorbed and contained within the absorbent core structure 10 from escaping and reaching articles of the wearer's clothing which may contact the absorbent article 20, such as underpants and outer clothing. However, in some instances, the backsheet 130 may be made and/or adapted to permit vapor to escape from the absorbent core structure 10 (i.e., the backsheet is made to be breathable), while in other instances the backsheet 130 may be made so as not to permit vapors to escape (i.e., it is made to be non-breathable). Thus, the backsheet 130 may comprise a polymeric film such as thermoplastic films of polyethylene or polypropylene. A suitable material for the backsheet 130 is a thermoplastic film having a thickness of from about 0.012 mm (0.5 mil) to about 0.051 mm (2.0 mils), for example. Any suitable backsheet known in the art may be utilized with the present invention.

Some suitable examples of materials suitable for forming a backsheet are described in U.S. Pat. Nos. 5,885,265; 4,342,314; and 4,463,045. Suitable single layer breathable backsheets for use herein include those described for example in GB A 2184 389; GB A 2184 390; GB A 2184 391; U.S. Pat. Nos. 4,591,523; 3,989,867; 3,156,242; WO 97/24097; U.S. Pat. Nos. 6,623,464; 6,664,439; and 6,436,508.

The backsheet 130 may have two layers: a first layer comprising a vapor permeable aperture-formed film layer and a second layer comprising a breathable microporous film layer, as described in U.S. Pat. No. 6,462,251. Other suitable examples of dual or multi-layer breathable backsheets for use herein include those described in U.S. Pat. Nos. 3,881,489; 4,341,216; 4,713,068; 4,818,600; EP 203 821; EP 710 471; EP 710 472; and EP 0 793 952.

Other Features

In some configurations, the absorbent article 20 may be provided with adhesive deposits to provide a mechanism for the user to adhere the absorbent article to the inside of her underpants in the crotch region thereof. When the absorbent article 20 is packaged for shipping, handling and storage prior to use, adhesive deposits may be covered by one or more sheets of release film or paper (not shown) that covers/shields the adhesive deposits from contact with other surfaces until the user is ready to remove the release film or paper and place the absorbent article in her underpants for wear/use.

In some configurations, the absorbent article 20 may include opposing wing portions 140, 150 on each side, extending laterally beyond longitudinal edges of the absorbent portions of the absorbent article by a comparatively greater width dimension than that of the forward and rearward portions of the absorbent article. Wings are currently commonly provided with feminine hygiene absorbent articles. As provided, they typically have deposits of adhesive applied to their outward-facing surfaces (surface are outward-facing prior to placement of the absorbent article within the user's underwear and application of the wings). The wing portions may also include deposits of adhesive as described above, which enable the user to wrap the wing portions through the leg openings of the underpants and around the inside edges thereof, and adhere the wing portions to the outward-facing surface/underside of the underpants in the crotch region, providing supplemental holding support for the absorbent article and helping guard the underpants proximate the leg edges thereof against soiling.

Test Methods

Layers of Interest

For any of the methods below in which all the component layers of an article will not be tested, the layers of interest may be separated using cryo-spray as needed from layers which will not be tested.

Strain to Break Method

The force versus displacement behavior of a sample is measured on a universal constant rate of extension test frame (a suitable instrument is the MTS Alliance using TestSuite Software, as available from MTS Systems Corp., Eden Prairie, MN, or equivalent) equipped with a load cell for which the forces measured are within 1% to 99% of the limit of the cell. The sample is subjected to tensile elongation at a constant rate (mm/sec) until it breaks, and the percent strain to break is measured. All testing is performed in a room controlled at 23° C.±3 C.° and 50%±2% relative humidity and test samples are conditioned in this environment for at least 2 hours prior to testing.

The fixtures used to grip the test specimen are lightweight (<80 grams), vise action clamps with half cylinder steel versus rubber coated steel grip faces that are at least 40 mm wide. The fixtures are installed on the universal test frame and mounted such that they are horizontally and vertically aligned with one another.

The test specimen is prepared as follows. Obtain the test material by excising it from an absorbent article, if necessary. When excising the test material, do not impart any contamination or distortion to the material layer during the process. The test specimen is cut from an area on the test material that is free of any folds or wrinkles. The test specimen is 100 mm long (parallel to the lateral axis, or intended lateral axis of the article) and 25.4 mm wide (parallel to the longitudinal axis, or intended longitudinal axis of the article). In like fashion, five replicate test specimens are prepared.

Prepare the universal test frame as follows. Set the initial grip to grip separation distance to a nominal gage length of 80 mm, then zero the crosshead. Program the test frame to move the grips closer together by an intentional slack of 1 mm to ensure no pretension force exists on the test specimen at the onset of the test. (During this motion, the specimen will become slack between the grips.) Next, the grips will move apart at a slack speed of 1 mm/s until the slack preload of 0.05 N is exceeded. (At this point, the crosshead position signal is used to compute the sample slack, the adjusted gage length, and the strain is defined at zero, 0.0). The grips will then move apart at a speed of 1 mm/s until the sample breaks or the extension limit of the instrument is exceeded.

The test is executed by inserting the test specimen into the grips such that the long axis of the specimen is parallel and centered with the motion of the crosshead. Start the test and continuously collect force ("load") and displacement data at a data acquisition rate of 100 Hz.

Construct a graph of load (N) versus displacement (mm). Determine the peak load from the curve, then determine the break sensitivity as follows. Determine the crosshead position at which the load signal decreases by 75% after the peak load is reached, and record as specimen final length (Lf) to the nearest 0.01 mm. The initial length of the specimen is defined by the crosshead position when the slack preload of 0.05 N is exceeded, and this value is recorded as specimen initial length (Li) to the nearest 0.01 mm. Calculate the percent strain to break as follows, and record to the nearest 1 percent.

$$\%\ \text{Strain to Break}=((Lf-Li)/Li)*100$$

In like fashion, the procedure is repeated for all five replicate test specimens. The arithmetic mean of % strain to break among the five replicate test specimens is calculated and reported as % Strain to Break to the nearest 1 percent.

Wet and Dry CD and MD 3 Point Bend Method

The bending properties of an absorbent article test sample are measured on a universal constant rate of extension test frame (a suitable instrument is the MTS Alliance using TestSuite Software, as available from MTS Systems Corp., Eden Prairie, MN, or equivalent) equipped with a load cell for which the forces measured are within 1% to 99% of the limit of the cell. The test is executed on dry test specimens as well as wet test specimens. The intention of this method is to mimic deformation created in the x-y plane by a wearer of an absorbent article during normal use. All testing is performed in a room controlled at 23° C.±3° C. and 50%±2% relative humidity.

The bottom stationary fixture consists of two cylindrical bars 3.175 mm in diameter by 110 mm in length, made of polished stainless steel each mounted on each end with frictionless roller bearings. These 2 bars are mounted horizontally, aligned front to back and parallel to each other, with top radii of the bars vertically aligned and are free to rotate around the diameter of the cylinder by the frictionless bearings. Furthermore, the fixture allows for the two bars to be moved horizontally away from each other on a track so that a gap can be set between them while maintaining their orientation. The top fixture consists of a third cylinder bar also 3.175 mm in diameter by 110 mm in length, made of polished stainless steel mounted on each end with frictionless roller bearings. When in place the bar of the top fixture is parallel to and aligned front to back with the bars of the bottom fixture and is centered between the bars if the bottom fixture. Both fixtures include an integral adapter appropriate to fit the respective position on the universal test frame and lock into position such that the bars are orthogonal to the motion of the crossbeam of the test frame.

Set the gap ("Span") between the bars of the lower fixture to 25 mm±0.5 mm (center of bar to center of bar) with the upper bar centered at the midpoint between the lower bars. Set the gage (bottom of top bar to top of lower bars) to 1.0 cm.

The thickness ("caliper") of the test specimen is measured using a manually-operated micrometer equipped with a pressure foot capable of exerting a steady pressure of 0.1 psi±0.01 psi. The manually-operated micrometer is a deadweight type instrument with readings accurate to 0.01 mm. A suitable instrument is Mitutoyo Series 543 ID-C Digimatic, available from VWR International, or equivalent. The pressure foot is a flat circular moveable face with a diameter no greater than 25.4 mm. The test specimen is supported by a horizontal flat reference platform that is larger than and parallel to the surface of the pressure foot. Zero the micrometer against the horizontal flat reference platform. Place the test specimen onto the platform, centered beneath the pressure foot. The pressure foot is lowered by hand with a descent rate of 3±1 mm/s until the full weight of the pressure is exerted onto the specimen. After 5 seconds elapse, the thickness is recorded as caliper to the nearest 0.01 mm.

The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved.

The absorbent article samples are conditioned at 23° C.±3° C. and 50%±2% relative humidity two hours prior to testing. Dry test specimens are taken from an area of the sample that is free from any seams and residua of folds or wrinkles, and ideally from the center of absorbent article (intersection of longitudinal and lateral midlines). The dry specimens are prepared for MD (machine direction) bending by cutting them to a width of 50.8 mm along the CD (cross direction; parallel to the lateral axis of the sample) and a length of 50.8 mm along the MD (parallel to the longitudinal axis of the sample), maintaining their orientation after they are cut, and marking the body-facing surface (or the surface intended to face the body of a finished article). The dry specimens are prepared for CD (machine direction) bending by cutting them to a width of 50.8 mm along the MD (cross direction; parallel to the lateral axis of the sample) and a length of 50.8 mm along the CD (parallel to the longitudinal axis of the sample), maintaining their orientation after they are cut, and marking the body-facing surface (or the surface intended to face the body of a finished article). Measure the thickness of the test specimen, as described herein, and record as dry specimen caliper to the nearest 0.01 mm. Now measure the mass of the test specimen and record as dry mass to the nearest 0.001 grams. Calculate the basis weight of the specimen by dividing the mass (g) by the area (0.002581 $m^2$) and record as dry specimen basis weight to the nearest 0.01 $g/m^2$. Calculate the bulk density of the specimen by dividing the specimen basis weight ($g/m^2$) by the specimen thickness (mm), then dividing the quotient by 1000, and record as dry specimen density to the nearest 0.01 $g/cm^3$. In like fashion, five replicate dry test specimens are prepared.

Wet test specimens are initially prepared in the exact manner as for the dry test specimen, followed by the addition of test fluid just prior to testing, as follows. First, the thickness and mass of the dry specimen is measured, as described herein, and recorded as initial thickness to the nearest 0.01 mm and initial mass to the nearest 0.001 g. Next, the dry specimen is fully submersed in the test fluid for 60 seconds. After 60 seconds elapse, the specimen is removed from the test fluid and oriented vertically for 30 seconds to allow any excess fluid to drip off. Now the thickness and mass of the wet specimen are measured, as described herein, and recorded as wet specimen caliper to the nearest 0.01 mm and wet specimen mass to the nearest 0.001 g. If desired, the mass of test fluid in the test specimen is calculated by subtracting the initial mass (g) from the wet specimen mass (g) and recording as test specimen fluid amount to the nearest 0.001 g. After the wet test specimen is removed from the test fluid, it must be tested within 10 minutes. In like fashion, five replicate wet test specimens are prepared.

Program the universal test frame for a flexural bend test, to move the crosshead such that the top fixture moves down with respect to the lower fixture at a rate of 1.0 mm/sec until the upper bar touches the top surface of the specimen with a nominal force of 0.02 N, then continue for an additional 12 mm. The crosshead is then immediately returned to the original gage at a rate of 1.0 mm/s. Force (N) and displacement (mm) data are continuously collected at 100 Hz throughout the test.

Load a dry test specimen such that it spans the two lower bars and is centered under the upper bar, with its sides parallel to the bars. For MD bending, the MD direction of the test specimen is perpendicular to the length of the 3 bars. Start the test and continuously collect force and displacement data.

Construct a graph of force (N) versus displacement (mm). From the graph, determine the maximum peak force and record as dry MD peak load to the nearest 0.01 N. Now calculate the maximum slope of the curve between initial force and maximum force (during the loading portion of the curve) and record to the nearest 0.1 unit. Calculate the modulus as follows, and record as dry MD modulus to the nearest 0.001 $N/mm^2$.

$$\text{CD or MD Dry or Wet Bending Modulus } (N/mm^2) = (\text{Slope} \times (\text{Span}^3))/(4 \times \text{specimen width} \times (\text{specimen caliper}^3))$$

Calculate bending stiffness as follows, and record as dry MD bending stiffness to the nearest 0.1 N $mm^2$.

$$\text{CD or MD Dry or Wet Bending Stiffness } (N\ mm^2) = \text{Modulus} \times \text{Moment of Inertia}$$

where Moment of Inertia ($mm^4$)=(specimen width×(specimen caliper$^3$))/12

In like fashion, the procedure is repeated for all five replicates of the dry test specimens. The arithmetic mean among the five replicate dry test specimens is calculated for each of the parameters and reported as Dry Specimen 'Caliper' to the nearest 0.01 mm, Dry Specimen Basis Weight to the nearest 0.01 $g/m^2$, Dry Specimen Density to the nearest 0.001 $g/cm^3$, Dry CD or MD Peak Load to the nearest 0.01 N, Dry CD or MD Bending Modulus to the nearest 0.001 $N/mm^2$, and Dry CD or MD Bending Stiffness to the nearest N $mm^2$.

The overall procedure is now repeated for all five replicates of the wet test specimens, reporting results as Wet CD or MD Peak Load to the nearest 0.01 N, Wet CD or MD Bending Modulus to the nearest 0.001 $N/mm^2$, and Wet CD or MD Bending Stiffness to the nearest N $mm^2$.

Wet and Dry CD Ultra Sensitive 3 Point Bending Method

The CD (cross-direction) bending properties of a test sample are measured using an ultra sensitive 3 point bend test on a universal constant rate of extension test frame (a suitable instrument is the MTS Alliance using TestSuite Software, as available from MTS Systems Corp., Eden Prairie, MN, or equivalent) equipped with a load cell appropriate for the forces being measured. The test is executed on dry test specimens as well as wet test specimens. The intention of this method is to mimic deformation created in the x-y plane by a wearer of an absorbent article during normal use. All testing is performed in a room controlled at 23° C.±3° C. and 50%±2% relative humidity.

The ultra sensitive 3 point bend method is designed to maximize the force signal to noise ratio when testing materials with very low bending forces. The force signal is maximized by using a high sensitivity load cell (e.g., 5N), using a small span (load is proportional to the span cubed) and using a wide specimen width (total measured load is directly proportional to width). The fixture is designed such that the bending measurement is performed in tension, allowing the fixture mass to be kept to a minimum. Noise in the force signal is minimized by holding the load cell stationary to reduce mechanical vibration and inertial effect and by making the mass of the fixture attached to the load cell as low as possible.

Figure 7A:
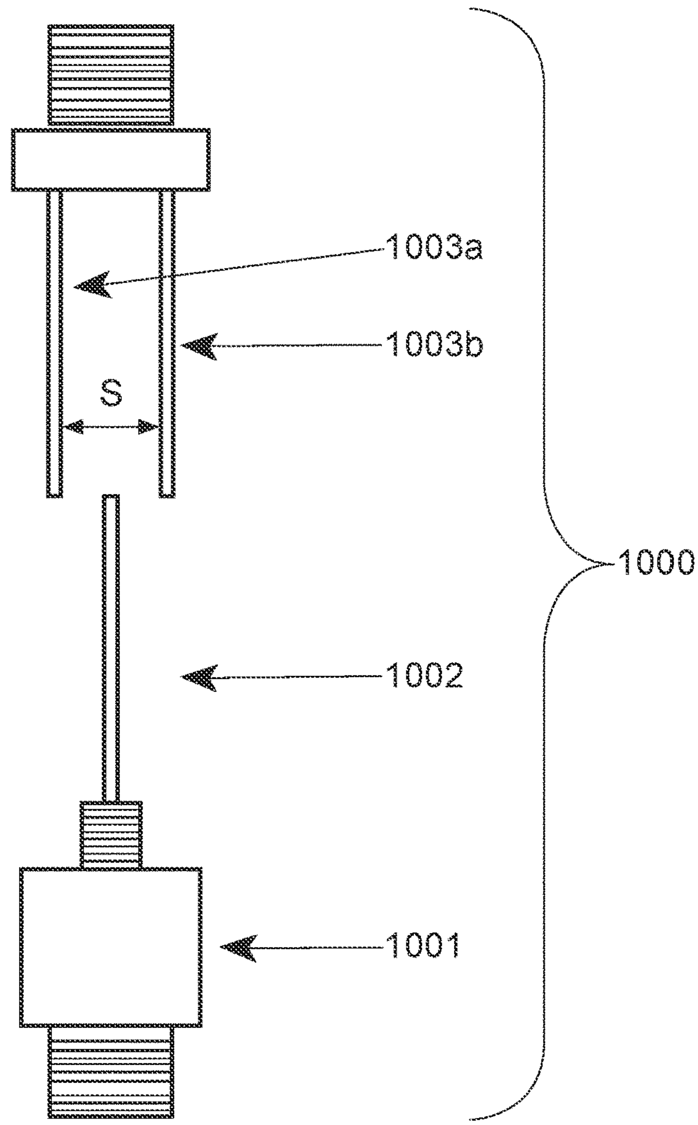
FIGS. 7A-C are a test method arrangement for the Wet and Dry CD Ultra Sensitive 3 Point Bending Method.
Figure 7B:
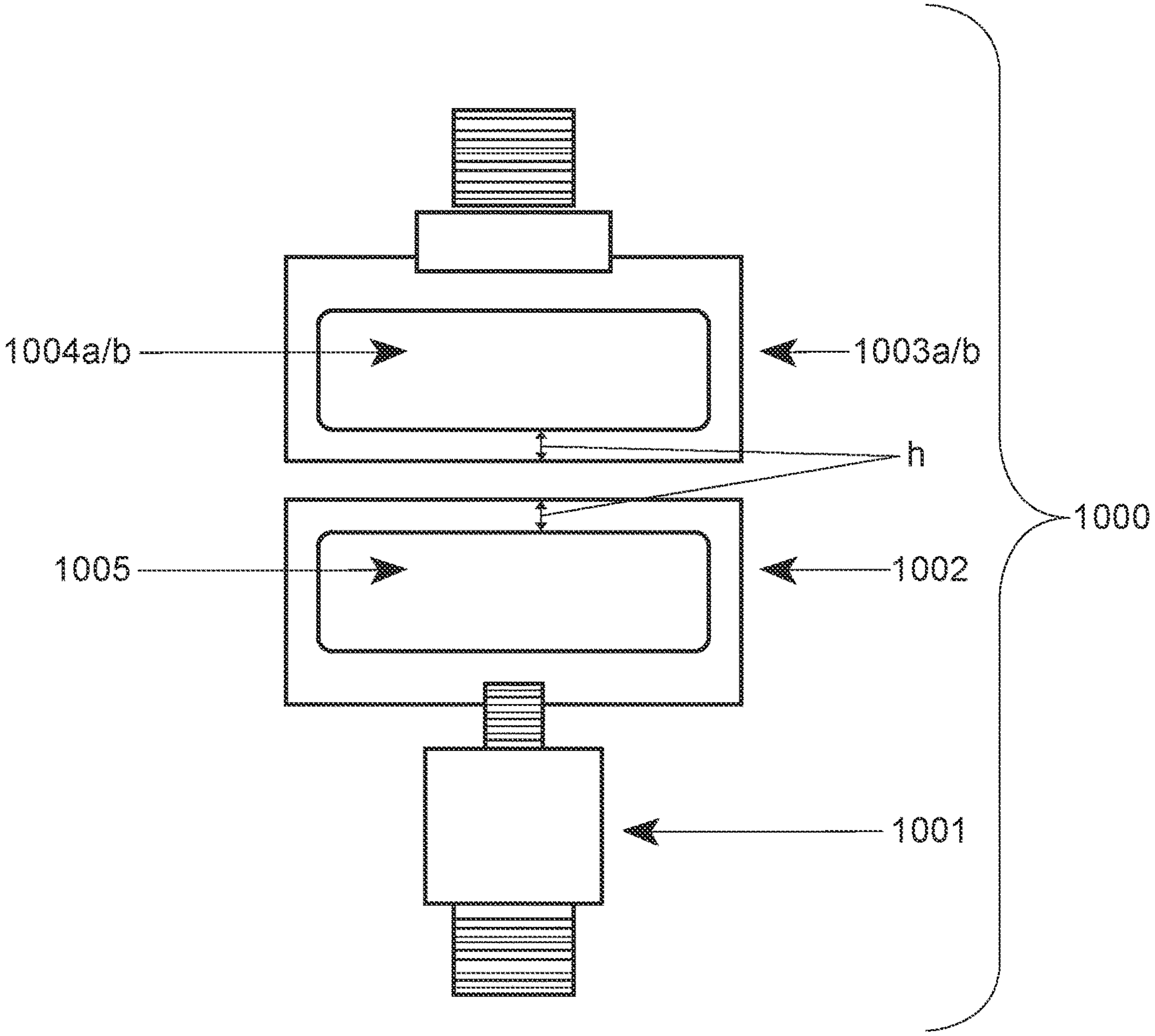
Figure 7C:
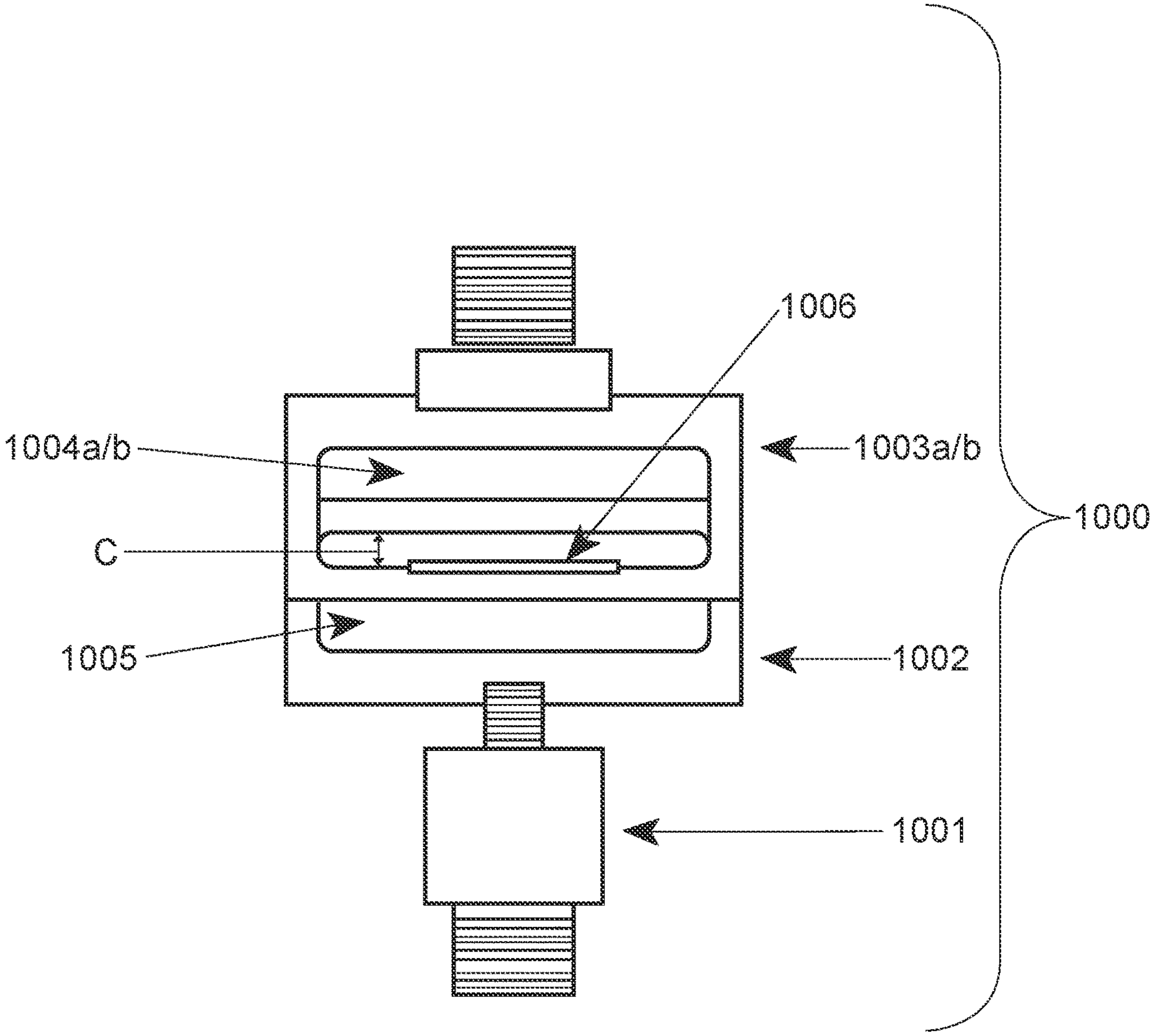

Referring to FIGS. 7A-7C, the load cell 1001 is mounted on the stationary crosshead of the universal test frame. The ultra sensitive fixture 1000 consists of three thin blades constructed of a lightweight, rigid material (such as aluminum, or equivalent). Each blade has a thickness of 1.0 mm, rounded edges and a length that is able to accommodate a bending width of 100 mm. Each of the blades has a cavity 1004*a* and 1004*b* (outside blades) and 1005 (central blade) cut out to create a height, h, of 5 mm of blade material along their horizontal edges. The two outside blades 1003*a* and 1003*b* are mounted horizontally to the moveable crosshead of the universal test frame, aligned parallel to each other, with their horizontal edges vertically aligned. The span, S, between the two outside blades 1003*a* and 1003*b* is 5 mm±0.1 mm (inside edge to inside edge). The central blade 1002 is mounted to the load cell on the stationary crosshead of the universal test frame. When in place, the central blade 1002 is parallel to the two outside blades 1003*a* and 1003*b* and centered at the midpoint between the outside blades 1003*a* and 1003*b*. The blade fixtures include integral adapters appropriate to fit the respective positions on the universal test frame and lock into position such that the horizontal edges of the blades are orthogonal to the motion of the crossbeam of the universal test frame.

The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved.

Samples are conditioned at 23° C.±3° C. and 50%±2% relative humidity two hours prior to testing. Dry test specimens are taken from an area of the sample that is free from any seams and residua of folds or wrinkles. The dry specimens are prepared for CD bending (i.e., bending normal to the lateral axis of the sample) by cutting them to a width of 50.0 mm along the CD (cross direction; parallel to the lateral axis of the sample) and a length of 100.0 mm along the MD (machine direction; parallel to the longitudinal axis of the sample), maintaining their orientation after they are cut and marking the body-facing surface (or the surface intended to face the body of a finished article). In like fashion, five replicate dry test specimens are prepared.

Wet test specimens are initially prepared in the exact manner as for the dry test specimen, followed by the addition of test fluid just prior to testing, as follows. The dry specimen is fully submersed in the test fluid for 60 seconds. After 60 seconds elapse, the specimen is removed from the test fluid and oriented vertically for 30 seconds to allow any excess fluid to drip off. After the wet test specimen is removed from the test fluid, it must be tested within 10 minutes. In like fashion, five replicate wet test specimens are prepared.

The universal test frame is programmed such that the moveable crosshead is set to move in a direction opposite of the stationary crosshead at a rate of 1.0 mm/s. Crosshead movement begins with the specimen 1006 lying flat and undeflected on the outer blades 1003*a* and 1003*b*, continues with the inner horizontal edge of cavity 1005 in the central blade 1002 coming into contact with the top surface of the specimen 1006, and further continues for an additional 4 mm of crosshead movement. The crosshead stops at 4 mm and then immediately returns to zero at a speed of 1.0 mm/s. Force (N) and displacement (mm) are collected at 50 Hz throughout.

Prior to loading the test specimen 1006, the outside blades 1003*a* and 1003*b* are moved towards and then past central blade 1002 until there is approximately a 3 mm clearance, C, between the inner horizontal edges of cavities 1004*a* and 1004*b* in the outside blades 1003*a* and 1003*b* and the inner horizontal edge of cavity 1005 in the central blade 1002 (see FIG. 7C). The specimen 1006 is placed within clearance such that it spans the inner horizontal edges of cavities 1004*a* and 1004*b* in the outside blades 1003*a* and 1003*b*, oriented such that the MD (short side) of the specimen is perpendicular to the horizontal edges of the blades and the body-facing surface of the specimen is facing up. Center the specimen 1006 between the outside blades 1003*a* and 1003*b*. Slowly move the outside blades 1003*a* and 1003*b* in a direction opposite of the stationary crosshead until the inner horizontal edge of cavity 1005 in the central blade 1002 touches the top surface of the specimen 1006. Start the test and continuously collect force and displacement data.

Force (N) is plotted versus displacement (mm). The maximum peak force is recorded to the nearest 0.001 N. The area under the curve from load onset up to the maximum peak force is calculated and recorded as bending energy to the nearest 0.001 N-mm. The recovery energy is calculated as the area under the curve where the force is unloaded from the maximum peak to 0.0 N and recorded as recovery energy to the nearest 0.001 N-mm. In like fashion, repeat the entire test sequence for a total of five dry test specimens and five wet test specimens.

For each test specimen type (dry and wet), the arithmetic mean of the maximum peak force among like specimens is calculated to the nearest 0.001 N and recorded as Dry Peak Load and Wet Peak load, respectively. For each test specimen type (dry and wet), the arithmetic mean of bending energy among like specimens is calculated to the nearest 0.001 N-mm and reported as Dry Bending Energy and Wet Bending Energy, respectively. For each test specimen type (dry and wet), the arithmetic mean of recovery energy among like specimens is calculated to the nearest 0.001 N-mm and reported as Dry Recovery Energy and Wet Recovery Energy, respectively.

Wet and Dry Bunched Compression Method

The bunched compression test method measures the force versus displacement behavior across five cycles of load application ("compression") and load removal ("recovery") of an absorbent article test sample that has been intentionally "bunched", using a universal constant rate of extension test frame (a suitable instrument is the MTS Alliance using TestSuite software, as available from MTS Systems Corp., Eden Prairie, MN, or equivalent) equipped with a load cell for which the forces measured are within 1% to 99% of the limit of the cell. The test is executed on dry test specimens as well as wet test specimens that are dosed with a specified amount of test fluid. The intention of this method is to mimic the deformation created in the z-plane of the crotch region of an absorbent article, or components thereof, as it is worn by the wearer during sit-stand movements. All testing is performed in a room controlled at 23° C.±3 C.° and 50%±2% relative humidity.

Figure 8:
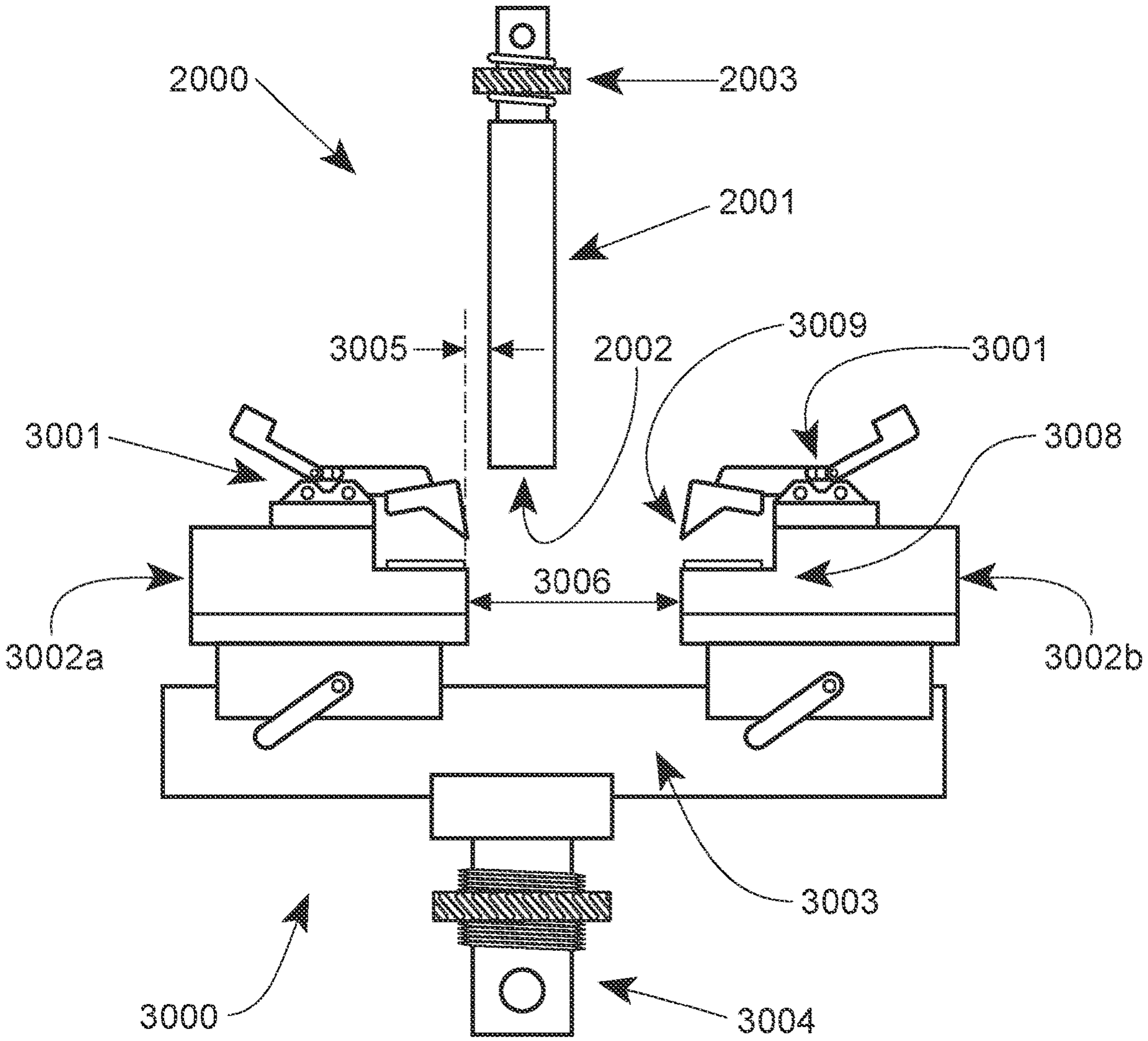
FIGS. 8, 9A, and 9B are the test method arrangement for the Wet and Dry Bunched Compression Test.
Figure 9A:
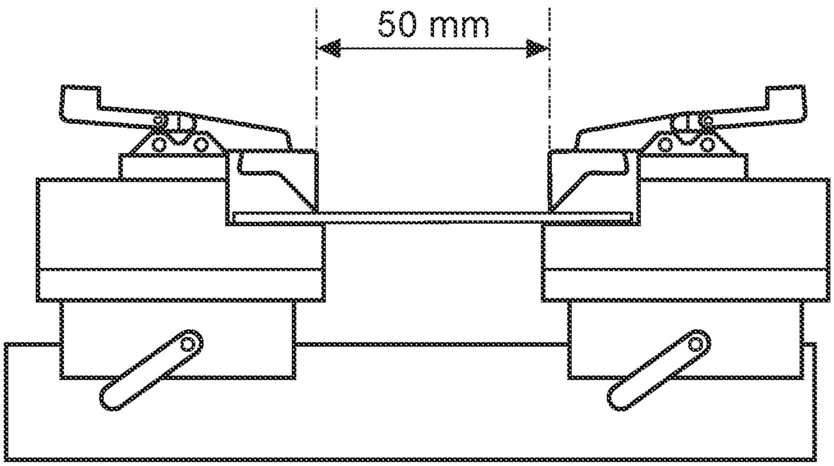
Figure 9B:
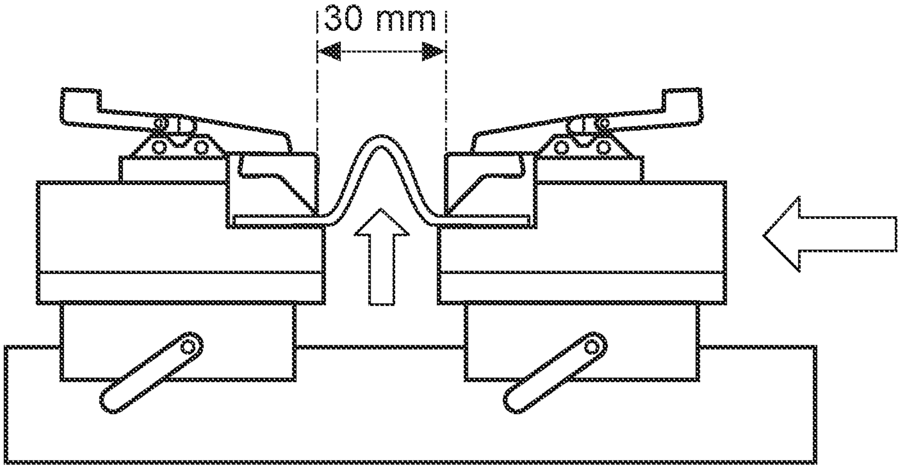

The test apparatus is depicted in FIGS. 8-9B. The bottom stationary fixture 3000 consists of two matching sample clamps 3001 each 100 mm wide, each mounted on its own movable platform 3002*a*, 3002*b*. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Test samples are conditioned at 23° C.±3 C.° and 50%±2% relative humidity for at least 2 hours before testing. Prepare the test specimen as follows. When testing an intact absorbent article, remove the release paper from any panty fastening adhesive on the garment facing side of the article, if present. Lightly apply talc powder to the adhesive to mitigate any tackiness. If there are cuffs, excise them with scissors so as not to disturb the topsheet or any other underlying layers of the article. Place the article, body facing surface up, on a benchtop. On the article, mark the intersection of the longitudinal midline and the lateral midline. Using a rectangular cutting die or equivalent cutting means, cut a specimen 100 mm in the longitudinal direction by 80 mm in the lateral direction, centered at the intersection of the midlines. When testing a material layer or layered components from an absorbent article, place the material layer or layered components on a benchtop and orient as it would be integrated into a finished article, i.e., identify the body facing surface and the lateral and longitudinal axis. Using a rectangular cutting die, or equivalent cutting means, cut a specimen 100 mm in the longitudinal direction by 80 mm in the lateral direction, centered at the intersection of the midlines. Measure the mass of the specimen and record to the nearest 0.001 grams. Calculate the basis weight of the specimen by dividing the mass (g) by the area (0.008 $m^2$) and record as basis weight to the nearest 1 g/$m^2$.

The specimen can be analyzed both wet and dry. The dry specimen requires no further preparation. The test fluid used to dose the wet test specimens is prepared by adding 100.0 grams of sodium chloride (reagent grade, any convenient source) to 900 grams of deionized water in a 1-liter Erlenmeyer flask. Agitate until the sodium chloride is completely dissolved. The wet specimen is dosed with total of 7 ml of the test solution as detailed below The liquid dose is added using a calibrated Eppendorf-type pipettor, spreading the fluid over the complete body facing surface of the specimen within a period of approximately 3 sec. The wet specimen is tested 10.0 min±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 50 Hz during all compression/decompression cycles.

Position the left platform 3002*a* 2.5 mm from the side of the upper plunger (distance 3005). Lock the left platform into place. This platform 3002*a* will remain stationary throughout the experiment. Align the right platform 3002*b* 50.0 mm from the stationary clamp (distance 3006). Raise the upper probe 2001 such that it will not interfere with loading the specimen. Open both clamps 3001. Referring to FIG. 9 A, place the dry specimen with its longitudinal edges (i.e., the 100 mm long edges) within the clamps. With the dry specimen laterally centered, securely fasten both edges in the clamps. Referring to FIG. 9B, move the right platform 3002*b* toward the stationary platform 3002*a* a distance of 20 mm so that a separation of 30.0 mm between the left and right clamps is achieved. Allow the dry specimen to bow upward as the movable platform is positioned. Now manually lower the probe 2001 until the bottom surface is approximately 1 cm above the top of the bowed specimen.

Figure 10A:
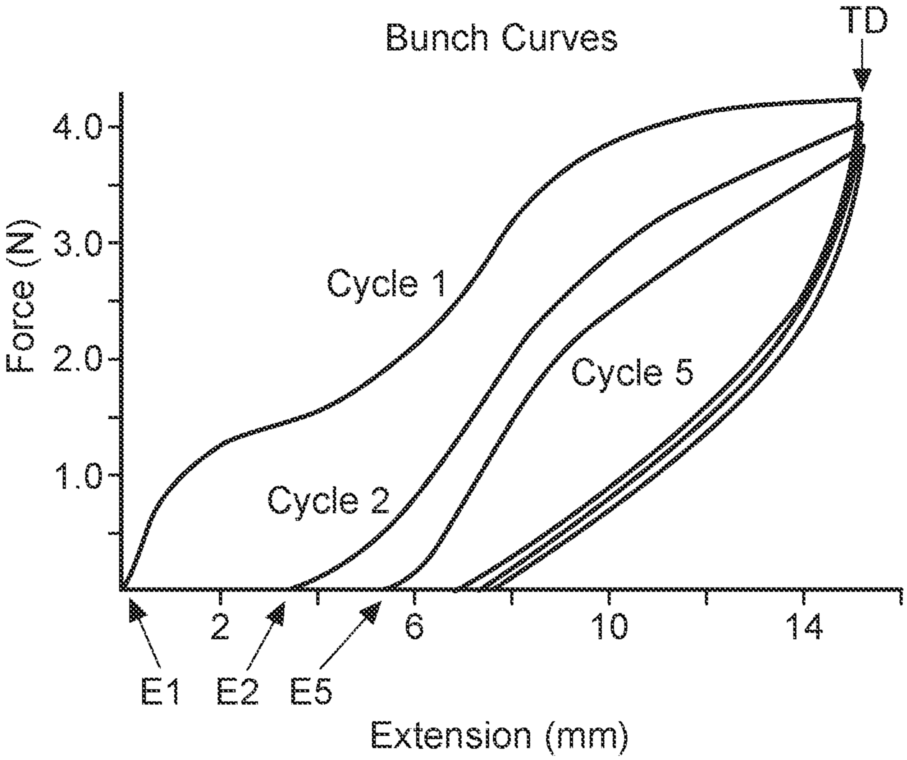
FIGS. 10A and 10B are illustrative graphs of Bunch Curves resulting from the Wet and Dry Bunched Compression Test. The graphs in FIGS. 10A and 10B are shown to illustrate how the calculations in the method may be performed and do not represent the data described herein.
Figure 10B:
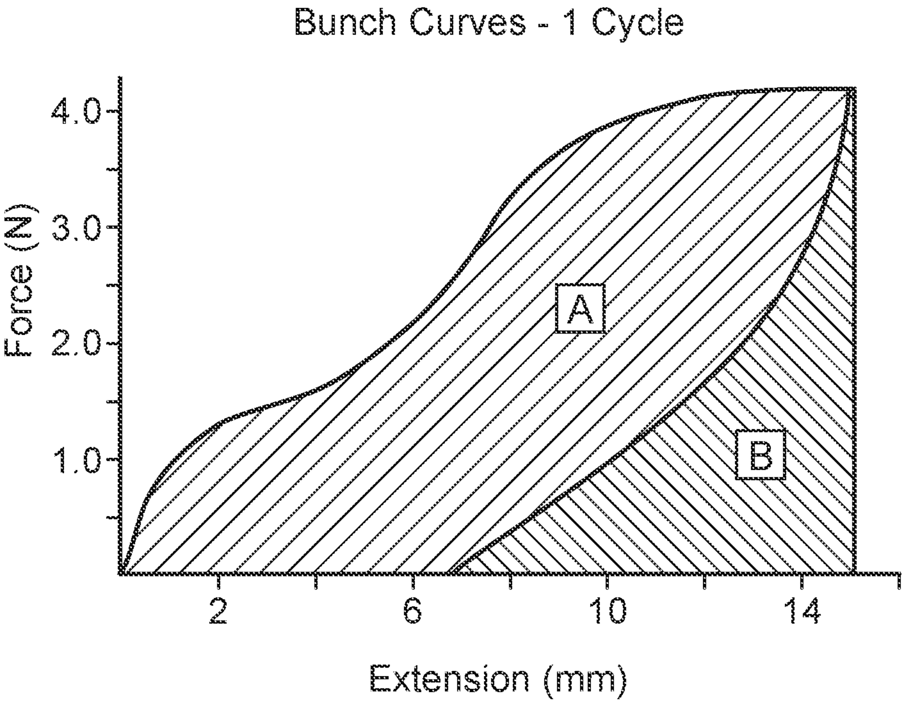

Start the test and continuously collect force (N) versus displacement (mm) data for all five cycles. Construct a graph of force (N) versus displacement (mm) separately for all cycles. A representative curve is shown in FIG. 10A. From the curve, determine the Dry Maximum Compression Force for each Cycle to the nearest 0.01 N, then multiply by 101.97 and record to the nearest 1 gram-force. Calculate the Dry % Recovery between the First and Second cycle as (TD−E2)/(TD−E1)*100 where TD is the total displacement and E2 is the extension on the second compression curve that exceeds 0.02 N, and record to the nearest 0.01%. In like fashion calculate the Dry % Recovery between the First Cycle and other cycles as (TD−E1)/(TD−E1)*100 and record to the nearest 0.01%. Referring to FIG. 10B, calculate the Dry Energy of Compression for Cycle 1 as the area under the compression curve (i.e., area A+B) and record to the nearest 0.1 N-mm. Calculate the Dry Energy Loss from Cycle 1 as the area between the compression and decompression curves (i.e., Area A) and record to the nearest 0.1 N-mm. Calculate the Dry Energy of Recovery for Cycle 1 as the area under the decompression curve (i.e., Area B) and report to the nearest 0.1 N-mm. In like fashion calculate the Dry Energy of Compression (N-mm), Dry Energy Loss (N-mm) and Dry Energy of Recovery (N-mm) for each of the other cycles and record to the nearest 0.1 N-mm. In like fashion, analyze a total of five replicate dry test specimens and report the arithmetic mean among the five dry replicates for each parameter as previously described, including basis weight.

The overall procedure is now repeated for a total of five replicate wet test specimens, reporting results for each of the five cycles as the arithmetic mean among the five wet replicates for Wet Maximum Compression Force to the nearest 1 gram-force for each cycle, Wet Energy of Compression to the nearest 0.1 N-mm for each cycle, Wet Energy Loss to the nearest 0.1 N-mm for each cycle, Wet Energy of Recovery to the nearest 0.1 N-mm for each cycle and Wet % recovery for each cycle. Of particular importance is the $5^{th}$ cycle wet energy of recovery and $5^{th}$ cycle wet % recovery properties from this test method.

CD Cyclic Elongation to 3% Strain

The cyclic tensile and recovery response of absorbent article specimens are measured for ten cycles of load application ("elongation") and load removal ("recovery") using a universal constant rate of extension test frame. The test specimen is cycled ten times to 3% engineering strain, then back to zero engineering strain. For each cycle, stiffness, peak load, normalized energy to peak, normalized recovery energy, strain at start of cycle, and strain at end of cycle (i.e., "permanent strain") are calculated and reported. The intention of this method is to understand the ability of samples to stretch in the x-y plane as a result of bodily forces, and then recover to their original state. All measurements are performed in a laboratory maintained at 23° C.±2 C.° and 50%±2% relative humidity and test specimens are conditioned in this environment for at least 2 hours prior to testing.

A suitable universal constant rate of extension test frame is the MTS Alliance interfaced to a computer running TestSuite control software (available from MTS Systems Corp, Eden Prairie, MN), or equivalent. The universal test frame is equipped with a load cell for which forces measured are within 1% to 99% of the limit of the cell. The fixtures used to grip the test specimen are lightweight (<80 grams), vise action clamps with knife or serrated edge grip faces that are at least 40 mm wide. The fixtures are installed on the universal test frame and mounted such that they are horizontally and vertically aligned with one another.

The test specimen is prepared as follows. Obtain the test material by excising it from an absorbent article, if necessary. When excising the test material, do not impart any contamination or distortion to the material layer during the process. The test specimen is cut from an area on the test material that is free of any residual of folds or wrinkles. The test specimen is as long as the lateral length of the article (parallel to the lateral axis of the article, or the intended lateral axis of the article). When excising specimens from absorbent articles of different sizes and widths, the total specimen length ($L_{total}$) may vary from product to product, thus the results will be normalized to compensate for this variation. The test specimen has a width of 25.4 mm wide (parallel to the longitudinal axis, or intended longitudinal axis of the article). Specimen width (w)=25.4 mm. Measure and record the total specimen length ($L_{total}$) to the nearest 0.1 mm. In like fashion, five replicate test specimens are prepared.

Measure the thickness (t) of the test specimen using a manually-operated micrometer equipped with a pressure foot capable of exerting a steady pressure of 0.1 psi±0.01 psi. The manually-operated micrometer is a dead-weight type instrument with readings accurate to 0.01 mm. A suitable instrument is Mitutoyo Series 543 ID-C Digimatic, available from VWR International, or equivalent. The pressure foot is a flat circular moveable face with a diameter no greater than 25.4 mm. The test specimen is supported by a horizontal flat reference platform that is larger than and parallel to the surface of the pressure foot. Zero the micrometer against the horizontal flat reference platform. Place the test specimen onto the platform, centered beneath the pressure foot. The pressure foot is lowered by hand with a descent rate of 3±1 mm/s until the full weight of the pressure is exerted onto the specimen. After 5 seconds elapse, the thickness is recorded as specimen thickness (t) to the nearest 0.01 mm.

Prepare the universal test frame as follows. Set the initial grip to grip separation distance to a nominal gage length ($L_{nominal}$) that is shorter than the total specimen length and such that the specimen can be gripped securely at both ends (i.e., $L_{nominal}<L_{total}$). Then zero the crosshead. Program the test frame to move the grips closer together by an intentional slack of 1 mm to ensure no pretension force exists on the test specimen at the onset of the test. (During this motion, the specimen will become slack between the tensile grips.) Next, the grips will move apart at a slack speed of 1 mm/s until the slack preload of 0.05 N is exceeded. At this point, the following are true. 1) The crosshead position signal (mm) is defined as the specimen slack ($L_{slack}$). 2) The initial specimen gage length (Lo) is calculated as the nominal gage length plus the slack $L_0=L_{nominal}+L_{slack}$, where units are in millimeters. 3) The crosshead extension (ΔL) is set to zero (0.0 mm). 4) The crosshead displacement (mm) is set to zero (0.0 mm). At this position the engineering strain is zero, 0.0. Engineering strain is calculated as the change in length (ΔL) divided by the initial length ($L_0$). Engineering strain=$\Delta L/L_0$. For one test cycle, the grips move apart at the initial speed of 1 mm/s until the engineering strain endpoint of 0.03 mm/mm is exceeded, immediately followed by the grips moving toward each other at the initial speed of 1 mm/s until the crosshead signal becomes less than the crosshead return position of 0 mm. The test cycle is repeated until a total of 10 cycles is complete.

The test is executed by inserting the test specimen into the grips such that the long axis of the specimen is parallel and centered with the motion of the crosshead. Start the test and continuously collect time, force and displacement data at a data acquisition rate of 100 Hz.

Construct a graph of load (N) versus displacement for all ten cycles. For each cycle, perform the following. Record peak load to the nearest 0.01 N. Calculate the energy to peak ($E_{peak}$) as the area under the load versus displacement curve from the cycle start to the strain endpoint of 0.03 mm/mm (during the loading portion of the cycle) and record to the nearest 0.01 N*mm. Calculate the return energy ($E_{return}$) as the area under the load versus displacement curve from the strain endpoint of 0.03 mm/mm to the crosshead return of 0 mm (during the unloading portion of the cycle) and record as recovery energy to the nearest 0.01 N*mm. Calculate the normalized energy to peak ($NE_{peak}$) as the energy to peak divided by the initial length, where $NE_{peak}=E_{peak}/L_0$, and record to the nearest 0.01 mN. Calculate the normalized return energy ($NE_{return}$) as the return energy divided by the initial length ($NE_{return}=E_{return}/Lo$), and record to the nearest 0.01 mN. Units of $NE_{pea}$k and $NE_{return}$ are Milli Newtons (mN).

Now construct a graph of engineering stress (σ) versus engineering strain for all ten cycles, and for each cycle perform the following. Engineering stress, in units of $N/mm^2$, is the load divided by the cross sectional area of the specimen, where the cross sectional area is the specimen width (w) multiplied by the thickness (t), σ=Load/(w*t). Determine the modulus, or slope of the stress versus strain curve for a line between the point that occurs at the minimum force and the point that occurs at the maximum force (during the loading portion of the cycle) and record as modulus to the nearest 0.01 N/mm. Calculate stiffness by multiplying the modulus by the specimen thickness and record as tensile stiffness to the nearest 0.01 N/mm. The strain of the test specimen at the beginning of the cycle is defined by the strain when the slack preload of 0.05 N is exceeded for that cycle (during the loading portion of the cycle), and is recorded as cycle initial strain to the nearest 0.01 mm/mm. The strain of the test specimen at the end of the cycle is defined by the strain when the load becomes less than the preload of 0.05 N for that cycle (during the unloading portion of the cycle), and is recorded as permanent strain to the nearest 0.01 mm/mm. In like fashion, the overall procedure is now repeated for all five replicates.

The arithmetic mean among the five replicate test specimens is calculated for each of the parameters, for each of the ten cycles, and reported as Peak Load to the nearest 0.01 N, Normalized Energy to Peak to the nearest 0.01 mN, Normalized Recovery Energy to the nearest 0.01 mN, Tensile Stiffness to the nearest 0.01 N/mm, Cycle Initial Strain to the nearest 0.01 mm/mm, and Permanent Strain to the nearest 0.01 mm/mm.

Structural Bond Sites Pattern Spacing and Area Measurement Method

The spacing between the discreet structural bond sites that are used to create a quilt-like pattern on absorbent article samples, and the overall area taken up by the sum of those elements in a specified region of the sample are measured on images of the absorbent article sample acquired using a flatbed scanner. The scanner is capable of scanning in reflectance mode at a resolution of 2400 dpi and 8 bit grayscale. A suitable scanner is an Epson Perfection V750 Pro from Epson America Inc., Long Beach CA, or equivalent. The scanner is interfaced with a computer running an image analysis program. A suitable program is ImageJ v. 1.52, National Institute of Health, USA, or equivalent. The sample images are distance calibrated against an acquired image of a ruler certified by NIST. To enable maximum contrast, the specimen is backed with an opaque, black background of uniform color prior to acquiring the image. All testing is performed in a conditioned room maintained at about 23±2° C. and about 50±2% relative humidity.

The test sample is prepared as follows. Remove the absorbent article from any wrapper present. If the article is folded, gently unfold it and smooth out any wrinkles. If wings are present, extend them but leave the release paper intact. The test samples are conditioned at about 23° C.±2 C.° and about 50%±2% relative humidity for 2 hours prior to testing.

Images are obtained as follows. The ruler is placed on the scanner bed such that it is oriented parallel to the sides of the scanner glass. An image of the ruler (the calibration image) is acquired in reflectance mode at a resolution of 2400 dpi (approximately 94 pixels per mm) and in 8-bit grayscale. The calibration image is saved as an uncompressed TIFF format file. After obtaining the calibration image, the ruler is removed from the scanner glass and the test sample is scanned under the same scanning conditions as follows. Place the test sample onto the center of the scanner glass and secure, if necessary, such that it lies flat with the body-facing surface of the sample facing the scanner's glass surface. The sample is oriented in such a way that the entire sample is within the glass surface. The black background is placed on top of the specimen, the scanner lid is closed, and a scanned image of the entire sample is acquired with the same settings as used for the calibration image. The sample image is saved as an uncompressed TIFF format file.

The sample image is analyzed as follows. Open the calibration image file in the image analysis program, and calibrate the image resolution using the imaged ruler to determine the number of pixels per millimeter. Now open the sample image in the image analysis program, and set the distance scale using the image resolution determined from the calibration image. Now visually inspect the pattern of emboss elements present on the sample in the image and identify the zones of the pattern that are to be analyzed. For example the absorbent article can be divided into three equal lengths zones in the machine direction such as the front one third zone, zone 1, the central one third zone, zone 2 and the end one third zone, zone 3 as example. Use the image analysis tools to draw a shape along the outer perimeter of the first discreet zone to be analyzed. Measure the area of this first zone and record as Zone 1 Total Area to the nearest 0.01 $mm^2$. Now measure the area of each individual, discreet emboss element that lies inside of the zone 1 perimeter as follows. Draw a minimum bounding circle around an individual emboss element such that no portion of the emboss element lies outside of the bounding circle. Now measure the area of the bounding circle for that emboss element and record the emboss element area to the nearest 0.01 $mm^2$. In like fashion, measure the area of every emboss element, including portions of emboss elements, that lie inside zone 1 and record each to the nearest 0.01 $mm^2$. Now sum the areas of all of the emboss elements inside of zone 1 and record as Zone 1 Total Emboss Element Area to the nearest 0.01 $mm^2$. Divide the Zone 1 Total Emboss Element Area by the Zone 1 Total Area then multiply by 100 and record as Zone 1% Total Area Represented by Emboss Elements. The spacing between each discreet emboss element inside of zone 1 is measured as follows. Measure the distance from the center of the minimum bounding circle drawn around a discreet emboss element inside of zone 1, as described herein, to the center of the minimum bounding circle drawn around the nearest neighboring discreet emboss element inside of zone 1, and record this distance as emboss spacing to the nearest 0.01 mm. In like fashion, repeat for all neighboring emboss elements inside of zone 1, and record each distance to the nearest 0.01 mm. Now calculate the arithmetic mean among all measured emboss spacings measured between nearest neighbors inside of zone 1, and record as Zone 1 Emboss Spacing to the nearest 0.01 mm.

In like fashion, the entire procedure is repeated for each additional zone containing emboss elements that is present on the test sample and label accordingly as Zone 2, Zone 3, etc.

Light Touch Rewet Method

Light Touch Rewet method is a quantitative measure of the mass of liquid that emerges from an absorbent article test sample that has been dosed with a specified volume of Artificial Menstrual Fluid (AMF; as described herein) when a weight is applied for a specified length of time. All measurements are performed in a laboratory maintained at 23° C.±2 C.° and 50%±2% relative humidity.

A syringe pump equipped with a disposable syringe is utilized to dose the test sample. A suitable pump is the Perfusor® Compact S (available from B. Braun), or equivalent, and must be able to accurately dispense the AMF at a rate of 42 ml/min. The disposable syringe is of ample volume (e.g., BD Plastipak 20 mL) and is connected to flexible tubing that has an inner diameter of 3/16" (e.g., Original Perfusor® Line, available from Braun, or equivalent). The AMF is prepared, as described herein, and is brought to room temperature (23° C.±2 C.°) prior to using for this test. Prior to the commencement of the measurement, the syringe is filled with AMF and the flexible tubing is primed with the liquid, and the dispensing rate (42 ml/min) and dosing volume (4.0 mL±0.05 mL) are verified according to the manufacturer's instructions. The flexible tubing is then mounted such that it is oriented vertically above the test sample, and the distance between the tip of the tubing and the surface of the test sample is 19 mm. To note, the AMF must be removed from the syringe and thoroughly mixed every 15 minutes.

The rewet weight assembly consists of an acrylic plate and a stainless steel weight. The acrylic plate has dimensions of 65 mm by 80 mm with a thickness of about 5 mm. The stainless steel weight along with the acrylic plate have a combined mass of 2 pounds (907.19 g), to impart a pressure of 0.25 psi beneath the surface of the acrylic plate.

For each test sample, five sheets of filter paper with dimensions of 4 inch by 4 inch are used as the rewet substrate. The filter paper is conditioned at 23° C.±2 C.° and 50%±2% relative humidity for at least 2 hours prior to testing. A suitable filter paper has a basis weight of about 139 gsm, a thickness of about 700 microns with an absorption rate of about 1.7 seconds, and is available from Ahlstrom- Munksjo North America LLC, Alpharetta, GA VWR International as Ahlstrom grade 989, or equivalent.

Prepare the test sample as follows. The test samples are conditioned at 23° C.±2 C.° and 50%±2% relative humidity for at least 2 hours prior to testing. Test samples are removed from all packaging using care not to press down or pull on the products while handling. Lay the test sample on a horizontally rigid flat surface and gently smooth out any folds. Determine the test location as follows. For symmetrical samples (i.e., the front of the sample is the same shape and size as the back of the sample when divided laterally along the midpoint of the longitudinal axis of the sample), the test location is the intersection of the midpoints of the longitudinal axis and lateral axis of the sample. For asymmetrical samples (i.e., the front of the sample is not the same shape and size as the back of the sample when divided laterally along the midpoint of the longitudinal axis of the sample), the test location is the intersection of the midpoint of the longitudinal axis of the sample and a lateral axis positioned at the midpoint of the sample's wings. A total of three test samples are prepared.

Place the test sample on a horizontally flat rigid surface, with the previously identified test location centered directly below the tip of the flexible tubing. Adjust the height of the tubing such that it is 19.0 mm above the surface of the test sample. Start the pump to dispense 4.0 mL±0.05 mL of AMF at a rate of 42 ml/min. As soon as the AMF has been fully dispensed, start a 10 minute timer. Now obtain the mass of 5 sheets of the filter paper and record as dry mass to the nearest 0.001 grams. When 10 minutes have elapsed, place the five sheets of pre-weighed filter papers onto the test sample, centering the stack over the dosing location. Now place the acrylic plate centered over the top of the filter papers such that the long side of the plate is parallel with the longitudinal axis of the test sample. Now carefully lower the stainless steel weight centered over the acrylic plate and immediately start a 30 second timer. After 30 seconds have elapsed, gently remove the rewet weight and acrylic plate and set aside. Obtain the mass of the five sheets of filter paper and record as wet mass to the nearest 0.001 grams. Subtract the dry mass from the wet mass of the filter papers, and record as rewet to the nearest 0.001 grams. Wipe off any residual test liquid from the bottom face of the acrylic plate prior to testing the next sample. In like fashion, repeat for a total of three replicate test samples.

The arithmetic mean of the rewet among the three replicate test samples is calculated and reported as the 'Light Touch Rewet' to the nearest 0.001 g.

Artificial Menstrual Fluid (AMF) Preparation

The Artificial Menstrual Fluid (AMF) is composed of a mixture of defibrinated sheep blood, a phosphate buffered saline solution and a mucous component. The AMF is prepared such that it has a viscosity between 7.15 to 8.65 centistokes at 23° C.

Viscosity of the AMF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and instrument is operated and calibrated as per the manufacturer. Measurements are taken at 23° C.±1 C.° and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, sterilized, available from American Laboratories, Inc., Omaha, NE, or equivalent), 10% v/v lactic acid aqueous solution, 10% w/v potassium hydroxide aqueous solution, sodium phosphate dibasic anhydrous (reagent grade), sodium chloride (reagent grade), sodium phosphate monobasic monohydrate (reagent grade) and distilled water, each available from VWR International or equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5 C°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 mL graduated cylinder, measure the volume of the entire batch of the previously prepared mucous component and add it to a 1200 mL beaker. Add an equal volume of sheep blood to the beaker and mix thoroughly. Using the viscosity method previously described, ensure the viscosity of the AMF is between 7.15-8.65 centistokes. If not the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 $C^{0}$. Any unused portion is discarded after testing is complete.

Thickness—Pressure Method

The thickness of a test specimen is measured as the distance between a reference platform on which the specimen rests and a pressure foot that exerts a specified amount of pressure onto the specimen over a specified amount of time. For purposes herein, thickness is measured and reported at two different confining pressures (7 $g/cm^2$ and 70 $g/cm^2$). All measurements are performed in a laboratory maintained at 23° C.±2 C.° and 50%±2% relative humidity and test specimens are conditioned in this environment for at least 2 hours prior to testing.

Thickness is measured with a manually-operated micrometer equipped with a pressure foot capable of exerting a steady pressure (7 $g/cm^2$ and 70 $g/cm^2$) onto the test specimen. The manually-operated micrometer is a dead-weight type instrument with readings accurate to 0.01 mm. A suitable instrument is Mitutoyo Series 543 ID-C Digimatic, available from VWR International, or equivalent. The pressure foot is a flat ground circular movable face with a diameter that is smaller than the test specimen and capable of exerting the required pressure. A suitable pressure foot has a diameter of 25.4 mm, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen by removing it from an absorbent article, if necessary. When excising the test specimen from an absorbent article, use care to not impart any contamination or distortion to the test specimen layer during the process. The test specimen is obtained from an area free of folds or wrinkles, and it must be larger than the pressure foot.

To measure thickness at a confining pressure of 7 $g/cm^2$, first zero the micrometer against the horizontal flat reference platform. Place the test specimen on the platform with the test location centered below the pressure foot. Gently lower the pressure foot with a descent rate of 3.0 mm±1.0 mm per second until the full pressure is exerted onto the test specimen. Wait 5 seconds and then record the thickness of the test specimen to the nearest 0.01 mm. In like fashion, repeat for a total of ten replicate test specimens. Calculate the arithmetic mean for all thickness measurements obtained at a confining pressure of 7 $g/cm^2$ and report as Thickness at 7 $g/cm^2$ to the nearest 0.01 mm.

To measure thickness at a confining pressure of 70 $g/cm^2$, first zero the micrometer against the horizontal flat reference platform. Place the test specimen on the platform with the test location centered below the pressure foot. Gently lower the pressure foot with a descent rate of 3.0 mm±1.0 mm per second until the full pressure is exerted onto the test specimen. Wait 5 seconds and then record the thickness of the test specimen to the nearest 0.01 mm. In like fashion, repeat for a total of ten replicate test specimens. Calculate the arithmetic mean for all thickness measurements obtained at a confining pressure of 70 $g/cm^2$ and report as Thickness at 70 $g/cm^2$ to the nearest 0.01 mm.

Pore Volume Distribution (PVD) Method

Pore Volume Distribution determines the estimated porosity of the effective pores within a porous test specimen by measuring the fluid movement into and out of said specimen as stepped, controlled differential pressure is applied to the specimen in a sample chamber. The incremental and cumulative quantity of fluid that is thereby absorbed/drained by the porous specimen at each pressure is then determined. In turn, work done by the porous specimen normalized by the area of said specimen is calculated as Capillary Work Potential.

Method Principle

For uniform cylindrical pores, the radius of a pore is related to the differential pressure required to fill or empty the pore by the following equation $$\text{Differential Pressure}=[2\gamma \cos \Theta)]/r$$

where γ=liquid surface tension, Θ=contact angle, and r=pore radius.

Pores contained in natural and manufactured porous materials are often thought of in terms such as voids, holes or conduits, and these pores are generally not perfectly cylindrical nor all uniform. One can nonetheless use the above equation to relate differential pressure to an effective pore radius, and by monitoring liquid movement into or out of the material as a function of differential pressure, characterize the effective pore radius distribution in said porous material. (Because nonuniform pores are approximated as uniform by the use of an effective pore radius, this general methodology may not produce results precisely in agreement with measurements of void dimensions obtained by other methods such as microscopy.)

The Pore Volume Distribution Method uses the above principle and is reduced to practice using the apparatus and approach described in "Liquid Porosimetry: New Methodologies and Applications" by B. Miller and I. Tyomkin published in The Journal of Colloid and Interface Science (1994), volume 162, pages 163-170, incorporated herein by reference. This method relies on measuring the increment of liquid volume that enters or leaves a porous specimen as the differential air pressure is changed between ambient ("lab") air pressure and a slightly elevated air pressure (positive differential pressure) surrounding the specimen in a sample test chamber. The specimen is introduced to the sample chamber dry, and the sample chamber is controlled at a positive differential pressure (relative to the lab) sufficient to prevent fluid uptake into the specimen after the fluid bridge is opened. After opening the fluid bridge, the differential air pressure is decreased in steps to 0, and in this process subpopulations of pores within the specimen acquire liquid according to their effective pore radius. After reaching a minimal differential pressure at which the mass of fluid within the specimen is at a maximum, differential pressure is increased stepwise again toward the starting pressure, and the liquid is drained from the specimen. The absorption portion of the stepped sequence begins at the maximum differential pressure (smallest corresponding effective pore radius) and ends at the minimum differential pressure (largest corresponding effective pore radius). The drainage portion of the sequence begins at the minimum pressure differential and ends at the maximum pressure differential. After correcting for any fluid movement for each particular pressure step measured on the chamber while empty for the entire absorption/drainage sequence, the fluid uptake by the specimen (mg) as well as cumulative volume ($mm^3/mg$) at each differential pressure is determined in this method.

Specimen Conditioning and Preparation

The Pore Volume Distribution Method is conducted on specimens obtained from material samples that have been conditioned for at least 2 hours in a room maintained at a temperature of 23° C.±2.0° C. and a relative humidity of 50%±2%, and all tests are conducted under the same environmental conditions in such conditioned room. A specimen conditioned as described herein is considered dry for purposes of this invention. Obtain the test material by excising it from an absorbent article, if necessary. When excising the test material, do not impart any contamination or distortion to the material layer during the process. The test specimen is cut from an area on the test material that is free of any folds or wrinkles. Determine which side of the test material is intended to face the wearer in use, then cut a specimen that is 55 mm long by 55 mm wide. Measure the mass of the specimen and record to the nearest 0.1 mg. Three specimens are prepared and measured for any given test material being evaluated, and the results from those three replicates are averaged to give the final reported values.

Apparatus

Apparatus suitable for this method is described in "Liquid Porosimetry: New Methodology and Applications" by B. Miller and I. Tyomkin published in The Journal of Colloid and Interface Science (1994), volume 162, pages 163-170. Further, any pressure control scheme capable of controlling the sample chamber pressure between 0 mm $H_20$ and 1098 mm $H_20$ differential pressure may be used in place of the pressure-control subsystem described in this reference. One example of a suitable overall instrumentation and software is the TRI/Autoporosimeter (Textile Research Institute (TRI)/Princeton Inc. of Princeton, NJ, USA). The TRI/Autoporosimeter is an automated computer-controlled instrument for measuring pore volume distributions in porous materials (e.g. the volumes of different size pores within the range from 5 μm to 1200 μm effective pore radii). Computer programs such as Automated Instrument Software Releases 2000.1 or 2003.1/2005.1 or 2006.2; or Data Treatment Software Release 2000.1 (available from TRI Princeton Inc.), and spreadsheet programs may be used to capture and analyze the measured data.

Figure 11:
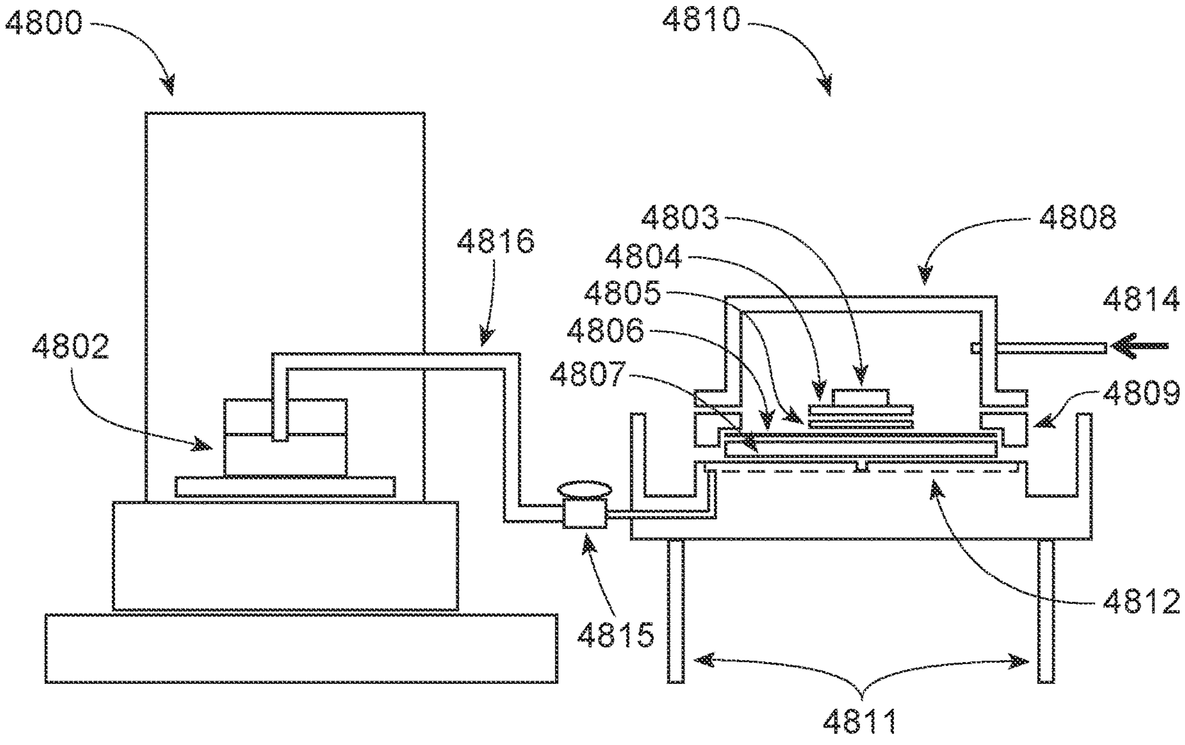
FIG. 11 is a test method arrangement for the Pore Volume Distribution Method.

A schematic depiction of suitable equipment is shown in FIG. 11. The equipment consists of a balance 4800 with fluid reservoir 4802 which is in direct fluid communication with the specimen 4805 which resides in a sealed, air-pressurized sample chamber 4810. The fluid communication between the reservoir 4802 and the sample chamber 4810 is controlled by valve 4815. A weight 4803 placed on top of a Plexiglass plate 4804 (55 mm long by 55 mm wide) is used to apply a confining pressure of 0.25 psi on the test specimen to ensure good contact between the specimen and a fluid saturated membrane 4806 throughout the test. The membrane 4806 (90 mm diameter, 150 um thick, 1.2 μm pore size; mixed cellulose ester filter RAWP09024; available from Millipore Corporation of Bedford, MA) is attached to a macro-porous frit 4807 (Monel plate with 90 mm diameter, 60 mm thick; available from Mott Corporation, Farmington, CT, or equivalent) as follows. Adhere the membrane 4806 to the frit 4807 using Krylon® spray paint (Gloss White Spray Paint #1501; available from FilmTools, or equivalent) as the adhesive. Allow the prepared membrane/frit assembly to dry prior to use.

To prepare the equipment for testing, fill the inner base 4812 of the sample chamber 4810 with test fluid. The test fluid is degassed 0.9% saline solution, prepared by adding 9.0 g of reagent grade NaCl per 1 L of deionized water (liquid density is 1.01 g/cm$^3$, surface tension $\gamma$ to be 72.3±1 mN/m, contact angle cos $\Theta$=0.37). Place the membrane/frit assembly, membrane 4806 side up, onto the inner base 4812 of the sample chamber 4810, and secure it into place with a locking collar 4809. Fill the reservoir 4802 and connecting tube 4816 with test fluid. Open valve 4815 and ensure that no air bubbles are trapped within the connecting tube or the pores within the membrane/frit assembly. Using the legs 4811 of the sample chamber 4810, level the sample chamber and adjust the height of the sample chamber (and/or the amount of fluid in the reservoir 4802) as necessary, to bring the top surface of the membrane 4806 into the same horizontal plane as the top surface of the fluid in the reservoir 4802.

Program the system to progress through a sequence of stepped differential pressures (in mm $H_20$) as follows: 1098, 549, 366, 275, 220, 183, 137, 110, 92, 78, 69, 61, 55, 50, 46, 42, 39, 37, 34, 32, 31, 29, 27, 24, 22, 20, 18, 14, 9.2, 6.9, 5.5, 4.6, 5.5, 6.9, 9.2, 14, 18, 20, 22, 24, 27, 29, 31, 32, 34, 37, 39, 42, 46, 50, 55, 61, 69, 78, 92, 110, 137, 183, 220, 275, 366, 549, 1098. These pressures correlate to effective pore radii from 5 μm (1098 mm $H_20$) to 1200 μm (4.6 mm $H_20$). The criterion for moving from one pressure step to the next is that fluid uptake/drainage to/from the specimen, measured at the balance 4800, is less than 10 mg/min for 15 seconds.

Method Procedure

Check the system for leaks and ensure the maximum test pressure can be reached as follows. With liquid valve 4815 open, place the top 4808 of the sample chamber 4810 in place and seal the chamber. Apply sufficient air pressure to the chamber 4810 (via connection 4814) to achieve a differential pressure of 1098 mm $H_2O$ (5 μm effective pore radius). Close the liquid valve 4815 then open the sample chamber. Place the specimen 4805 (wearer side facing down) directly onto the membrane 4806, then place the cover plate 4804 and confining weight 4803 centered over the specimen. Replace the top 4808 and reseal the sample chamber 4810. Open the liquid valve 4815 to allow movement of fluid between the liquid reservoir 4802 and the specimen and start the test to progress through the pre-specified sequence of differential pressures. The amount of fluid absorbed (or drained) by the specimen at each pressure step over the entire sequence is recorded as Uptake to the nearest 0.1 mg.

A separate "blank" measurement is performed by following this same method procedure (same stepped sequence of differential pressures) on an empty sample chamber with no specimen 4805, cover plate 4804 or confining weight 4803 present on the membrane/frit assembly. Any fluid movement observed is recorded (mg) at each of the pressure steps. Fluid uptake data for the specimen are corrected for any fluid movement associated with the empty sample chamber by subtracting fluid uptake values of this "blank" measurement from corresponding values in the measurement of the specimen, and recorded as Blank Corrected Specimen Uptake to the nearest 0.1 mg.

Determination of % Saturation, Cumulative Volume and Capillary Work Potential

The % Saturation of the specimen at each of the pressure steps for both the absorption and drainage portions of the test sequence can be calculated by dividing the maximum Blank Corrected Specimen Uptake (mg) by the Blank Corrected Specimen Uptake (mg), then multiplying by 100. The cumulative volume is calculated for each of the pressure steps by the following equation $$\text{Cumulative Volume (mm}^3\text{/mg)}=\text{Blank Corrected Specimen Uptake (mg)/Fluid Density (g/cm}^3\text{)/Mass of Specimen (mg)}$$

The Capillary Work Potential (CWP) is the work done by the specimen normalized by the area of the specimen for the absorption portion of the test sequence. The trapezoidal rule is used to integrate the ith Pressure as a function of Cumulative Volume over n data points for the absorption portion of the cycle.

$$CWP\left[\frac{\text{mJ}}{\text{m}^2}\right]=\frac{W}{A_w}=\sum_{i=1}^{n}\frac{1}{2}\frac{m_w(CV_{i+1}-CV_i)(P_i+P_{i+1})}{A_w}\left(10^3\left[\frac{\text{mJ}}{\text{J}}\right]\right)$$

where $m_w$=mass of specimen (mg)

CV=Cumulative Volume ($m^3$/mg)

P=Air Pressure (Pa)

$A_w$=Area of the specimen ($m^2$)

Record the CWP to the nearest 1 mJ/$m^2$. In like fashion, repeat the measure on a total of three (3) replicate test specimens. The arithmetic mean of CWP among the three replicate test specimens is calculated and reported as CWP to the nearest 1 mJ/$m^2$.

Wet Penetration Time Method

Wet Penetration Time measurements are executed using a sessile drop experiment. A specified volume of Paper Industry Fluid (PIF; preparation provided separately herein) is applied to the surface of a test specimen using an automated liquid delivery system. A high speed video camera captures time-stamped images of the drop at a rate of 125 frames per second. The time lapse between the time at which the drop first contacts the surface of the test specimen until the drop has fully absorbed into the test specimen is measured. The wet penetration time is determined as the time it takes the contact angle of a drop absorbing into the test specimen to decrease to a contact angle <10°. The contact angle between the drop and the surface of the test specimen is determined by image analysis software. All measurements are performed at constant temperature (23° C.±2 C.°) and relative humidity (50%±2%).

An automated contact angle tester is required to perform this test. The system includes a light source, a video camera, a horizontal specimen stage, a liquid delivery system with a pump and micro syringe and a computer equipped with software suitable for video image capture, image analysis and reporting contact angle data. A suitable instrument is the Optical Contact Angle Measuring System OCA 20 (DataPhysics Instruments, Germany), or equivalent. The system must be able to deliver a 35 microliter drop and be capable of capturing images at a rate of 125 frames per second. The system is calibrated and operated per the manufacturer's instructions, unless explicitly stated otherwise in this testing procedure.

Specimen Preparation

To obtain a test specimen for measurement, lay a single layer of the dry substrate material out flat and cut a rectangular test sample 15 mm in width and about 70 mm in length. The width of the specimen may be reduced as necessary to ensure that the test region of interest is not obscured by surrounding features during testing. With a narrower specimen strip, care must be taken so that the liquid drop does not reach the edge of the test specimen during testing, otherwise the test must be repeated. Care should be taken to avoid folds, wrinkles or tears when selecting a location for sampling. If the substrate material is a layer of an absorbent article, for example a topsheet or outer cover nonwoven material, acquisition layer, distribution layer, or other component layer; tape the absorbent article to a rigid flat surface in a planar configuration. Carefully separate the individual substrate layer from the absorbent article. A scalpel and/or cryogenic spray (such as Cyto-Freeze, Control Company, Houston Tex.) may be used to remove a substrate layer from additional underlying layers, if necessary, to avoid any longitudinal and lateral extension of the material. Once the substrate layer has been removed from the absorbent article, proceed with cutting the test specimen as previously described. Precondition the test specimen at 23° C.±2 C.° and 50%±2% relative humidity for 2 hours prior to testing.

Testing Procedure

The test specimen is positioned onto the horizontal specimen stage with the test region in the camera's field of view beneath the liquid delivery system needle, with the test side (wearer-facing side) facing up. The test specimen is secured in such a way that it lies flat but unstrained, and any interaction between the liquid drop and the underlying surface is avoided to prevent undue capillary forces. A 14 gauge blunt tip stainless steel needle (ID 1.600 mm, OD 1.820 mm; available from IntelliSpense, or equivalent) is positioned above the test specimen with at least 2 mm of the needle tip in the camera's field of view. Adjust the specimen stage to achieve a distance of about 7 mm between the tip of the needle and the surface of the test specimen. A 35 microliter drop of PIF is formed at a rate of 1 microliter per second and allowed to freely fall onto the surface of the test specimen. Video image capture is initiated prior to the drop contacting the surface of the test specimen, and subsequently a continual series of images is collected until the drop of PIF has fully absorbed into the test specimen for a duration of up to 60 seconds after the drop contacts the surface of the test specimen. Repeat this procedure for a total of five (5) substantially similar replicate test regions. Use a fresh test specimen or ensure that the previous drop's wetted area is avoided during subsequent measurements. On each of the images captured by the video camera, the test specimen surface and the contour of the drop is identified and used by the image analysis software to calculate the Contact Angle to the nearest 0.1 degree. The Contact Angle is the angle formed by the surface of the test specimen and the tangent to the surface of the liquid drop in contact with the test specimen. For each series of images from a test, time zero is the time at which the liquid drop makes contact with the surface of the test specimen Wet Penetration Time is defined as the time it takes the contact angle of a drop absorbing into the test specimen to decrease to a contact angle <10°. Wet Penetration Time is measured by identifying the first image of a given series where the contact angle has decreased to a contact angle <10°, and then based on that image, calculating and reporting the length of time that has elapsed from time zero. Wet Penetration Time is reported as 60 seconds if a contact angle less than 10° is not reached within 60 seconds. In like fashion, determine the wet penetration time for each of the five replicate test regions. Calculate the arithmetic mean of the Wet Penetration Time across the five replicate test regions, and report this value to the nearest 0.1 milliseconds.

Paper Industry Fluid (PIF) Preparation

Paper Industry Fluid (PIF) is a widely accepted nonhazardous, non-blood based surrogate fluid for human menses. PIF is an aqueous mixture composed of sodium chloride, carboxymethyl cellulose, glycerol and sodium bicarbonate, and the surface tension is adjusted with the addition of a nonionic surfactant. This standard test fluid was developed by the technical committee of the French industry group of producers of sanitary products (Groupment Francaise de producteurs d'articles pour usage sanitaires et domestiques) and described in the AFNOR standard Normilizationfrancaise Q34-018 of September 1994. When properly prepared, PIF has a viscosity of 11±1 centipoise, a surface tension of 50±2 mN/m and a pH value of 8±1 at a temperature of 23° C.±1 C°.

Viscosity of the prepared PIF is performed using a low viscosity rotary viscometer (a suitable instrument is the Cannon LV-2020 Rotary Viscometer with UL adapter, Cannon Instrument Co., State College, PA, or equivalent). The appropriate size spindle for the viscosity range is selected, and the instrument is operated and calibrated as per the manufacturer's instructions. Measurements are taken at 23° C.±1 C.° and at 30 rpm. Results are reported to the nearest 0.1 centipoise.

Surface tension of the prepared PIF is performed using a tensiometer. A suitable instrument is the Kruss K100 with a plate method (available from Kruss GmbH, Hamburg, Germany), or equivalent. The instrument is operated and calibrated as per the manufacturer's instructions. Measurements are taken when the aqueous mixture is at a temperature of 23° C.±1 C°. Results are reported to the nearest 0.1 mN/m.

Reagents needed for the PIF preparation include: sodium chloride (reagent grade solid), carboxymethyl cellulose (>98% purity, mass fraction), glycerol (reagent grade liquid), sodium bicarbonate (reagent grade solid), a 0.25% wt aqueous solution of polyethylene glycol tert-octylphenyl ether (Triton™ X-100; reagent grade) and deionized water, each reagent available from VWR International or equivalent source.

The following preparation steps will result in about 1 liter of PIF. Add 80.0±0.01 g of glycerol to a 2 L glass beaker. The amount of carboxymethyl cellulose (CMC) directly affects the final viscosity of the prepared PIF, so the amount of CMC is adjusted to yield a final viscosity within the target range (11±1 centipoise). Carboxymethyl cellulose is slowly added to the beaker of glycerol (in an amount between 15-20 grams) while stirring to minimize clumping. Continue stirring for about 30 minutes or until all of the CMC has dissolved and no clumps remain. Now add 1000±1 g of deionized water to the beaker and continue to stir. Next add 10.0±0.01 g of sodium chloride and 4.0±0.01 g of sodium bicarbonate to the beaker while stirring. The amount of nonionic surfactant solution (0.25% wt Triton™ X-100 aqueous) directly affects the final surface tension of the prepared PIF, so the amount of 0.25% wt Triton™ X-100 is adjusted to yield a final surface tension within the target range (50±2 mN/m). The total amount of 0.25% wt Triton X-100 solution to add to the beaker is around 3.7 mL.

Ensure the temperature of the prepared PIF is at 23° C.±1 C°. Using the viscosity and surface tension methods previously described, ensure the viscosity is 11±1 centipoise and the surface tension is 50±2 mN/m. Measure the pH of the prepared PIF using pH strips or a pH meter (any convenient source) and ensure the pH is within the target range (8±1). If the prepared batch of PIF does not meet the specified targets, it is disposed and another batch is made adjusting the amounts of CMC and 0.25% wt Triton™ X-100 solution as appropriate.

The qualified batch of PIF is stored covered at 23° C.±1 C°. The viscosity, surface tension and pH are tested daily prior to use to ensure the mixture meets the specified targets for each parameter.

Permeability Measurement Method

This method enables calculation of permeability of a material (in Darcys) via measurement of the downward movement of test fluid through a test specimen along the z-direction (plumb direction), over a range of falling hydrohead indicated by decreasing height of a test fluid in a vessel. The decreasing height of the test fluid inside the vessel, as the fluid drains from the bottom of the vessel through the test specimen, is iteratively measured over time during the procedure. From the collected data together with relevant dimensions of portions of the apparatus through which the fluid moves, the measured wet caliper of the test specimen, and constants associated with gravity and properties of the test fluid chosen, flow rate and permeability may be calculated. All measurements are performed in a laboratory maintained at 23° C.±2 C.° and 50%±2% relative humidity and test specimens are conditioned in this environment for at least 2 hours prior to testing.

Apparatus Components

Figure 12A:
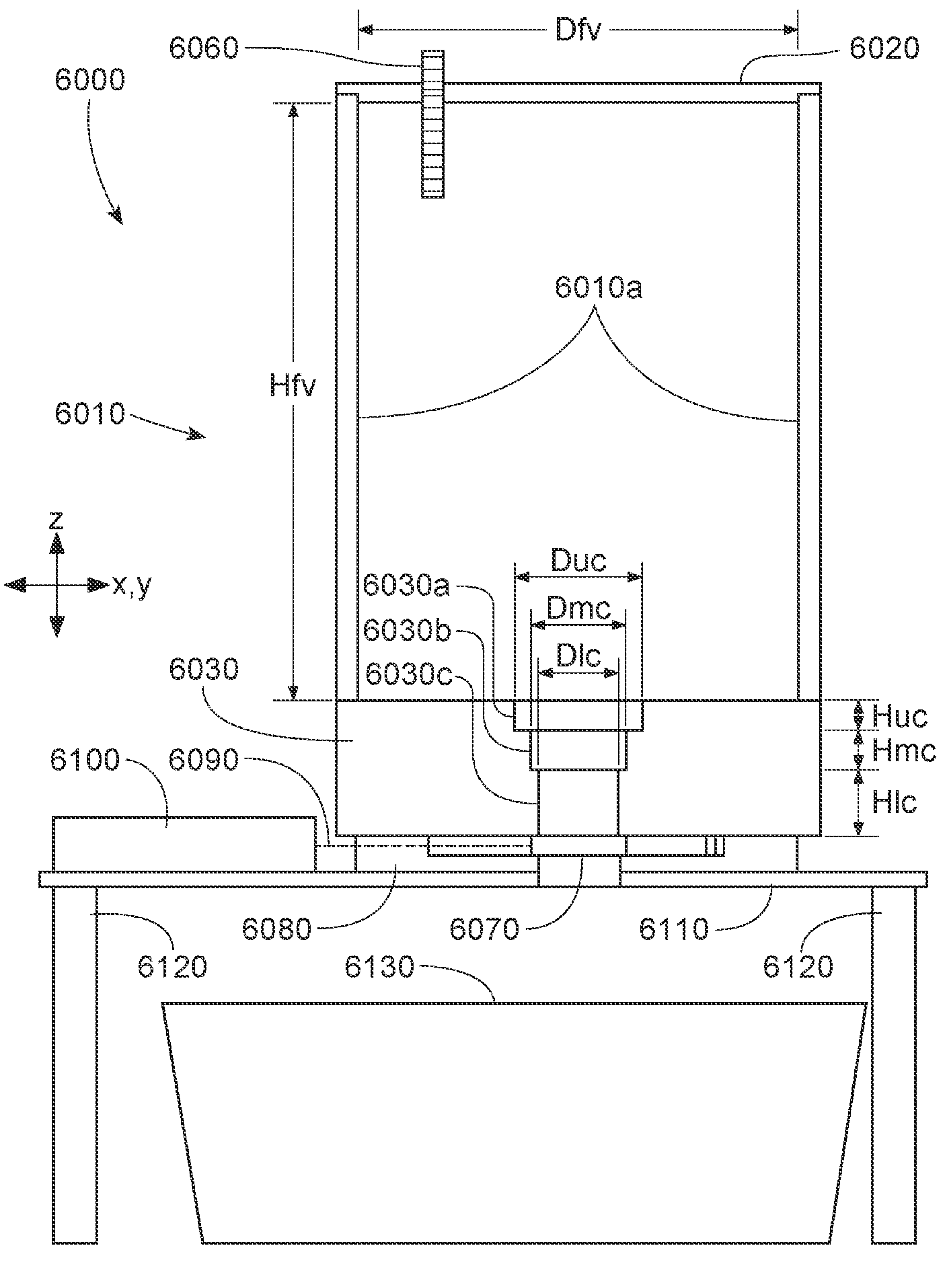
FIG. 12A is a schematic cross section of a measurement apparatus configuration used in the Permeability Measurement Method described herein, taken through a vertical plane that bisects the depicted fluid vessel 6010.

The measurement apparatus 6000 and its components are depicted in FIGS. 12A through 14. Referring to FIG. 12A, the apparatus 6000 includes a cylindrical fluid vessel 6010 including a cylindrical wall 6010*a* with a fitted lid 6020 and a base 6030 that is sealingly fitted to the bottom of the wall 6010*a* to form fluid vessel 6010; a fluid height sensor 6060 fitted in and through lid 6020; a valve 6070 housed in a valve body 6080, and a valve actuator 6100 mechanically associated with the valve via a linkage 6090.

The cylindrical wall has an inside height to the bottom of the lid, Hfv, of 200 mm, an inside diameter of 3⅞ inches (98.425 mm), a wall thickness of ⅜ inch (9.525 mm), and an outer diameter of 4⅝ inches (117.48 mm). The lid 6020 is suitably fitted to rest stably on top of the cylindrical wall, but it should not be sealingly fitted thereon; one or more vent holes (not shown) are drilled therethrough to prevent development of negative pressure/vacuum within the fluid vessel as test fluid drains therefrom. The purpose of the lid 6020 is to hold and suspend fluid height sensor 6060 over the test fluid surface, not to seal the vessel at the top.

Still referring to FIG. 12A, the base 6030 has planar, parallel upper and lower surfaces and the upper surface is sealingly affixed to the bottom of the wall 6010*a*. Base 6030 is suitably formed or machined to define therewithin a sample chamber having a cylindrical upper chamber portion 6030*a*, a cylindrical middle chamber portion 6030*b*, and a cylindrical lower chamber portion 6030*c*. The three cylindrical chamber portions are coaxial along the vertical/z-direction.

The heights and inner diameters of the three chamber portions are as follows:

- Upper chamber portion 6030*a* height Huc: 9.5 mm;
- Upper chamber portion 6030*a* inner diameter Duc: 40 mm;
- Middle chamber portion 6030*b* height Hmc: 12.5 mm;
- Middle chamber portion 6030*b* inner diameter Dmc: 30 mm;
- Lower chamber portion 6030*c* height Hlc: 20 mm; and
- Lower chamber portion 6030*a* inner diameter Dlc: 26 mm.

Valve body 6080 with valve 6070 are mounted to the underside of base 6030, beneath the lower open end of lower chamber 6030*c*. Valve 6070 is configured to be rapidly actuated between fully closed and fully open positions, wherein in the open position, the entirety of lower chamber portion 6030*c* is open to allow fluid to move freely downwardly therefrom without any restriction by valve 6070. Valve 6070 may be a flat horizontally sliding member, having a circular opening port therethrough, of a diameter of at least 26.0 mm, that is linearly moved to position beneath lower chamber portion 6030*c* upon actuation to the opened position. Alternatively, valve 6070 and valve body 6080 may have any other suitable configuration adapted to move rapidly between fully closed and fully open positions, wherein when in the fully open position the valve does not present any obstruction to fluid flow downwardly and out from the lower open end of lower chamber portion 6030*c*. Valve 6070 and actuator 6100 are configured to effect actuation from a fully closed to a fully open position, and vice versa, within no greater than 10 milliseconds for either movement. Actuator 6100 may include a solenoid or any other suitable mechanism adapted for this purpose.

Cylindrical wall 6010*a*, lid 6020, base 6030, and optionally valve body 6080 and valve 6070, are fabricated of and machined from polished, clear cast acrylic plastic (poly (methyl methacrylate) (PMMA)) stock (known brands include but are not limited to PLEXIGLAS and LUCITE), which may be obtained in various pre-cast tube, rod/bar, disc, sheet and block forms from various suppliers of such materials, such as McMaster-Carr Supply Company (Elmhurst, Illinois). For tube stock used to form wall 6010*a*, tube stock of an inner diameter Dfv varying slightly from that specified herein may be selected, according to availability; in such event, it will be recognized that the corresponding value for the radius r of the fluid vessel, in the equations below, is to be changed to reflect the actual diameter Dfv of the tube stock used.

Fluid height sensor 6060 is an ultrasonic height sensor, such as an ML Series part #098-10060, a continuous transmitter through air with an accuracy of about +0.2 mm (TE Connectivity, Schaffhausen, Switzerland and Berwyn, Pennsylvania, USA) or equivalent, interfaced to a computer running software capable of collecting fluid height versus time data throughout the test at a rate of 100 Hz. The fluid height sensor 6060 continuously transmits a signal indicating the height of the test fluid within the fluid vessel 6010 during the measurement procedure.

The apparatus further includes a support structure, which may include a support platform 6110 and height-adjustable legs 6120, or any other suitable support structure, configured to stably hold the vessel and valve assembly over a collection vessel 6130, with the longitudinal axis of cylindrical wall 6010*a* vertical/plumb and bottom of base 6030 level. Where included, a support platform 6110 must include an opening or otherwise be configured so as not to obstruct the lower end of lower chamber portion 6030*c* or the fluid exit from valve and valve body 6070, 6080.

The measurement apparatus further includes a collection vessel 6130, of any suitable shape, size and material composition suitable to receive and stably contain the entirety of the volume of test fluid that is used in this method, and fit easily beneath the support structure.

Figure 13A:
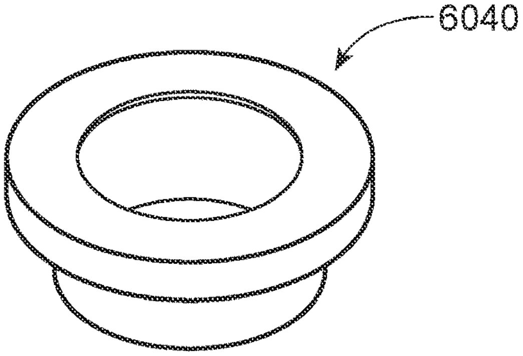
FIG. 13A is a perspective view of a sample weight used in the Permeability Measurement Method described herein.
Figure 13B:
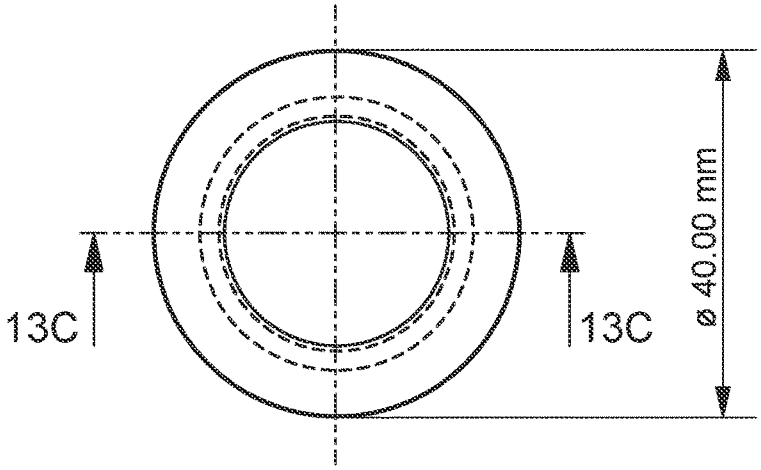
FIG. 13B is a top view of the sample weight depicted in FIG. 13*a*.
Figure 13C:
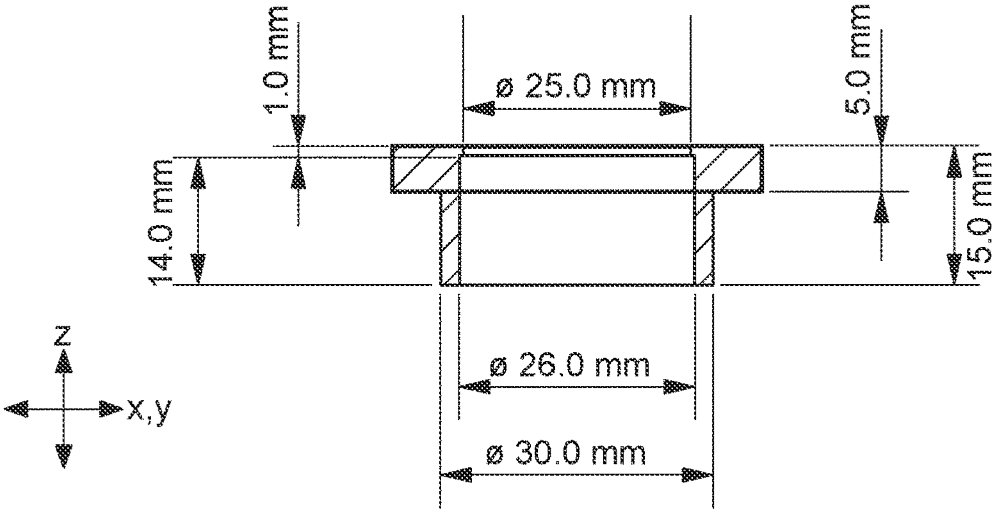
FIG. 13C is a vertical cross section view of the sample weight depicted in FIG. 13*a*.

The measurement apparatus further includes a sample weight 6040, which is machined of stainless steel to the configuration and dimensions shown in FIGS. 13A-13C.

Figure 14:
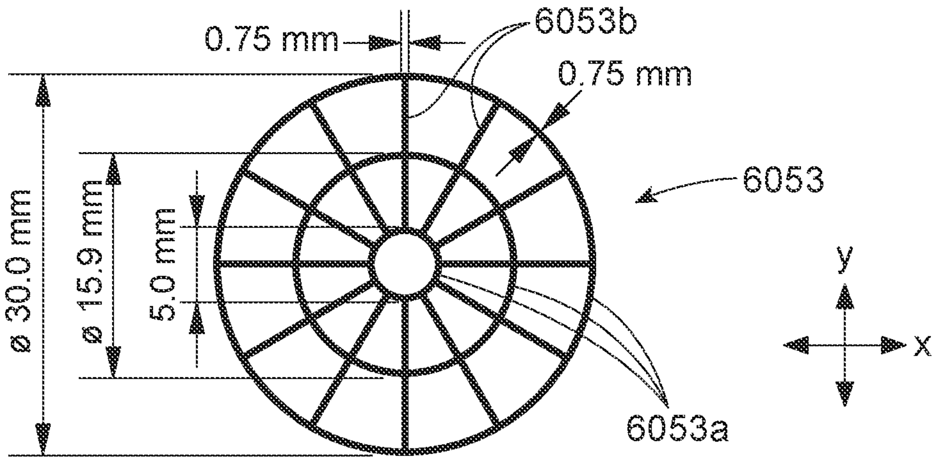
FIG. 14 is a top view of a sample support used in the Permeability Measurement Method described herein.
Figure 15:
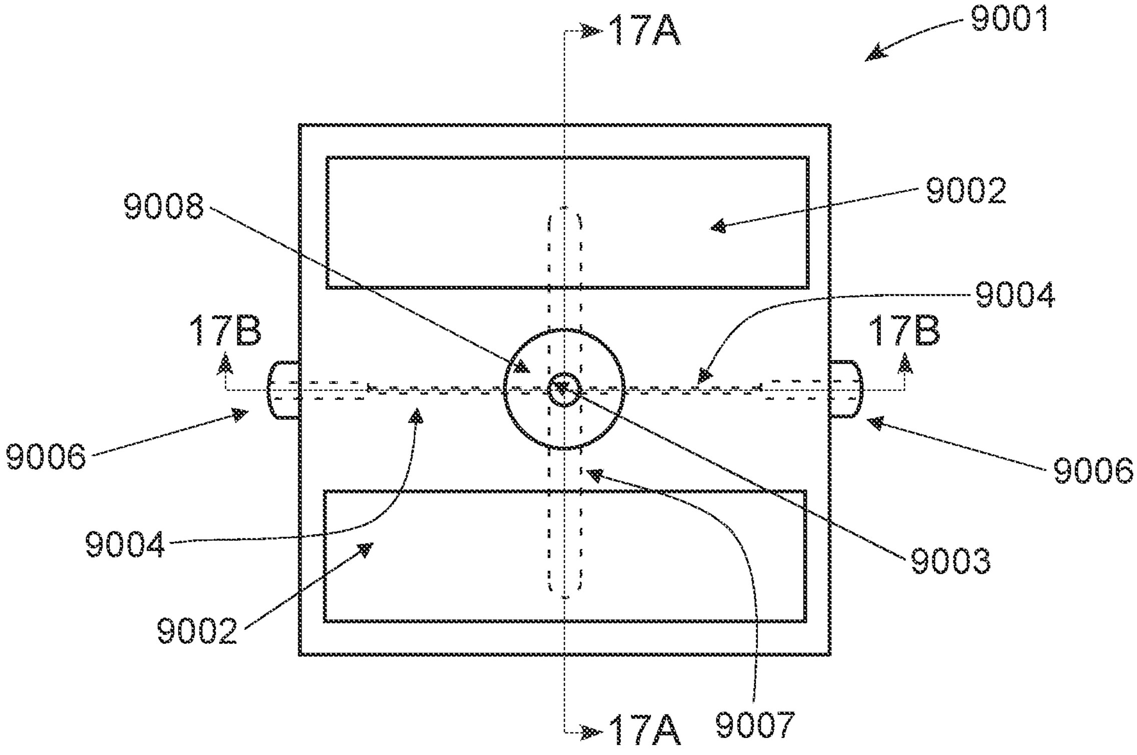
FIG. 15 is a top view of a strikethrough plate used in the Acquisition Time and Rewet Method described herein
Figure 16:
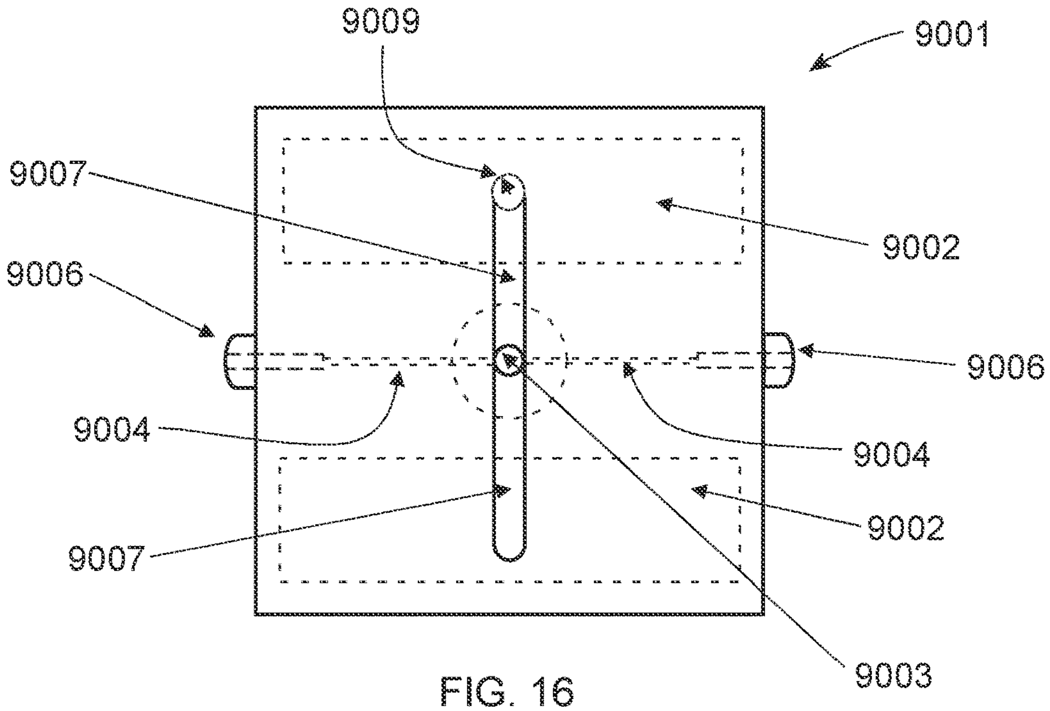
FIG. 16 is a bottom view of the strikethrough plate used in the Acquisition Time and Rewet Method described herein.
Figure 17A:
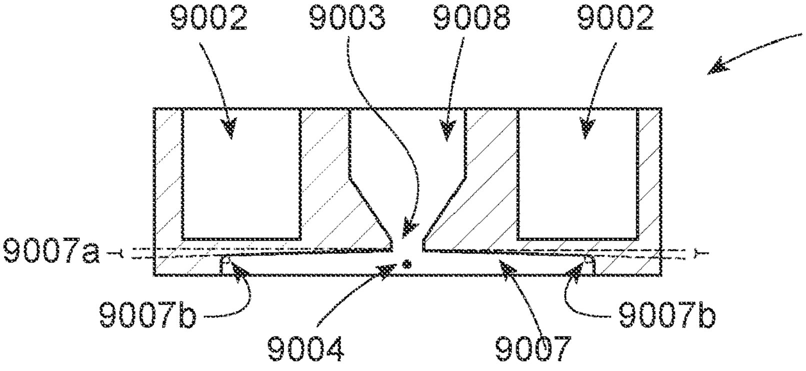
FIG. 17A is a cross section view of the strikethrough plate used in the Acquisition Time and Rewet Method described herein, taken along a plane defined by the z-direction and line 17A-17A shown in FIG. 15.
Figure 17B:
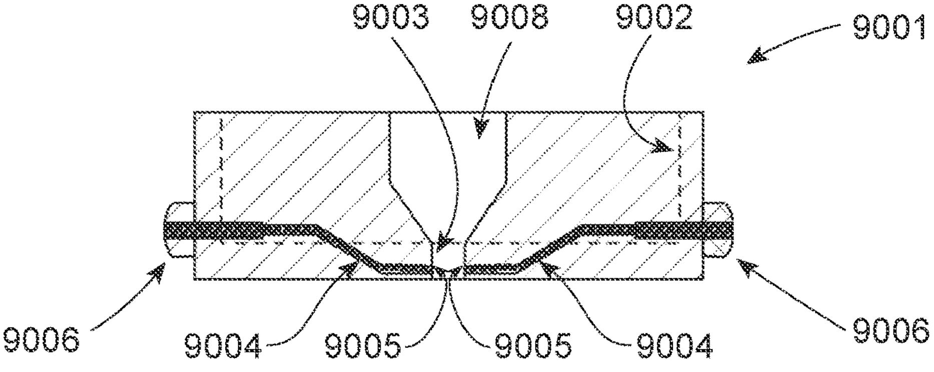
FIG. 17B is a cross section view of the strikethrough plate used in the Acquisition Time and Rewet Method described herein, taken along a plane defined by the z-direction and line 17B-17B shown in FIG. 15.

The measurement apparatus further includes a sample support 6050, which has the configuration and dimensions shown in FIG. 14. Sample support 6050 has a z-direction caliper of 0.75 mm (which is its height when placed into position within the measurement apparatus in preparation for a measurement procedure). Each of the concentric ring portions 6050*a* and radial spoke portions 6050*b* of sample support 6050 shown in FIG. 14 have an x-y plane width of 0.75 mm and a square cross section. Sample support 6050 is configured to support a test specimen 6160 within middle chamber portion 6030*b* of base 6030. Sample support 6050 may be cut or machined from any material of suitable strength and corrosion resistance, such as, for example, brass sheet stock.

It will be noted that the outside diameter of sample support 6050 and inside diameter of middle chamber portion 6030*b* are both specified above to be 30.0 mm. Sample support 6050 is disposed within middle chamber 6030*b* during the measurement procedure. Accordingly, it will be appreciated that either or both of inside diameter of middle chamber portion 6030*b* and outside diameter of sample support 6050 may require slight adjustment to provide a small but sufficient clearance to enable sample support 6050 to be conveniently inserted into and withdrawn from middle chamber portion 6030*b*.

Similarly, it will be noted that the outside diameter of the lower portion of sample weight 6040 and inside diameter of middle chamber portion 6030*b* are both specified above to be 30.0 mm; and the outside diameter of the upper portion of sample weight 6040 and inside diameter of upper chamber portion 6030*a* are both specified to be 40.0 mm. The lower portion of sample weight 6040 is disposed within middle chamber portion 6030*b*, and the upper portion of sample weight 6040 is disposed within upper chamber portion 6030*a*, during the measurement procedure. Accordingly, it will be appreciated that either or both of inside diameter of middle chamber portion 6030*b* and outside diameter of lower portion of sample weight 6040, and either or both of inside diameter of upper chamber portion 6030*a* and outside diameter of upper portion sample weight 6040, may require slight adjustment to provide a small but sufficient clearance to enable sample weight 6050 to be conveniently inserted into and withdrawn from middle chamber portion 6030*b*.

The measurement apparatus further includes a computer (not shown) with suitable software and interfacing equipment configured to communicate with the valve actuator 6100 to effect opening and closing of valve 6070, and to receive and collect fluid height data from fluid height sensor 6060 over time, at a rate of 100 Hz. The person of ordinary skill in the art will have sufficient knowledge and/or resources readily available to obtain components and configure the system including the computer and software to perform the operations described herein.

Test Fluid Preparation

The test fluid is an aqueous solution. The preparation of this test fluid is to be as follows.

The test fluid is an aqueous solution comprising low viscosity carboxymethylcellulose (CMC) sodium salt. The concentration of CMC salt added to deionized water is adjusted such that the resultant solution has a viscosity of 8+0.3 centipoise at a temperature of 23° C.±1 C°.

Viscosity of the prepared test fluid is performed using a low viscosity rotary viscometer (a suitable instrument is the Cannon LV-2020 Rotary Viscometer with UL adapter, Cannon Instrument Co., State College, Pennsylvania, or equivalent). The appropriate size spindle for the viscosity range is selected, and the instrument is operated and calibrated according to the manufacturer's instructions. Measurements are taken at 23° C.±1 C.° and at 30 rpm. Results are reported to the nearest 0.1 centipoise.

The components needed for the test fluid preparation are carboxymethylcellulose sodium salt (low viscosity, reagent grade, CAS 9004-32-4) and deionized water. The CMC salt is available from any convenient source, for example Merck KgaA/Sigma Aldrich (Burlington, Massachusetts), item #C5678.

The following preparation steps will result in about 2.5 liters of test fluid. The amount of CMC salt directly affects the final viscosity of the prepared test fluid, so the amount of CMC salt is adjusted to yield a final viscosity within the target range (8.0+0.3 centipoise). The amount of CMC salt required to reach 8 cP can vary from batch to batch. Addition of CMC salt within a range of 30 g to 40 g is usually successful, but less or more may be required. Add 2550 grams of deionized water to a 3 L beaker. CMC salt is slowly added to the beaker (starting with 15 grams) while stirring to minimize clumping. Continue stirring for about 30 minutes or until all of the CMC has dissolved and no clumps remain.

Ensure that the temperature of the prepared test fluid is at 23° C.±1 C°. Using the viscosity measurement procedure previously described, measure the viscosity. The target is 8+0.3 centipoise. If the prepared batch of test fluid does not meet the target, add more deionized water if viscosity is too high; or add more CMC salt in a small increment if the viscosity is too low. Measure the viscosity again, and repeat the content adjustment and measurement process until the target viscosity is reached.

The qualified batch of test fluid is stored covered at 23° C.±1 C°. The viscosity is tested daily prior to use to ensure the fluid meets the specified target.

Procedure

To obtain a test specimen for measurement, lay a single layer of dry subject material out flat on a horizontal work surface, and die-cut a test specimen from it that is circular, with a diameter of 30 mm. Avoid areas of the material having folds, wrinkles or tears when selecting a location for sampling.

If the subject material is a layer component of an absorbent article (e.g., a feminine hygiene pad), for example, a topsheet or absorbent layer component, obtain a representative sample of the subject material that has not been incorporated into an absorbent article. Alternatively, if only fully manufactured absorbent articles are available as sources of the subject material, from an example thereof, separate the subject layer component from the article without stretching or damaging it. Once the subject layer component has been removed from the article, die-cut out a test specimen as described above. Precondition the test specimen at 23° C.±2 C.° and 50%±2% relative humidity for 2 hours prior to testing.

Figure 12B:
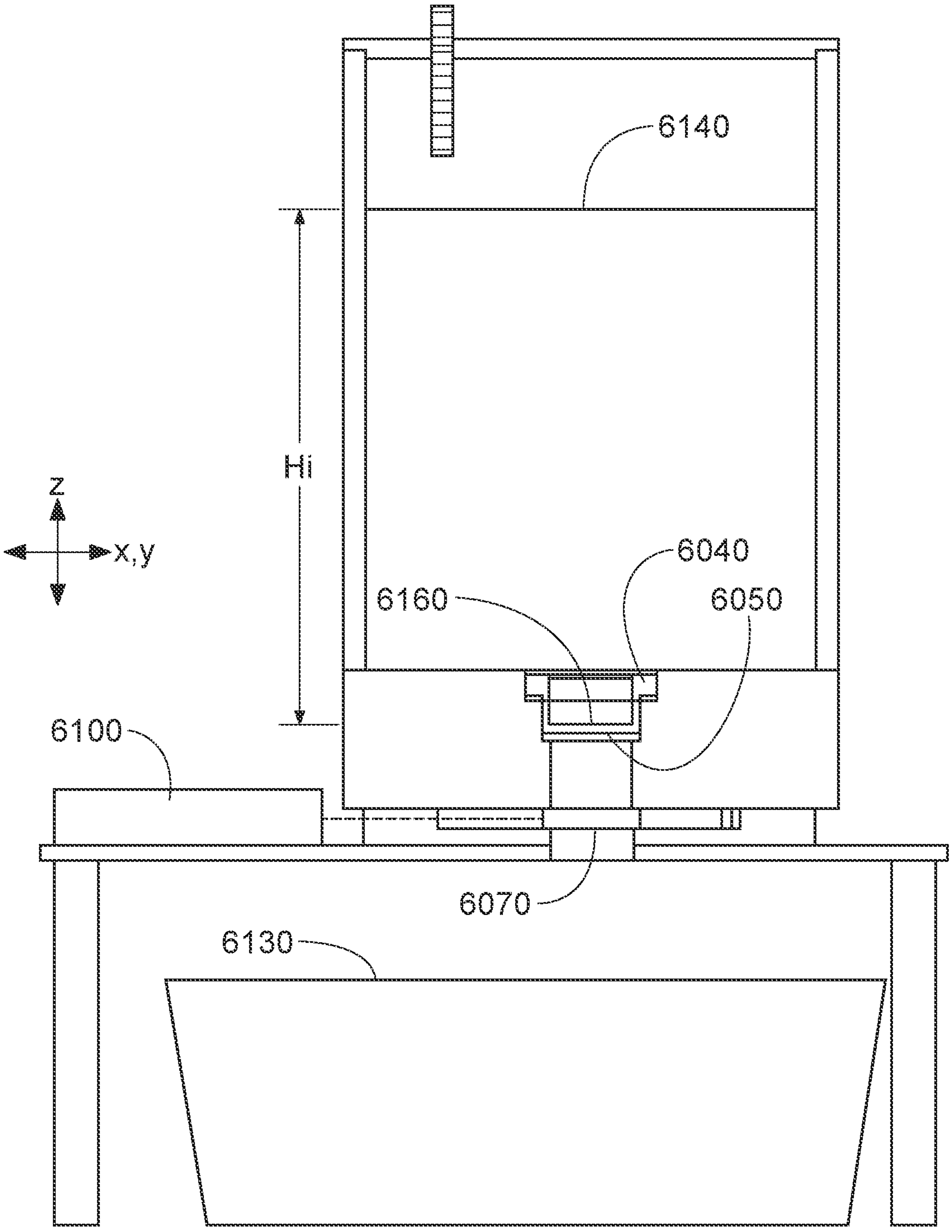
FIG. 12B is a view of the measurement apparatus as illustrated in FIG. 12*a*, illustrated with added elements in preparation for commencement of a measurement procedure.

Referring to FIG. 12B, with the fluid valve 6070 in closed position, insert the sample support 6050 into the middle chamber portion 6030*b* such that it lies horizontal/flat on the lower circumferential lip of middle chamber portion 6030*b*. Using forceps, gently place the test specimen 6160 over the sample support 6050 so that it lays flat thereon, with no wrinkles. Now gently place the sample weight 6040 over/onto the test specimen 6160 such that the lower portion of the weight 6040 is inserted into middle chamber portion 6030*b* and rests on the test specimen about its circumferential edge, and the upper portion of the weight 6040 is nested into the upper chamber portion 6030*a*.

Now slowly add the previously prepared test solution to the fluid vessel 6010, until an initial fluid surface 6140 height Hi of 150 mm above the upper surface of the test specimen 6160 is reached.

Allow the test specimen 6160 to equilibrate within the filled sample chamber for about 60 seconds, and ensure there are no bubbles present on the surface of the test fluid or surface of the test specimen. If bubbles are present on the fluid surface, remove or pop them using a clean instrument. If bubbles are present on the upper surface of the test specimen 6160, use a clean, round tip lab stirring rod to gently dislodge them, exercising care not to dislodge fibers (if the test specimen is fibrous), or stretch or damage the test specimen.

Secure the fluid height sensor 6060 to the lid 6020, and then place and fit the lid 6020 over cylindrical wall 6010*a*. Adjust the position of the fluid height sensor 6060, if necessary, prior to the start of the test so as to prevent it from contacting the starting surface of the test fluid. Initially, the lower tip of the sensor 6060 should be about 170 mm from the upper surface of the test specimen 6160.

Position the collection vessel 6130 below the valve 6070.

Figure 12C:
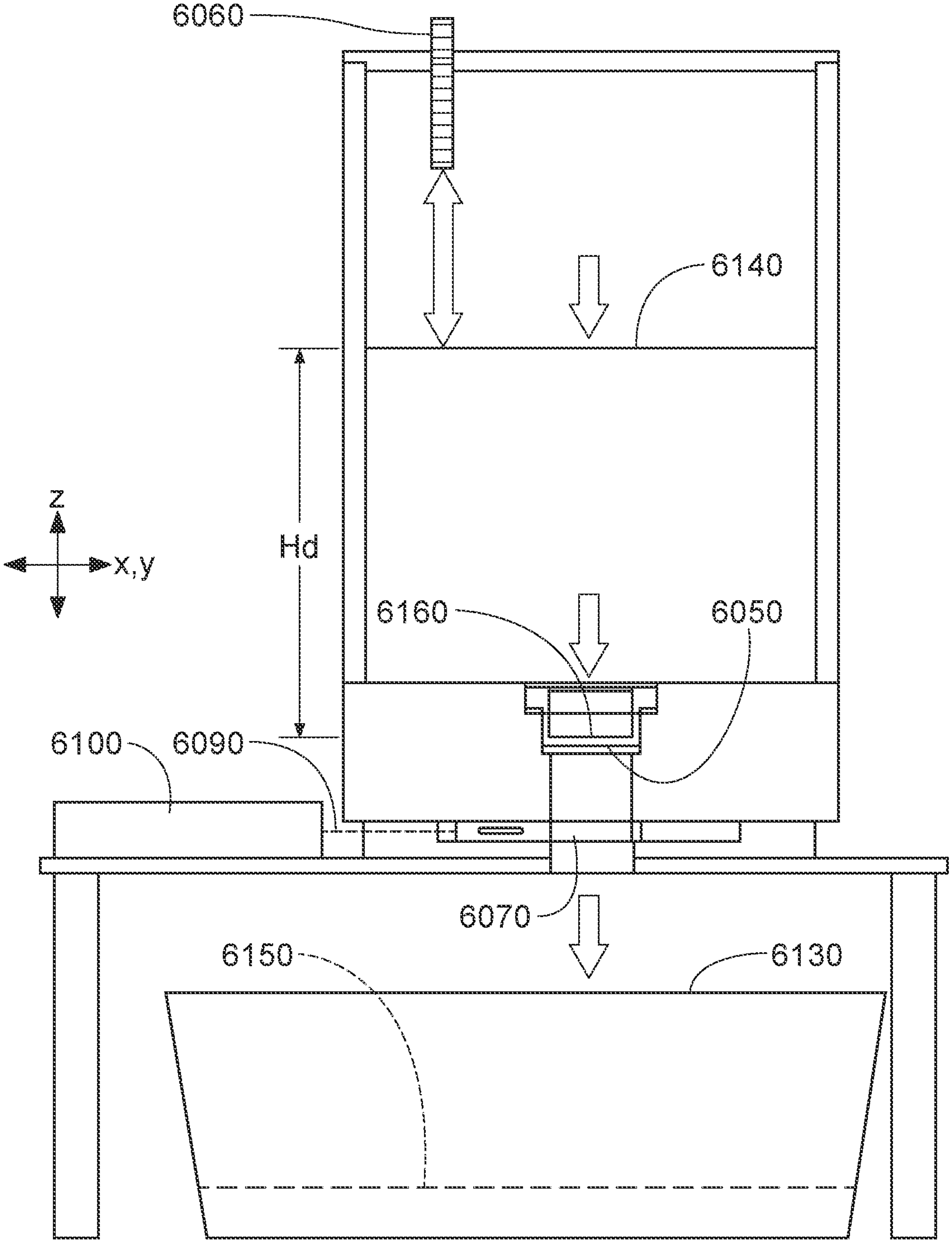
FIG. 12C is a view of the measurement apparatus as illustrated in FIG. 12*b*, illustrated following commencement of a measurement procedure.

Referring now to FIG. 12C, to start the measurement, simultaneously open the valve 6070 and start the acquisition of decreasing fluid height Hd and time data to the nearest 0.01 mm and 0.01 seconds, respectively, with a data acquisition rate of 100 Hz. Test fluid will flow under gravitational pull through the sample chamber and through test specimen 6160, sample support 6050 and open valve 6070, down into collection vessel 6130, and test fluid surface 6140 will fall while a surface 6150 of collected fluid will rise. Height sensor 6060 will sense and transmit data concerning the height of test fluid surface 6140 at the designated sensing frequency, over time. The measurement is ended and the valve 6070 is closed when test fluid has ceased exiting the valve, or after 1,000 seconds have elapsed, whichever occurs first. Remove the lid 6020. Lift the sample weight 6040 out of the sample chamber, and, using forceps, gently remove the wet test specimen 6160 from the sample chamber, and proceed to measure the wet caliper of the test specimen.

The wet caliper of the test specimen 6160 is measured promptly after completion of the measurement procedure, using a manually-operated micrometer equipped with a pressure foot capable of exerting a steady pressure of 2.07 kPa+0.07 kPa. The manually-operated micrometer is a dead-weight type instrument with readings accurate to 0.01 mm. A suitable instrument is Mitutoyo Series 543 ID-C Digimatic, available from Avantor/VWR International (Radnor, Pennsylvania) or equivalent. The pressure foot is a flat circular moveable face with a diameter of 19 mm. The test specimen is supported by a horizontal flat reference platform that is larger than and parallel to the surface of the pressure foot. Zero the micrometer against the horizontal flat reference platform. Transfer the wet test specimen 6160 to the reference platform of the micrometer such that the specimen 6160 is centered and lies horizontally and flat beneath the pressure foot. The pressure foot is lowered by hand with a descent rate of 3+1 mm/s until the full pressure (2.07 kPa) is applied to the test specimen. After 5 seconds elapse, the caliper of the wet test specimen is recorded as specimen caliper, to the nearest 0.01 mm. The test specimen is then discarded.

Remove test fluid inside the fluid vessel 6010 and sample chamber, if any remains therein.

The procedure is repeated for a total of three replicate test specimens.

A separate "blank" run measurement is performed by following the procedure described above, but with only the sample support 6050 and sample weight 6040 present in the sample chamber (i.e. no test specimen is present). Note that the initial test fluid height Hi will be 150 mm above the upper surface of the sample support 6050, rather than a surface of a specimen. This blank measurement will enable the permeability of the sample support 6050 to be considered, when calculating the permeability of the test specimen.

Permeability Calculation Total permeability, $k_{total}$, is the permeability of the test specimen plus the sample support, calculated from the time and volume of flow through a fluid height decrease from 150 mm test fluid to 130 mm test fluid.

Total permeability is calculated for each replicate test specimen using the following equation, and recorded to the nearest 0.01 $E^{-10}$ $m^2$:

$$\ln\left(\frac{Hi}{Hd}\right) = \frac{k_{total}\rho g}{\mu L_{total}} * \frac{R^2}{r^2} * t$$

thus, solved for $k_{total}$:

$$k_{total} = \frac{\left[\left(\frac{\ln\left(\frac{Hi}{Hd}\right)}{t}\right) * \frac{r^2}{R^2} * \mu * L_{total}\right]}{\rho g};$$

where:

Hi=initial test fluid height (150 mm)

Hd=test fluid height as decreased at time t (for the present calculation, this is 130 mm)

t=time (seconds) elapsed when fluid height has decreased to 130 mm $k_{total}$=combined permeability of the test specimen and the sample support ρ=density of the test fluid (kg/$m^3$)

g=gravitational constant (9.81 m/$s^2$)

μ=viscosity of the test fluid (0.008 kg/m-s)

$L_{total}$=combined caliper of the wet test specimen and the sample support (m)

R=the radius of the surface area of the test specimen through which the fluid flows ((26 mm/2)×(1 m/1,000 mm)=0.013 m)

r=radius of the inside of the fluid vessel ((98.425 mm/2)×(1 m/1,000 mm)=0.049213 m)

The permeability of the sample support 6050, $k_{ssup}$, is calculated in a similar manner, from the time and volume of flow through a fluid height decrease from 150 mm test fluid to 130 mm test fluid in the "blank" run. The permeability of the sample support 6050 alone is described by the following equation, and recorded to the nearest 0.01 $E^{-10}$ $m^2$:

$$\ln\left(\frac{Hi}{Hd}\right) = \frac{k_{ssup}\rho g}{\mu L_{ssup}} * \frac{R^2}{r^2} * t$$

thus, solved for $k_{ssup}$:

$$k_{ssup} = \frac{\left[\left(\frac{\ln\left(\frac{Hi}{Hd}\right)}{t}\right) * \frac{r^2}{R^2} * \mu * L_{frit}\right]}{\rho g};$$

where:

$L_{ssup}$=the caliper of the sample support 6050 (0.00075 m)

The permeability of each replicate test specimen, $k_{specimen}$, is calculated from the following equation, then multiplied by 1.01324998 $E^{+12}$ and recorded to the nearest 0.1 Darcy:

$$k_{specimen} = \frac{L_{specimen}}{\left(\frac{L_{total}}{k_{total}}\right) - \left(\frac{L_{ssup}}{k_{ssup}}\right)}$$

Now calculate the arithmetic mean of the test specimen permeability, $k_{specimen}$, across all three replicate test specimens, and report as Permeability to the nearest 0.1 Darcy.

Acquisition Time and Rewet Method

This method describes how to measure gush acquisition time, interfacial free fluid amount as well as low and high pressure rewet values for an absorbent article loaded with new Artificial Menstrual Fluid (nAMF; preparation provided separately herein). A pretreatment step is followed by three introductions of known volumes of nAMF to the absorbent article. The time required for the absorbent article to acquire each of the doses of nAMF is measured using a strikethrough plate and an electronic circuit interval timer. After each liquid dose, Interfacial Free Fluid (IFF) is measured gravimetrically as fluid is transferred from the bottom surface of the strikethrough plate to filter paper. Subsequently, low and high pressure rewet are measured after the last liquid dose. Surface Free Fluid (SFF) is the amount of fluid that remains in the topsheet of the absorbent article. SFF is measured by performing low pressure (0.1 psi) rewet. Immediately after measuring SFF, a higher pressure (0.5 psi) rewet is performed to determine the overall rewet of the absorbent article. All testing is performed in a room maintained at 23° C.±2 C.° and 50%±2% relative humidity.

Referring to FIGS. 15-17B, the strikethrough plate 9001 is constructed of Plexiglas, or equivalent, with an overall dimension of 10.2 cm long by 10.2 cm wide by 3.1 cm tall. A central, test fluid well 9008 has a circular opening of 25 mm in diameter is located at the top plane of the plate with initial lateral walls that extend 15 mm deep at a 90° angle and then slope downward at an angle of 82° for an additional depth of 7.5 mm to reach the test fluid reservoir 9003. The test fluid reservoir 9003 is concentric to the test fluid well 9008 and has a diameter of 6.6 mm with lateral walls that extend 5 mm deep at a 90° angle. The test fluid reservoir 9003 opens into the longitudinal fluid channel 9007 located at the bottom of the plate. The longitudinal fluid channel 9007 has lateral walls that initially extend 3.5 mm deep at the midpoint of the channel (just beneath the test fluid reservoir 9003), then slant downward at an angle 9007*a* of 0.72° towards each longitudinal end of the channel to a final depth of 3 mm. The longitudinal fluid channel opens to the bottom plane of the plate for the fluid to be introduced onto the underlying test sample. The longitudinal fluid channel 9007 is centered over the test fluid reservoir 9003 and extends in a direction that is perpendicular to the electrodes 9004. The longitudinal fluid channel 9007 has a width of 5 mm and a length of 80 mm, with lateral edges that are rounded with a radius 9007*b* of 1.0 mm. The longitudinal ends of the longitudinal fluid channel 9007 are rounded with a radius 9009 of 2.5 mm. Two wells 9002 (80.5 mm long by 24.5 mm wide by 25 mm deep) located outboard of the fluid reservoir, are filled with stainless steel shot (or equivalent) to adjust the overall mass of the plate to provide a constraining pressure of 0.10 psi (7.0 g/$cm^2$) to the Test Area.

The procedure for determining the test area is subsequently described herein. Electrodes 9004 are embedded in the plate 9001, connecting the exterior banana jacks 9006 to the inside wall 9005 of the longitudinal fluid channel 9003. A circuit interval timer is plugged into the jacks 9006, monitors the impedance between the two electrodes 9004, and measures the time from introduction of the nAMF into reservoir 9003 until the nAMF drains from the reservoir. The timer has a resolution of 0.01 sec.

A pretreatment plate is used in combination with a pretreatment weight to apply tiny droplets of nAMF to the surface of the test sample as a means to prime the surface of the test sample prior to the introduction of the full liquid dose. The pretreatment plate is constructed of Plexiglass, or equivalent, that is 14 inch (35.6 cm) long by 8 inch (20.3 cm) wide with a thickness of about 0.25 inch (6.4 mm). The pretreatment plate has five circular markers, each 5 mm in diameter, placed 1 cm apart (center to center) that are aligned along the longitudinal axis of the plate. The central marker is centered at the lateral midpoint of the plate. These markers indicate the placement of the nAMF droplets. The markers are located on the underside of the pretreatment plate and can be milled out or simply drawn on with a permanent marker, or equivalent. The pretreatment weight is 10.2 cm×10.2 cm and consists of a flat, smooth rigid material (e.g. stainless steel) with an optional handle. The pretreatment weight (including optional handle) has a total mass of 726 g±0.5 g to give a pressure of 0.10 psi (7.0 g/cm$^2$) across the bottom surface area of the weight.

When measuring the interfacial fluid amounts, a rubber pad is used to provide a reproducibly flat surface that enables even pressure distribution. The IFF rubber pad is constructed from high strength neoprene rubber with 40 A durometer and a thickness of ⅛ inch (available from W.W. Grainger, Inc, item #1DUV4, or equivalent) and cut to dimensions of 6 inch (15.2 cm) by 6 inch (15.2 cm).

For the overall rewet portion of the test, a padded weight assembly that applies 0.5 psi (35.1 g/cm$^2$) to the Test Area is required. The procedure for determining the test area is subsequently described herein. The rewet weight is constructed as follows. Lay a piece of polyethylene film (about 25 microns thick, any convenient source) horizontally flat on a rigid bench surface. A piece of polyurethane foam (25 mm thick, density of 1.0 lb/ft$^3$, IDL 24 psi, available from Concord-Renn Co. Cincinnati, OH, or equivalent) is cut to 10.2 cm by 10.2 cm and then laid centered on top of the film. A piece of Plexiglas (10.2 cm by 10.2 cm and about 6.4 mm thick) is then stacked on top of the polyurethane foam. Next the polyethylene film is used to wrap the polyurethane foam and Plexiglas plate securing it with transparent tape. A metal weight with handle is stacked on top of, and fastened to, the Plexiglass plate such that the total mass of the padded weight assembly can be adjusted to apply a pressure of 0.5 psi (35.1 g/cm$^2$) to the Test Area.

For the IFF, SFF and overall rewet steps, various layers of filter paper are required. The filter paper is conditioned at 23° C.±2 C.° and 50%±2% relative humidity for at least 2 hours prior to testing. A suitable filter paper has a basis weight of about 88 gsm, a thickness of about 249 microns with an absorption rate of about 5 seconds, and is available from Ahlstrom-Munksjo (Mt. Holly Springs, PA) as grade 632, or equivalent. The filter paper has dimensions of 5 inch by 5 inch (12.7 cm by 12.7 cm).

Test samples are conditioned at 23° C.±2 C.° and 50%±2% relative humidity for at least 2 hours prior to testing. Test samples are removed from their outer packaging and the wrappers are opened to unfold the product, if applicable, using care not to press down or pull on the products while handling. No attempt is made to smooth out wrinkles. Tear the release paper between the wings, if applicable, and lay the sample on a horizontally flat, rigid surface with the body-side facing up (e.g. panty-side down). Determine the dose location as follows. For symmetrical products (i.e. the front of the product is the same shape and size as the back of the product when laterally divided along the midpoint of the longitudinal axis of the product), the dose location is the intersection of the midpoints of the longitudinal and lateral axes of the absorbent core. For asymmetrical products (i.e. the front of the product is not the same shape and size as the back of the product when laterally divided along the midpoint of the longitudinal axis of the product), the dose location is the midpoint of the product's wings at the lateral midpoint of the absorbent core. For products that have a foam core with holes and slits either punched out or printed, the dose location is the longitudinal midpoint of the hole-punched (or hole-printed) region at the lateral midpoint of the absorbent core. Once determined, mark the dose location with a small dot using a black, fine-tip, permanent marker. If wings are present, fold them to the back of the product.

Determine the Test Area of the test sample, as follows. This area will be used so that the mass of the strikethrough plate and the mass of the rewet weight can be properly adjusted to deliver the required pressure (0.1 psi and 0.5 psi, respectively). Measure the width of the absorbent core of the test sample as the distance between one lateral edge of the core to the other lateral edge of the core along a line that is positioned at the dosing location and runs perpendicular to the longitudinal axis of the test sample, and record as core width to the nearest 0.01 cm. Now multiply the core width by 10.2 cm (the length of the strikethrough plate and rewet weight) and record as Test Area to the nearest 0.1 cm$^2$. The total mass of the strikethrough plate is the Test Area multiplied by 7 g/cm$^2$. The total mass of the rewet weight is the Test Area multiplied by 35.1 g/cm$^2$.

The test sample is pretreated with nAMF as follows. Place the pretreatment plate onto a horizontally flat, rigid surface such that the side with the circular markers is facing down. Using a single channel, fixed volume pipettor, accurately dispense 50 uL of nAMF onto the topside of the pretreatment plate at the location of each of the five circular markers. Position the test sample above the pretreatment plate such that the body-side of the sample is facing the plate, the longitudinal axis of the sample and plate are aligned, and the pre-marked dose location on the test sample is centered over the central droplet of nAMF on the pretreatment plate. After properly positioned, place the test sample into contact with the pretreatment plate, then immediately apply the pretreatment weight onto the back side of the test sample, centering it over the dose location/central droplet of nAMF on the pretreatment plate. Start a 40 second timer. After 40 seconds have elapsed, remove the pretreatment weight from the test sample and remove the test sample from the pretreatment plate. Invert the test sample so that the body-side is facing up, place it onto a horizontally flat, rigid surface and immediately proceed with the steps that follow.

The first acquisition time (ACQ-1) is measured as follows. Connect the electronic circuit interval timer to the strikethrough plate 9001 and zero the timer. Position the strikethrough plate 9001 above the body-side of the test sample such that the long axis of the longitudinal fluid channel 9007 on the underside of the strikethrough plate 9001 is aligned with the longitudinal axis of the test sample, and ensure that the fluid reservoir 9003 is centered over the pre-marked dose location on the test sample. To note, nAMF should be visible through the fluid reservoir 9003 at the dose location on the test sample. After properly positioned, gently place the strikethrough plate 9001 onto the test sample. Using an adjustable volume pipettor, accurately dispense 2.0 mL of nAMF into the fluid well 9008 in the strikethrough plate 9001. The fluid is dispensed, without splashing, along the angled walls of the fluid well 9008 within a period of 3 seconds or less. Immediately after the fluid has been acquired, record the first acquisition time (ACQ-1) displayed on the circuit interval timer to the nearest 0.1 seconds. Leave the strikethrough plate 9001 in place on the test sample, and immediately start a 2 minute timer.

After 2 minutes have elapsed, measure the first Interfacial Free Fluid (IFF-1) as follows. Place the IFF rubber pad onto a horizontally flat, rigid surface. Measure the mass of one layer of filter paper to the nearest 0.0001 g and record as IFF-$1_{initial}$. Place the filter paper centered onto the IFF rubber pad. Transfer the strikethrough plate 9001 from the test sample to the pre-weighed filter paper such that the plate is centered on the filter paper, and immediately start an 8 minute timer. After 10 seconds have elapsed on the 8 minute timer, remove the strikethrough plate from the filter paper and gently replace it back onto the test sample, exactly as previously positioned. Within the next 10 seconds, measure the mass of the filter paper to the nearest 0.0001 g and record as IFF-$1_{final}$.

The second acquisition time (ACQ-2) is measured as follows. After 8 minutes have elapsed, apply the second gush of fluid using an adjustable volume pipettor to accurately dispense 4.0 mL of nAMF into the fluid well 9008 in the strikethrough plate 9001, as previously described. Immediately after the fluid has been acquired, record the second acquisition time (ACQ-2) displayed on the circuit interval timer to the nearest 0.1 second. Leave the strikethrough plate 9001 in place on the test sample, and immediately start a 2 minute timer.

After 2 minutes have elapsed, measure the second Interfacial Free Fluid (IFF-2) as follows. Place the IFF rubber pad onto a horizontally flat, rigid surface. Measure the mass of a fresh, single layer of filter paper to the nearest 0.0001 g and record as IFF-$2_{initial}$. Place the filter paper centered onto the IFF rubber pad. Transfer the strikethrough plate 9001 from the test sample to the pre-weighed filter paper such that the plate is centered on the filter paper and immediately start an 8 minute timer. After 10 seconds have elapsed on the 8 minute timer, remove the strikethrough plate 9001 from the filter paper and gently replace it back onto the test sample, exactly as previously positioned. Within the next 10 seconds, measure the mass of the filter paper to the nearest 0.0001 g and record as IFF-$2_{final}$.

The third acquisition time (ACQ-3) is measured as follows. After 8 minutes have elapsed, apply the third gush of fluid using an adjustable volume pipettor to accurately dispense 2.0 mL of nAMF into the fluid well 9008 in the strikethrough plate 9001, as previously described. Immediately after the fluid has been acquired, record the third acquisition time (ACQ-3) displayed on the circuit interval timer to the nearest 0.1 second. Leave the strikethrough plate 9001 in place on the test sample, and immediately start a 2 minute timer.

After 2 minutes have elapsed, measure the third Interfacial Free Fluid (IFF-3) as follows. Place the IFF rubber pad onto a horizontally flat, rigid surface. Measure the mass of a fresh, single layer of filter paper to the nearest 0.0001 g and record as IFF-$3_{initial}$. Place the filter paper centered onto the IFF rubber pad. Transfer the strikethrough plate 9001 from the test sample to the pre-weighed filter paper such that the plate is centered on the filter paper and immediately start an 8 minute timer. After 10 seconds have elapsed on the 8 minute timer, remove the strikethrough plate 9001 from the filter paper and set it on its side so that the pad-side of the plate is not contacting the bench. Within the next 10 seconds, measure the mass of the filter paper to the nearest 0.0001 g and record as IFF-$3_{final}$.

Measure Surface Free Fluid (SFF) as follows. After 8 minutes have elapsed, measure the mass of a fresh stack of 5 filter papers to the nearest 0.0001 g and record as $SFF_{initial}$. Place the stack of filter papers on top of the body-side of the test sample such that they are centered over the dose location. Now gently place the strikethrough plate 9001 on top of the filter papers such that the pad-side of the plate is centered on the filter papers, and immediately start a 10 second timer. After 10 seconds have elapsed, remove the strikethrough plate 9001 from the filter papers and set it aside. Measure the mass of the stack of 5 filter papers to the nearest 0.0001 g and record as $SFF_{final}$. Immediately proceed to the next step.

Measure overall rewet as follows. Measure the mass of a fresh stack of 5 filter papers to the nearest 0.0001 g and record as $REWET_{initial}$. Place the filter papers on top of the body-side of the test sample such that they are centered over the dose location. Now place the padded Rewet Weight on top of the stack of filter papers such that the weight is centered on the filter paper stack, and immediately start a 30 second timer. After 30 seconds have elapsed, remove the rewet weight and measure the mass of the stack of 5 filter papers to the nearest 0.0001 g, then record as $REWET_{final}$. Discard the sample and thoroughly clean and then dry the fluid well 9008, fluid reservoir 9003, longitudinal fluid channel 9007 and the bottom surface of the strikethrough plate 9001 prior to testing the next sample.

Make the following calculations for each of the parameters measured, as follows. Calculate Total Gush Absorbency Time as the sum of ACQ-1, ACQ-2 and ACQ-3, and record to the nearest 0.1 second. Calculate IFF-1 by subtracting IFF-$1_{initial}$ from IFF-$1_{final}$, and record to the nearest 0.0001 g. Calculate IFF-2 by subtracting IFF-$2_{initial}$ from IFF-$2_{final}$, and record to the nearest 0.0001 g. Calculate IFF-3 by subtracting IFF-$3_{initial}$ from IFF-$3_{final}$, and record to the nearest 0.0001 g. Calculate Total IFF as the sum of IFF-1, IFF-2 and IFF-3, and record to the nearest 0.1 g. Calculate SFF by subtracting $SFF_{initial}$ from $SFF_{final}$, and record to the nearest 0.0001 g. Calculate Total IFF+SFF as the sum of Total IFF and SFF, and record to the nearest 0.1 g. Calculate Overall Rewet by subtracting $REWET_{initial}$ from $REWET_{final}$, and record to the nearest 0.0001 g.

The entire procedure is repeated for a total of three replicate test samples. The reported value for each of the parameters is the arithmetic mean of the three individually recorded measurements for each Acquisition Time (ACQ-1, ACQ-2 and ACQ-3) to the nearest 0.1 seconds, Total Gush Absorbency Time to the nearest 0.1 seconds, Interfacial Free Fluid (IFF-1, IFF-2 and IFF-3) to the nearest 0.0001 g, Total IFF to the nearest 0.1 g, Surface Free Fluid (SFF) to the nearest 0.0001 g, Total IFF+SFF to the nearest 0.1 g, and Overall Rewet to the nearest 0.0001 g.

New Artificial Menstrual Fluid (nAMF) Preparation

This formulation of new Artificial Menstrual Fluid (nAMF) is composed of a mixture of defibrinated sheep blood, a phosphate buffered saline solution and a mucous component. The nAMF is prepared such that it has a viscosity between 7.40 to 9.00 centipoise at 23° C.

Viscosity of the nAMF is performed using a low viscosity rotary viscometer (a suitable instrument is the Brookfield DV2T fitted with a Brookfield UL adapter, available from AMETEK Brookfield, Middleboro, MA, or equivalent). The appropriate size spindle for the viscosity range is selected, and the instrument is operated and calibrated as per the manufacturer. Measurements are taken at 23° C.±1 C.° and at 60 rpm. Results are reported to the nearest 0.01 centipoise.

Reagents needed for the nAMF preparation include: defibrinated sheep blood with a packed cell volume of 38% or greater (collected under sterile conditions, available from Cleveland Scientific, Inc., Bath, OH, or equivalent), gastric mucin with a viscosity target of 3-4 centistokes when prepared as a 2% aqueous solution (crude form, sterilized, available from American Laboratories, Inc., Omaha, NE, or equivalent), sodium phosphate dibasic anhydrous (reagent grade), sodium chloride (reagent grade), sodium phosphate monobasic monohydrate (reagent grade), sodium benzoate (reagent grade), benzyl alcohol (reagent grade) and distilled water, each available from VWR International or equivalent source.

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. To prepare about 200 mL of phosphate buffered saline solution, add 49.50 g±0.10 g of Solution A and 157.50 g±0.10 g of Solution B to a sufficiently size bottle that has a lid with a good seal. Then add 1.0 g of sodium benzoate and 1.60 g of benzyl alcohol to the bottle along with a stir bar and set aside.

The mucous component of the nAMF is a mixture of the phosphate buffered saline solution and gastric mucin. The amount of gastric mucin added to the mucous component directly affects the final viscosity of the prepared nAMF. To determine the amount of gastric mucin needed to achieve nAMF within the target viscosity range (7.4-9.0 centipoise at 23° C. and 60 rpm), prepare 3 batches of nAMF with varying amounts of gastric mucin in the mucous component, and then interpolate the exact amount needed from a concentration versus viscosity curve with a least squares linear fit through the three points. A successful range of gastric mucin is usually between 13 to 15 grams per 400 mL batch of nAMF, although this can vary significantly based upon the supplier, age, and lot of mucin.

To prepare about 200 mL of the mucous component, add the pre-determined amount of gastric mucin to the bottle containing the previously prepared phosphate buffered solution and then apply the lid. Place the bottle on a wrist-action shaker for 5 minutes at the highest speed. After 5 minutes, remove the flask of mucous component from the wrist-action shaker and place onto a magnetic stir plate. Stir for at least 2 hours until there are no lumps of mucin present, then remove the stir bar from the flask. Using a homogenizer, blend the mucous component for 5 minutes at 10,000 rpm. A suitable homogenizer is the T18 Ultra-Turrax fitted with a S18N-19G dispersing tool (19 mm stator diameter, 12.7 mm rotor diameter, 0.4 mm gap between rotor and stator), both available from IKA Works, Inc, Wilmington, NC, or equivalent. After the final mixing step, measure and record the viscosity of the mucous component to the nearest 0.01 centipoise at 23° C.±1 C.° and at 20 rpm using the viscometer with the UL adapter. Ensure that the viscosity of the prepared mucous component is within the target range of 9.0-11.0 centipoise.

The nAMF is a 50:50 mixture of the mucous component and sheep blood. Ensure the temperature of the sheep blood and mucous component are 23° C.±1 C°. To prepare about 400 mL of nAMF, add 200 g of the mucous component to a glass bottle with at least 500 mL capacity. Now add 200 g of sheep blood to the bottle along with a stir bar. Mix on a magnetic stir plate until thoroughly combined. Ensure the viscosity of the prepared nAMF is within the target range of 7.4-9.0 centipoise when measured at 23° C.±1 C.° and 60 rpm using the viscometer with the UL adapter. If the viscosity is too high, it can be adjusted by adding the previously prepared phosphate buffered saline solution in 0.5 g increments followed by stirring for 2 minutes and then re-checking the viscosity until the target range is reached.

The qualified nAMF should be refrigerated at 4° C. unless intended for immediate use. nAMF may be stored in an air-tight container at 4° C. for up to 48 hours after preparation. Prior to testing, the nAMF must be brought to 23° C.±1 C°. Any unused portion is discarded after testing is complete.

EXAMPLES/DATA

The following data and examples, including comparative examples, are provided to help illustrate the upper and lower nonwoven layers, absorbent core structures and/or absorbent articles described herein. The exemplified structures are given solely for the purpose of illustration and are not to be construed as limitations of the present disclosure, as many variations thereof are possible without departing from the spirit and scope of the invention.

Nonwoven Material Test

Nonwoven layer materials are tested to assess the ability of the nonwoven material to strain (elongate) with a balanced stretch and to recover to their original state (simulating in-use physical deformation). Samples F-H are comparative examples. Sample A-H and I are tested at different times; however, the data are shown together for ease of comparation. The test is performed according to the CD Cyclic Elongation to 3% Strain Method and the Strain to Break Method described herein. The results are shown in Table 1.

TABLE 1

Nonwoven Materials tested in the CD Cyclic Elongation to 3% Strain Method and the Strain to Break Method

| Sample | Nonwoven Material | Fiber Composition | Tensile Stiffness N/mm | Permanent Strain mm/mm | % Strain to Break % |
|---|---|---|---|---|---|
| A | 40 gsm Carded Resilient Nonwoven[1] | BiCo (PE/PET) - 60% 2 DTex/ 40% 4 DTex Blend | 0.30 | 0.0060 | >10% |
| B | 55 gsm Resilient Spunlace 1[2] | 30% 10 DTex HS-PET; 20% 1.3 DTex Rayon; 50% 2.2 DTex BiCo (PE/PET) | 1.57 | 0.0064 | >10% |

TABLE 1-continued

Nonwoven Materials tested in the CD Cyclic Elongation to 3% Strain Method and the Strain to Break Method

| Sample | Nonwoven Material | Fiber Composition | Tensile Stiffness N/mm | Permanent Strain mm/mm | % Strain to Break % |
|---|---|---|---|---|---|
| C | 50 gsm Resilient Spunlace 6[3] | 20% 1.3 DTex Rayon; 20% 3.3 DTex tri-lobal Rayon; 60% 5.8 DTex PE/PET | 1.50 | 0.0054 | >10% |
| D | 24 gsm Carded Nonwoven[4] | 100% 2 DTex BiCo (PE/PET) | 0.16 | 0.0160 | >10% |
| E | 55 gsm Resilient Spunlace 5[5] | 40% 1.7 DTex/38 mm Rayon; 40% 2.2 DTex PET; 20% 10 DTex HS PET | 0.31 | 0.0127 | >10% |
| F | 18 gsm Spunbond Nonwoven[6] | 100% 2.0 DTex PP | 0.24 | 0.0096 | >10% |
| G | 25 gsm Spunbond Nonwoven[7] | 100% 2.0 Dtex PP | 0.37 | 0.0093 | >10% |
| H | 17 gsm Tissue[8] | 100% Cellulose | 1.72 | 0.0137 | <5% |
| I | 10 gsm SMS Nonwoven[9] | 80% 1.5 DTex PP; 20% 0.1 DTex PP | 0.21 | 0.0086 | >10% |

[1]Available as ATB Z87G-40 from Xiamen Yanjan New Material Co. (China)
[2]Available as Sawasoft ® 53FC041001 from Sandler GmbH (Germany)
[3]Available as Sawasoft ® 553FC041005 (option 82) from Sandler GmbH (Germany)
[4]Available as Aura 20 from Xiamen Yanjan New Material Co. (China)
[5]Available as S25000541R01 from Jacob Holms Industries (Germany)
[6]Available as PFNZN 18G BICO8020 PHI 6 from dPFNonwovens Czech S.R.O (Czech Republic)
[7]Available as PEGZN25 BICO7030 Phobic from dPFNonwovens Czech S.R.O (Czech Republic)
[8]Available as 3028 from DunnPaper (USA)
[9]Available as 10 SMS PHILIC from Union Industries SpA. (Italy)

It is found that suitable nonwoven layer materials strain (elongate) with a balanced stretch vs. recovery behavior. If the nonwoven layer material elongates plastically (i.e., stretches but does not recover) as the fluff/AGM matrix in the inner core layer elongates, there will be insufficient recovery energy to return to the initial, pre-stretched state and the nonwoven layer material will become permanently strained (stretched). The upper nonwoven layers of the present disclosure can have a Permanent Strain value of less than about 0.013. At the same time, if the nonwoven layer material is strained aggressively, for example greater than 5%, the nonwoven layer material needs to retain its integrity and not tear or break (see, for example, Sample H which tears and has a Strain to Break of less than 5%). Nonwoven layers of the present disclosure can have a Strain to Break of greater than about 10%.

A subset of the nonwoven layer materials described above are also tested to assess the ability of nonwoven materials to bend and deform and to recover to their original state. The test is performed according to the Wet and Dry CD Ultra Sensitive 3 Point Bending Method described herein. The results are shown in Table 2.

TABLE 2

Nonwoven Materials Tested in the Wet and Dry CD Ultra Sensitive 3 Point Bending Method

| Sample | Dry Peak Load N | Dry Bending Energy N*mm | Dry Recovery Energy N*mm |
|---|---|---|---|
| A | 0.07 | 0.219 | 0.092 |
| B | 0.38 | 1.015 | 0.291 |

TABLE 2-continued

Nonwoven Materials Tested in the Wet and Dry CD Ultra Sensitive 3 Point Bending Method

| Sample | Dry Peak Load N | Dry Bending Energy N*mm | Dry Recovery Energy N*mm |
|---|---|---|---|
| C | 0.26 | 0.595 | 0.201 |
| D | 0.09 | 0.176 | 0.036 |
| E | 0.03 | 0.059 | 0.032 |
| F | 0.01 | 0.0216 | 0.005 |
| G | 0.03 | 0.0624 | 0.019 |
| H | 0.04 | 0.0734 | 0.031 |

During walking, an absorbent article is compressed and bent side-to-side in a cyclic pattern as the gap between her legs narrows and then expands with her leg motions. Without being limited by theory, it is believed that a nonwoven layer material having a Dry Bending Energy of less than about 2 N*mm will allow this bending compression to occur readily yet will not be so stiff as to hinder the bending compression. At the same time, following the bending compression, the nonwoven layer needs to be able to sustain sufficient dry recovery energy to return the nonwoven layer and the fluff/AGM matrix in the inner core layer back to its initial, pre-bent state. The upper nonwoven layers of the present disclosure can have a Dry Recovery Energy value of greater than about 0.03 N*mm.

Samples A-E exhibit a Dry Peak Load of from 0.03N to 0.38N and a Dry Recovery Energy of from 0.032 to 0.092 N*mm, demonstrating that these materials readily bend and have sufficient dry recovery energy to recover their initial, pre-bent state. Samples F and G, which are comparative examples, exhibit a Dry Peak Load of 0.01N and 0.03N, respectively, and a Dry Recovery Energy of 0.005 N*mm and 0.019 N*mm, respectively, demonstrating that while these materials readily bend, they do not have sufficient recovery energy to recover their initial, pre-bent state after compression. Sample H (comparative example) exhibits a Dry Peak Load of 0.04 N and a Dry Recovery Energy of 0.031 N*mm. However, it is found that Sample H tears when it becomes wet, making it insufficient to function as an upper and/or lower nonwoven layer of the present disclosure.

Without being limited by theory, it is believed that nonwoven layer materials comprising thick fibers (from about 2.0 Dtex to about 10 Dtex) that are arranged within a network structure are able to carry the mechanical load within the fiber network and return the absorbent core structure and/or absorbent article to its initial shape following bending compression. Samples F and G comprise relatively fine fibers (less than about 2.0 Dtex), while Samples A-E comprise fiber blends having a fiber thickness of from about 2.2 Dtex to about 10 Dtex.

Absorbent Core Structure Test

Absorbent cores structures are tested to assess the ability of the absorbent core structure to compress (simulating the compressions experienced between a wearer's legs) and to recover to their original state. Examples 1-3 illustrate absorbent core structures described herein. Comp. Ex. A-C are comparative examples. A description of Ex. 1-3 and Comp. Ex. A-C are listed in Table 3. The absorbent core structures are prepared as described hereafter. The absorbent core structures are evaluated according to the Wet and Dry Bunched Compression Method as described herein. The results are shown in Table 4.

TABLE 3

Absorbent Core Structures

| Example | Upper Nonwoven Layer | Inner Core Layer | Lower Nonwoven Layer |
|---|---|---|---|
| Ex. 1 | 40 gsm Carded Resilient Nonwoven[1] | 175 gsm Fluff[11]/ 70 gsm AGM[10] | 18 gsm Spunbond Nonwoven[6] |
| Ex. 2 | 55 gsm Resilient Spunlace 5[5] | 175 gsm Fluff[11]/ 70 gsm AGM[10] | 18 gsm Spunbond Nonwoven[6] |
| Ex. 3 | 50 gsm Resilient Spunlace 6[3] | 175 gsm Fluff[11]/ 70 gsm AGM[10] | 40 gsm Carded Nonwoven[1] |
| Comp. Ex. A | 24 gsm Carded Nonwoven[4] | 175 gsm Fluff[11]/ 70 gsm AGM[10] | 10 gsm SMS Nonwoven[12] |
| Comp. Ex. B | 17 gsm Tissue[8] | 175 gsm Fluff[11]/ 70 gsm AGM[10] | 17 gsm Tissue[8] |
| Comp. Ex. C | 17 gsm Tissue[8] (10 × 10 bonding) | 175 gsm Fluff[11]/ 70 gsm AGM[10] | 17 gsm Tissue[8] |

[1]Available as ATB Z87G-40 from Xiamen Yanjan New Material Co. (China)
[3]Available as Sawasoft ® 553FC041005 (option 82) from Sandler GmbH (Germany)
[4]Available as Aura 20 from Xiamen Yanjan New Material Co. (China)
[5]Available as S25000541R01 from Jacob Holms Industries (Germany)
[6]Available as PFNZN 18G BICO8020 PHI 6 from dPFNonwovens Czech S.R.O (Czech Republic)
[8]Available as 3028 from DunnPaper (USA)
[10]Available as Favor SXM9745 from Evonik (Germany)
[11]Available as Item 9E3-COOSABSORB S from Resolute Alabama (USA)
[12]Available as Article 4004416 (MR 3585374) from Fitesa (Germany)

The absorbent core structures listed in Table 3 are produced as detailed within the specification. Specifically, the upper nonwoven layer is first introduced onto the forming drum within the laydown section, and under vacuum it is drawn into the 3 dimensional pocket shape. A homogeneous stream of the fluff (cellulose) and AGM material is deposited onto the upper nonwoven layer directly within the forming station. Prior to entering the forming station, the upper nonwoven is coated with a spray adhesive (Technomelt DM 9036U available from Henkel, (Germany), 6 gsm continuous meltblown spirals, 50 mm wide) to provide a stronger connection of the fluff (cellulose) and AGM to the upper nonwoven layer without hindering the flow of liquid into the fluff/AGM matrix. On exiting the laydown section, the lower nonwoven web is combined with the nonwoven carrying the homogeneous blend of fluff/AGM. This lower nonwoven is precoated with adhesive (Technomelt DM 9036U available from Henkel (Germany)) to enable a perimeter seal (10 gsm meltblown spirals, 20 mm wide on the sides) and in the center a 6 gsm, 50 mm wide continuous meltblown spiral adhesive is applied to better integrate the fluff/AGM matrix.

Figure 4:
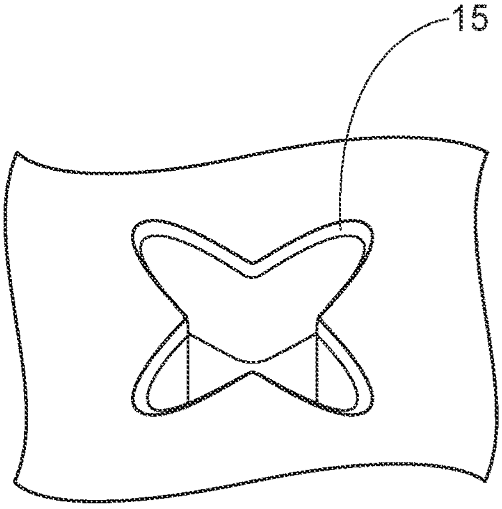
FIG. 4 is a close up illustration of a structural bond site in accordance with the present disclosure.

Ex. 1 through 3 and Comp. Ex. A and B also have the structural bonds shown in FIG. 4 with the profile shown in FIG. 5. Ex. 1-3 and Comp. Ex. A-B have a structural bond spacing of 32 mm×16 mm, thereby occupying a total structural bond site area of 1.38% of the total area of the absorbent core structure. Comp Ex. C is identical to Comp. Ex. B except the structural bond spacing is 10 mm×10 mm, thereby occupying a total structural bond site area of 6.28% of the total area of the absorbent core structure. The structural bonds are applied with a heated aluminum die to create an emboss pattern within a heated hydraulic press. The structural bond embosser plate has protrusions of an area of 3.55 $mm^2$ and about 1 mm in height as shown in FIG. 4 with the profile shown in FIG. 5. The structural bonds are spaced according to the dimensions of separation described above. The structural bond embosser plate is heated to 120° C. and set to a compression pressure of 170 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the structural bond pattern.

Ex. 1-3 and Comp. Ex. A-C also have flex bond channel regions applied with the pattern shown in FIG. 2C. The flex bond channel regions are applied with a heated aluminum die to create an emboss pattern within a heated hydraulic press. The flex bond channel embosser plate has protrusions spaced about 1.5 mm apart and are about 3 mm long and about 1.5 mm wide. The bond channel embosser plate is heated to 120° C. and set to a compression pressure of 200 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the emboss pattern.

TABLE 4

Absorbent Core Structures Measured in the Wet and Dry Bunched Compression Method

| Example | Wet and Dry Bunched Compression Method | |
|---|---|---|
| | $5^{th}$ Cycle Wet Maximum Compression Force (gf) | $5^{th}$ Cycle Wet Energy of Recovery (N*mm) |
| Ex. 1 | 208 | 1.30 |
| Ex. 2 | 207 | 1.07 |
| Ex. 3 | 213 | 1.76 |
| Comp. Ex. A | 136 | 0.26 |

TABLE 4-continued

Absorbent Core Structures Measured in the Wet and Dry Bunched Compression Method

| Example | Wet and Dry Bunched Compression Method: $5^{th}$ Cycle Wet Maximum Compression Force (gf) | Wet and Dry Bunched Compression Method: $5^{th}$ Cycle Wet Energy of Recovery (N*mm) |
|---|---|---|
| Comp. Ex. B | 129 | 0.59 |
| Comp. Ex. C | 86 | 0.32 |

It is found that absorbent core structures comprising nonwoven layer materials that have sufficient resiliency and recovery energy are able to recover to the original, pre-compression absorbent core structure shape. Ex. 1-3 exhibit a $5^{th}$ Cycle Wet Energy of Recovery of greater than 1.0 N*mm and a $5^{th}$ Cycle Wet Maximum Compression Force of from 207 gf to 213 gf. These structures exhibit a low force to compress (less resistance so it feels soft and flexible), yet are still able to recover their shape as the structure is compressed and released in a cyclic fashion. However, Comp. Ex. A-C exhibit a $5^{th}$ Cycle Wet Energy of Recovery of from 0.26 to 0.59 N*mm. Without sufficient recovery energy after five cycles of compression, Comp. Ex. A-C remain in a compressed, bunched state with insufficient force (stored energy) to recover its original, pre-compression shape.

Absorbent core structures and/or absorbent articles of the present disclosure can have a $5^{th}$ Cycle Wet Energy of Recovery of greater than about 1.0 N*mm, or from about 1.0 to about 3.5 N*mm. Absorbent core structures and/or absorbent articles of the present disclosure can have a $5^{th}$ Cycle Wet Maximum Compression Force of greater than about 150 gf, preferably greater than about 200 gf, or from about 150 gf to about 225 gf.

It is found that while an individual nonwoven material may have sufficient % Strain to Break in the Strain to Break Method, once combined into an absorbent core structure, the nonwoven material may not be capable of providing sufficient recovery energy for the full absorbent core structure (such as, for example in Comp. Ex. A) to return to its original, pre-compression shape. For instance, in Comp. Ex. A, the basis weight and thickness of the fibers of the upper nonwoven material when combined with the thin lower nonwoven material provides a $5^{th}$ Cycle Wet Energy of Recovery of less than 1.0 N*mm.

Finished Product Test

Absorbent articles are tested to assess the ability of a wrapped absorbent core structure to compress (simulating the compressions experienced between a wearer's legs) and to recover to their original state. Examples 4-7 illustrate absorbent articles described herein. Comp. Ex. D and E are comparative examples. Comp. Ex. F-L are in-market finished products. A description of Ex. 4-7 and Comp. Ex. D-E are listed in Table 5a. A description of Comp. Ex. F-L is listed in Tables 5b and 5c. Ex. 4-7 and Comp. Ex. D and E are prepared as described hereafter. The examples in Table 5a and 5b are evaluated according to the Wet and Dry CD and MD 3 Point Bend Method, the Wet and Dry Bunched Compression Method, and the Light Touch Rewet Method as described herein. The results are shown in in Table 6.

TABLE 5a

Absorbent Article Description

| Example | Topsheet | Absorbent core structure: Upper Nonwoven Layer | Absorbent core structure: Inner Core Layer | Absorbent core structure: Lower Nonwoven Layer |
|---|---|---|---|---|
| Ex. 4 | Nonwoven SG[13] | 40 gsm Carded Resilient Nonwoven[1] | 175 gsm Fluff[11]/ 70 gsm AGM[10] | 18 gsm Spunbond Nonwoven[6] |
| Ex. 5 | Nonwoven SG[13] | 55 gsm Resilient Spunlace 5[5] | 175 gsm Fluff[11]/ 70 gsm AGM[10] | 18 gsm Spunbond Nonwoven[6] |
| Ex. 6 | Nonwoven SG[13] | 50 gsm Resilient Spunlace 6[3] | 175 gsm Fluff[11]/ 70 gsm AGM[10] | 18 gsm Spunbond Nonwoven[6] |
| Ex. 7 | Nonwoven SG[13] | 55 gsm Resilient Spunlace 1[2] | 175 gsm Fluff[11]/ 70 gsm AGM[10] | 18 gsm Spunbond Nonwoven[6] |
| Comp. Ex. D | Nonwoven SG[13] | 24 gsm Carded Nonwoven[4] | 175 gsm Fluff[11]/ 70 gsm AGM[10] | 18 gsm Spunbond Nonwoven[6] |
| Comp. Ex. E | Nonwoven SG[13] | 17 gsm Tissue[8] | 175 gsm Fluff[11]/ 70 gsm AGM[10] | 17 gsm Tissue[8] |

[1]Available as ATB Z87G-40 from Xiamen Yanjan New Material Co. (China)

[2]Available as Sawasoft ® 53FC041001 from Sandler GmbH (Germany)

[3]Available as Sawasoft ® 553FC041005 (option 82) from Sandler GmbH (Germany)

[4]Available as Aura 20 from Xiamen Yanjan New Material Co. (China)

[5]Available as S25000541R01 from Jacob Holms Industries (Germany)

[6]Available as PFNZN 18G BICO8020 PHI 6 from dPFNonwovens Czech S.R.O (Czech Republic)

[8]Available as 3028 from DunnPaper (USA)

[10]Available as Favor SXM9745 from Evonik (Germany)

[11]Available as Item 9E3-COOSABSORB S from Resolute Alabama (USA)

[13]The nonwoven topsheet "Nonwoven SG" is a nonwoven web according to U.S. Patent Publication No. 2019/0380887.

TABLE 5b

| In-Market Finished Products: | | | |
|---|---|---|---|
| Example | In-Market Product | Size | Where Produced |
| Comp. Ex. F | Always Ultra | Size 2 | Canada |
| Comp. Ex. G | Stayfree Ultra | Size Long | USA |
| Comp. Ex. H | U by K (Kotex Security) | Size Long | USA |
| Comp. Ex. I | Body Form | Size Long | UK |
| Comp. Ex. J | Kao Laurier F | Size Long | Japan |
| Comp. Ex. K | Unicharm Sofy Naked Feel | Size regular | Japan |
| Comp. Ex. L | Always Infinity | Size 2 | Canada |

TABLE 5c

| Materials Found in the In-Market Products (Comp. Ex. F to L) | | | | |
|---|---|---|---|---|
| In-Market Products | Topsheet | First Acquisition Layer | Fluid Storage Layer | Other |
| Comp. Ex. F | Formed Film | 55 gsm Spunlace | 163 gsm Airlaid | n/a |
| Comp. Ex. G | Spunbond Nonwoven | Airlaid Secondary Topsheet | Fluff/AGM core densified | n/a |
| Comp. Ex. H | Spunbond Nonwoven | Airlaid Secondary Topsheet | Tissue wrapped Fluff/AGM core - densified | Additional cellulose oval element under topsheet |
| Comp. Ex. I | Spunbond Nonwoven | Airlaid Secondary Topsheet | Fluff/AGM core - densified | n/a |
| Comp. Ex. J | Carded Nonwoven | Carded Nonwoven | Tissue wrapped fluff/AGM core | n/a |
| Comp. Ex. K | Carded Nonwoven | Carded Nonwoven | Tissue wrapped fluff/AGM core | n/a |
| Comp. Ex. L | Spunbond Nonwoven | High Internal Phase Foam | High Internal Phase Foam | n/a |

Ex. 4 through 7 and Comp. Ex. D and E include structures as detailed for the Ex. 1 through 3 in Table 3 with the same adhesive designs and same 32 mm×16 mm structural bond pattern (a total structural bond site area of 1.38% of the total area of the absorbent core structure) in the absorbent core structure. Additionally, the absorbent articles include a nonwoven topsheet web as detailed in US Patent Publication No. 2019/0380887 bonded to the absorbent core structure with a spray adhesive application (Technomelt DM 9036U available from Henkel (Germany), 3 gsm continuous meltblown spirals, 50 mm wide, 150 mm long). In addition, a 12 gsm polypropylene backsheet is bonded to the outward-facing surface of the lower nonwoven with a spray adhesive application (Technomelt DM 9036U available from Henkel, (Germany), 3 gsm continuous meltblown spirals, 50 mm wide, 150 mm long).

Ex. 4-7 and Comp. Ex. D and E also have the structural bonds shown in FIG. 4 with the profile shown in FIG. 5. The structural bonds are applied with a heated aluminum die to create an emboss pattern within a heated hydraulic press. The structural bond embosser plate has protrusions of an area of 3.55 $mm^2$ and about 1 mm in height as shown in FIG. 4 with the profile shown in FIG. 5. The structural bonds are spaced according to the dimensions of separation described above. The structural bond embosser plate is heated to 120° C. and set to a compression pressure of 170 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the structural bond pattern.

Prior to bonding the backsheet, flex bond channel regions are applied to Ex. 4-7 and Comp. Ex. D and E with the pattern shown in FIG. 2C. The flex bond channel regions are applied with a heated aluminum die to create an emboss pattern within a heated hydraulic press. The flex bond channel embosser plate has protrusions spaced about 1.5 mm apart and are about 3 mm long and about 1.5 mm wide. The bond channel embosser plate is heated to 120° C. and set to a compression pressure of 200 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the emboss pattern.

TABLE 6

Absorbent Articles and In-Market Finished Products Tested in the Wet and Dry CD and MD 3 Point Bend Method, the Wet and Dry Bunched Compression Method, and the Light Touch Rewet Method

| | Wet & Dry CD & MD 3 Point Bend Method | | | Wet and Dry Bunched Compression Method | | Light Touch |
|---|---|---|---|---|---|---|
| Example | Dry Caliper (mm) | CD Dry Modulus (N/mm$^2$) | CD Dry Bending Stiffness (N · mm$^2$) | 5$^{th}$ Cycle Wet Energy of Recovery (N · mm) | 5$^{th}$ Cycle Wet % Recovery % | Rewet Method Light Touch Rewet (g) |
| Ex. 4 | 2.61 | 0.21 | 14.9 | 2.76 | 36 | 0.070 |
| Ex. 5 | 3.35 | 0.09 | 13.5 | 1.68 | 29 | 0.075 |
| Ex. 6 | 3.53 | 0.07 | 13.0 | 1.50 | 31 | 0.047 |
| Ex. 7 | 2.74 | 0.22 | 18.7 | 3.15 | 34 | 0.10 |
| Comp. Ex. D | 3.76 | 0.06 | 13.0 | 1.70 | 27 | 0.17 |
| Comp. Ex. E | 3.44 | 0.08 | 9.1 | 1.29 | 24 | 0.31 |
| Comp. Ex. F | 2.13 | 1.39 | 54.5 | 0.7 | 43 | n/a |
| Comp. Ex. G | 3.05 | 0.41 | 47.5 | 3.1 | 24 | n/a |
| Comp. Ex. H | 2.66 | 0.43 | 30.8 | 2.0 | 28 | n/a |
| Comp. Ex. I | 2.62 | 0.52 | 39.4 | 3.0 | 27 | n/a |
| Comp. Ex. J | 4.84 | 0.10 | 49.4 | 4.8 | 35 | n/a |
| Comp. Ex. K | 3.11 | 0.25 | 30.6 | 1.3 | 26 | n/a |
| Comp. Ex. L | 2.80 | 0.30 | 29 | 2.5 | 73 | n/a |

It is believed that in order to provide high bodily conformability, the absorbent article of the present disclosure can exhibit a low CD Dry Bending Stiffness (i.e., high flexibility) of from about 10 to about 30 N·mm$^2$, or from about 10 to about 25 N·mm$^2$. Also, it is believed that in order to provide an absorbent article that can compress with bodily motion and recover to its original, pre-compressed state against the user's body, the absorbent article of the present disclosure can have a 5$^{th}$ Cycle Wet Energy of Recovery of from about 1.0 to about 3.5 N·mm and/or a 5$^{th}$ Cycle Wet % Recovery of from about 29% to about 40%. Absorbent articles of the present disclosure can also maintain good fluid handling that delivers a low light touch rewet of from about 0 to about 0.15 g.

Ex. 4-7 exhibit a CD Dry Bending Stiffness of from 13.0 to 18.7 N·mm$^2$ and a 5$^{th}$ Cycle Wet % Recovery in the Wet and Dry Bunched Compression Method of from 29 to 36%, demonstrating that these structures will be able to sustain their shape in use. Comp. Ex. D and E exhibit a CD Dry Bending Stiffness of 9.1 and 13.0 N·mm$^2$, respectively. However, Comp. Ex. D and E exhibit a 5$^{th}$ Cycle Wet % Recovery in the Wet and Dry Bunched Compression Method that is less than 29%, demonstrating that these structures will be unable to sustain their shape in use and will remain bunched. Comp. Ex. F-L, which are in-market finished products, exhibit a CD Dry Bending Stiffness of 29 to 47.5 N·mm$^2$, demonstrating that the structures are less flexible and less able to conform.

Without being limited by theory, it is believed that in order to sustain a comfortable shape recovery after compression, sufficient recovery energy is needed to push the absorbent article on the panty back to its pre-compression shape. At the same time, the absorbent article (via the absorbent core structure) needs to recover along the same path as the compression to return to its pre-compression location. If the 5$^{th}$ Cycle Wet Energy of Recovery is less than about 1.0 N·mm the absorbent article may not have the recovery energy needed to recover its shape. If the 5$^{th}$ Cycle Wet Energy of Recovery value is too high, the recovery may be too forceful, leaving the wearer to feel like the absorbent article is not staying in place. If the 5$^{th}$ Cycle Wet % Recovery value is low (less than about 29%), the absorbent article may not return to its pre-compression shape and may remain deformed and bunched. If the 5$^{th}$ Cycle Wet % Recovery value is excessively high (greater than about 40%), it suggests that the absorbent article may recover too strongly to the flat shape when it is first applied to the wearer's panty as opposed to the shape against her body.

Structural Bond Test

Absorbent cores structures are tested to assess the impact of structural bond areas on flexibility and bending stiffness. Ex. 8 does not feature any structural bonds within the absorbent core structure. Ex. 9 and Ex. 10 have the structural bonds shown in FIG. 4 with the profile shown in FIG. 5. Ex. 8-10 are prepared as described hereafter. Results of the Wet and Dry MD 3 Point Bend Method are shown in Table 7.

TABLE 7

Absorbent Core Structures according to the invention with different Structural Bond Areas Tested in the Wet and Dry CD and MD 3 Point Bend Method.

| Example | Upper Nonwoven Layer | Inner Core Layer | Lower Nonwoven Layer | Structural Bond Spacing | MD Dry Bending Stiffness (N · mm$^2$) |
|---|---|---|---|---|---|
| Ex. 8 | 50 gsm Resilient Spunlace 6[3] | 175 gsm Fluff[11]/ 70 gsm AGM[10] | 10 gsm SMS Nonwoven[9] | Non-Structural Bonds | 9.8 |
| Ex. 9 | 50 gsm Resilient Spunlace 6[3] | 175 gsm Fluff[11]/ 70 gsm AGM[10] | 10 gsm SMS Nonwoven[9] | 32 mm × 16 mm | 19.2 |

TABLE 7-continued

Absorbent Core Structures according to the invention with different Structural Bond Areas Tested in the Wet and Dry CD and MD 3 Point Bend Method.

| Example | Upper Nonwoven Layer | Inner Core Layer | Lower Nonwoven Layer | Structural Bond Spacing | MD Dry Bending Stiffness (N · mm$^2$) |
|---|---|---|---|---|---|
| Ex. 10 | 50 gsm Resilient Spunlace 6[3] | 175 gsm Fluff[11]/ 70 gsm AGM[10] | 10 gsm SMS Nonwoven[9] | 16 mm × 16 mm | 29.6 |

[3]Available as Sawasoft ® 553FC041005 (option 82) from Sandler GmbH (Germany)
[9]Available as 10 SMS PHILIC from Union Industries SpA. (Italy)
[10]Available as Favor SXM9745 from Evonik (Germany)
[11]Available as Item 9E3-COOSABSORB S from Resolute Alabama (USA)

Figure 5:
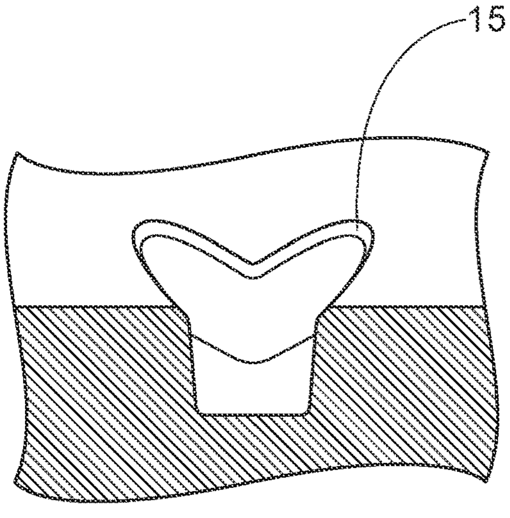
FIG. 5 is a cross section of the structural bond site of FIG. 4.

Table 7 demonstrates the impact of the total structural bond site area and spacing amount. The asymmetric structural bond shape as shown in FIG. 4 and the profile as shown in FIG. 5 has a maximum area of 3.55 mm$^2$. It is found that the MD Dry Bending Stiffness increases with the structural bond area. Ex. 8, which has non-structural bonds, exhibits an MD Dry Bending Stiffness of 9.8 N·mm$^2$. Ex. 9, which has a structural bond spacing of 32 mm×16 mm (a total structural bond site area of 1.38% of the total area of the absorbent core structure), exhibits an MD Dry Bending Stiffness of 19.2 N·mm$^2$. Ex. 10, which has a structural bond spacing of 16 mm×16 mm (a total structural bond site area of 3.96% of the total area of the absorbent core structure), exhibits an MD Dry Bending Stiffness of 29.6 N·mm$^2$. It is believed that in order to maintain a flexible and conformable absorbent core structure and/or an absorbent article in the front to back (MD) direction of wearing, the absorbent core structure and/or absorbent article can have an MD Dry Bending Stiffness of from about 10 to about 30 N·mm$^2$.

The absorbent core structures listed in Table 7 are produced as detailed within the specification. Specifically, the 50 gsm Resilient Spunlace 6 upper nonwoven is first introduced onto the forming drum within the laydown section, and under vacuum, it is drawn into the 3 dimensional pocket shape. A homogeneous stream of the fluff (cellulose) and AGM material is deposited onto the upper nonwoven material directly within the forming station. Prior to entering the forming station, the upper nonwoven is coated with a spray adhesive (Technomelt DM 9036U available from Henkel (Germany), 6 gsm continuous meltblown spirals, 50 mm wide) to provide a stronger connection of the fluff (cellulose) and AGM to the upper nonwoven layer without hindering the flow of liquid into the fluff/AGM mass. On exiting the laydown section, the 10 gsm SMS lower nonwoven web is combined with the nonwoven carrying the homogeneous blend of fluff (cellulose) and AGM layer. This lower nonwoven is precoated with adhesive (Technomelt DM 9036U available from Henkel (Germany)) to enable a perimeter seal (10 gsm meltblown spirals, 20 mm wide on the sides) and in the center a 6 gsm, 50 mm wide continuous meltblown spiral adhesive is applied to better integrate the fluff/AGM mass. Structural bonds as shown in FIG. 4 with the profile shown in FIG. 5 are applied to Ex. 9 and 10. The structural bonds of Ex. 9 have a spacing of 32 mm×16 mm, thereby occupying a total structural bond site area of 1.38% of the total area of the absorbent core structure. The structural bonds of Ex. 10 have a spacing of 16 mm×16 mm, thereby occupying a total structural bond site area of 3.96% of the total area of the absorbent core structure with this structural bond profile. The total area of the absorbent core structure is measured according to the Structural Bond Sites Pattern Spacing and Area Measurement Method. The structural bonds are applied with the same method as described above for Ex. 1-3 and Comp. Ex. A-B.

Fluid Management Test

Nonwoven materials are tested to assess the ability of the material to effectively manage fluid. Samples F, H, and I are comparative examples. A description of the samples is listed in Table 1 above. The materials are evaluated according to the Thickness-Pressure Method, Permeability Measurement Method, Pore Volume Distribution Method, and Wet Penetration Time Method. Density is determined by dividing the basis weight of the material by the thickness. The results are shown in Table 8.

TABLE 8

Nonwoven Materials Tested in the Thickness - Pressures Method, Permeability Measurement Method, Pore Volume Distribution (PVD) Method, and Wet Penetration Time Method

| | | Thickness - Pressure Method | | Permeability Measurement | PVD Method Capillary Work | Wet Penetration Time Method Wet |
|---|---|---|---|---|---|---|
| Sample | Density at 7 g/cm$^2$ g/cm$^3$ | Thickness at 7 g/cm$^2$ mm | Thickness at 70 g/cm$^2$ mm | Method Permeability Darcy | Potential (CWP) mJ/m2 | Penetration Time seconds |
| A | 0.03 | 1.21 | 0.26 | 987 | 230 | 0.17 |
| B | 0.06 | 0.99 | 0.44 | 387 | 265 | 0.95 |
| C | 0.07 | 0.76 | 0.62 | 297 | 362 | 1.54 |
| E | 0.07 | 0.80 | 0.40 | 317 | 347 | 2.05 |
| F | 0.09 | 0.21 | 0.17 | 146 | 180 | 4.11 |
| H | 0.12 | 0.14 | 0.11 | 103 | 120 | 4.20 |
| I | 0.10 | 0.10 | 0.09 | 1.9 | 12 | >10 |

Samples A, B, C, and E exhibit a relatively low density of from 0.03 to 0.07 g/cm$^3$ under a pressure of 7 g/cm$^2$ and a Thickness at 7 g/cm2 of pressure of from 0.80 to 1.21 mm, demonstrating that these materials are both lofty and have a more open fiber network structure. Samples F, H, and I, which are comparative examples, exhibit a higher density of from 0.09 to 0.12 g/cm$^3$ under a pressure of 7 g/cm$^2$ and a significantly lower Thickness at 7 g/cm2 of pressure of from 0.10 to 0.21 mm. Without being limited by theory, it is believed that when nonwoven materials with a low density (i.e., less than 0.09 g/cm3) are used as an upper nonwoven layer in the absorbent core structure disclosed herein, the inner core layer fluff/AGM matrix are better able to drain the upper nonwoven layer of fluid.

Samples A, B, C, and E are also still able to maintain a relatively lofty thickness even under high bodily compressive forces (corresponding to a pressure of 70 g/cm$^2$), demonstrating that these materials will still be able to be effectively drained of fluid by the fluff/AGM matrix. In contrast, Samples F, H, and I exhibit a Thickness at 70 g/cm2 of pressure of from 0.09 to 0.17 mm, demonstrating that these materials become even more densified, and as such exhibit even higher capillarity, and would be insufficient as an upper nonwoven layer because fluid draining into the fluff/AGM matrix would be restricted due to the material having a higher capillarity than the fluff/AGM matrix below.

Finally, it is found that Samples F, H, and I have a Wet Penetration Time of greater than 4 seconds, demonstrating that fluid does not penetrate straight through the material but instead spreads on top of the material. In contrast, Samples A, B, C, and E have a Wet Penetration Time of less than about 4 seconds, demonstrating that fluid will be able to move more rapidly through the material and into the fluff/AGM matrix more efficiently versus spreading on the surface as seen in Samples F, H, and I. Upper nonwoven layers of the present disclosure can have a Wet Penetration Time of less than about 4 seconds, preferably less than about 3 seconds.

Consumers may prefer absorbent articles that can conform to the body and can deliver a dry wearing experience. In separate experiments, absorbent articles are prepared to further assess the ability of the absorbent articles to compress and recover to their original state and the ability to effectively drain fluid. Ex. 11-14 illustrate absorbent articles as described herein. Comp. Ex. M-O are in-market finished products. A description of Ex. 11-14 and Comp. Ex. M-O are listed in Tables 9a and 9b. Ex. 11-14 are prepared as described hereafter. Ex. 11-14 are tested at different times than Ex. 15-17 and Comp. Ex. M-O; however, the data are shown together for ease of comparison. Ex. 11-14 and Comp. Ex. M-O are evaluated according to the Wet and Dry CD and MD 3 Point Bend Method and the Wet and Dry Bunched Compression Method, with the results shown in Table 10, and the Acquisition Time and Rewet Method and Light Touch Rewet Method, with the results shown in Table 11.

TABLE 9a

| Absorbent Article Description | | | | |
|---|---|---|---|---|
| | | Absorbent core structure | | |
| Example | Topsheet | Upper Nonwoven Layer | Inner Core Layer | Lower Nonwoven Layer |
| Ex. 11 | Nonwoven SG[13] | 55 gsm Resilient Spunlace 5[5] | 175 gsm Fluff[11]/ 70 gsm AGM[10] | 18 gsm Spunbond Nonwoven[6] |
| Ex. 12 | Nonwoven SG[13] | 55 gsm Resilient Spunlace 5[5] | 150 gsm Fluff[11] 60 gsm AGM[10] | 18 gsm Spunbond Nonwoven[6] |
| Ex. 13 | Nonwoven SG[13] | 55 gsm Resilient Spunlace 5[5] | 150 gsm Fluff[11]/ 60 gsm AGM[10] | 18 gsm Spunbond Nonwoven[6] |
| Ex. 14 | Carded Nonwoven[14] | 40 gsm Carded Resilient Nonwoven[1] | 150 gsm Fluff[11]/ 60 gsm AGM[10] | 40 gsm Carded Resilient Nonwoven[1] |
| Ex. 15 | Carded Nonwoven[14] | 40 gsm Carded Resilient Nonwoven[1] | 150 gsm Fluff[11]/ 60 gsm AGM[10] | 18 gsm Spunbond Nonwoven[6] |
| Ex. 16 | Carded Nonwoven[14] | 40 gsm Carded Resilient Nonwoven[1] | 150 gsm Fluff[11]/ 40 gsm AGM[10] | 18 gsm Spunbond Nonwoven[6] |
| Ex. 17 | Carded Nonwoven[14] + 99% Caprylic/Capric Triglyceride[15] & 1% PPG - 15 stearyl ether[16] | 40 gsm Carded Resilient Nonwoven[1] | 150 gsm Fluff[11]/ 60 gsm AGM[10] | 18 gsm Spunbond Nonwoven[6] |

[1]Available as ATB Z87G-40 from Xiamen Yanjan New Material Co. (China)
[5]Available as S25000541R01 from Jacob Holms Industries (Germany)
[6]Available as PFNZN 18G BICO8020 PHI 6 from dPFNonwovens Czech S.R.O (Czech Republic)
[10]Available as Favor SXM9745 from Evonik (Germany)
[11]Available as Item 9E3-COOSABSORB S from Resolute Alabama (USA)
[13]The nonwoven topsheet "Nonwoven SG" is a nonwoven web according to U.S. Patent Publication No. 2019/0380887
[14]Available as Z73P from Xiamen Yanjan New Material Co. (China)
[15]Available as MYRITOL 318 from BASF Corporation (USA)
[16]Available as CETIOL E, from BASF Corporation (USA)

TABLE 9b

| In-Market Finished Products | | | | | | |
|---|---|---|---|---|---|---|
| Example | In-Market Product | Size | Where Produced | Topsheet | First Acquisition Layer | Fluid Storage Layer |
| Comp. Ex. M | Always Ultra | Size 2 | Canada | Formed Film | 55 gsm Spunlace | 163 gsm Airlaid |
| Comp. Ex. N | Body Form | Size Long | UK | Spunbond Nonwoven | Airlaid Secondary Topsheet | Fluff/AGM core - densified |
| Comp. Ex. O | Kao Laurier F | Size Long | Japan | Carded Nonwoven | Carded Nonwoven | Tissue wrapped fluff/AGM core |

Absorbent articles Ex. 11-17 are produced as detailed within the specification. Specifically, the upper nonwoven is first introduced onto the forming drum within the laydown section and under vacuum it is drawn into the 3 dimensional pocket shape. A homogeneous stream of the fluff (cellulose) and AGM material is deposited onto the upper nonwoven material directly within the forming station. Prior to entering the forming station the upper nonwoven is coated with a spray adhesive (Technomelt DM 9036U available from Henkel (Germany), 6 gsm continuous meltblown spirals, 50 mm wide) to provide a stronger connection of the fluff (cellulose) and AGM to the upper nonwoven layer without hindering the flow of liquid into the cellulose/AGM mass. On exiting the laydown section, the lower nonwoven web is combined with the nonwoven carrying the homogeneous blend of fluff (cellulose) and AGM layer. This lower nonwoven is precoated with adhesive (Technomelt DM 9036U available from Henkel (Germany)) to enable a perimeter seal (10 gsm meltblown spirals, 20 mm wide on the sides) and in the center a 6 gsm, 50 mm continuous meltblown spiral adhesive (Technomelt DM 9036U available from Henkel (Germany)) is applied to better integrate the fluff/AGM mass. Additionally, the absorbent articles include a nonwoven topsheet web is bonded to the absorbent core structure with a spray adhesive application (Technomelt DM 9036U available from Henkel (Germany), 3 gsm continuous meltblown spirals, 50 mm wide, 150 mm long). In addition, a 12 gsm polypropylene film backsheet is bonded to the bottom surface of the lower nonwoven (garment-facing surface) with a spray adhesive application (Technomelt DM 9036U available from Henkel (Germany), 3 gsm continuous meltblown spirals, 50 mm wide, 150 mm long). Ex. 11-17 also have the structural bonds shown in FIG. 4 with the profile shown in FIG. 5 and are applied with a spacings of 32 mm×16 mm, thereby occupying a total structural bond site area of 1.38% of the total area of the absorbent core structure. The structural bonds are applied using the method described above for Ex. 1-3 and Comp. Ex. A-B. Prior to bonding the backsheet, flex bond channels are applied to Ex. 11-13 with the pattern shown in FIG. 2C. The flex bond channels are applied with a heated aluminum die to create an emboss pattern within a heated hydraulic press. The flex bond channel embosser plate has protrusions spaced about 1.5 mm apart and are about 3 mm long and about 1.5 mm wide. The bond channel embosser plate is heated to 120° C. and set to a compression pressure of 200 kPa. The absorbent article is placed and orientated underneath the heated embosser plate on the hydraulic press bottom plate and a sheet of thin Teflon™ film is placed over the sample prior to embossing to avoid melting of the topsheet fibers. The hydraulic press is activated and compresses the sample for a dwell time of 1.7 seconds to create the emboss pattern.

TABLE 10

| Absorbent Articles Tested in the Wet and Dry CD and MD 3 Point Bend Method and the | | | | | |
|---|---|---|---|---|---|
| | Wet & Dry CD & MD 3-Point Bend Method | | | Wet and Dry Bunched Compression Method | |
| Example | Dry Caliper (mm) | CD Dry Modulus (N/mm$^2$) | CD Dry Bending Stiffness (N · mm$^2$) | 5$^{th}$ Cycle Wet Energy of Recovery (N · mm) | 5$^{th}$ Cycle Wet % Recovery (%) |
| Ex. 11 | 2.80 | 0.12 | 21.0 | 3.10 | 34% |
| Ex. 12 | 2.90 | 0.11 | 10.4 | 1.27 | 31% |
| Ex. 13 | 2.80 | 0.13 | 11.9 | 1.64 | 33% |
| Ex. 14 | 2.89 | 0.16 | 15.8 | 1.73 | 34% |
| Ex. 15 | 2.46 | 0.22 | 13.73 | 1.71 | 32% |
| Ex. 16 | 2.52 | 0.25 | 16.62 | 1.47 | 31% |
| Ex. 17 | 2.36 | 0.26 | 14.68 | 1.44 | 32% |
| Comp. Ex. M | 2.08 | 1.17 | 54.5 | 0.71 | 43% |
| Comp. Ex. N | 2.60 | 0.69 | 49.2 | 2.50 | 29% |
| Comp. Ex. O | 4.80 | 0.11 | 50.8 | 3.80 | 31% |

TABLE 11

Absorbent Articles Tested in the Acquisition Time and Rewet Method and the Light Touch Rewet Method

| Example | Acquisition Time and Rewet Method Total Gush Absorbency Time (seconds) | Surface Free Fluid (SFF) (mg) | Interfacial Free Fluid (IFF) (mg) | Total IFF + SFF (mg) | Light Touch Rewet Method Light Touch Rewet (g) |
|---|---|---|---|---|---|
| Ex. 11 | 23.0 | 83.2 | 12.8 | 96.0 | 0.060 |
| Ex. 12 | 19.8 | 105.8 | 12.7 | 118.5 | 0.080 |
| Ex. 13 | 23.3 | 34.6 | 15.8 | 50.4 | 0.030 |
| Ex. 14 | 18.5 | 93.3 | 24.1 | 117.4 | 0.010 |
| Ex. 15 | 25.3 | 162.6 | 26.1 | 188.7 | 0.012 |
| Ex. 16 | 17.4 | 111.5 | 40.5 | 151.9 | 0.020 |
| Ex. 17 | 15.8 | 15.6 | 25.6 | 41.2 | 0.009 |
| Comp. Ex. M | 8.0 | 54.0 | 73.1 | 127.1 | 0.017 |
| Comp. Ex. N | 30.4 | 126.7 | 17.8 | 144.5 | 0.022 |
| Comp. Ex. O | 24.9 | 39.9 | 22.7 | 62.6 | 0.120 |

It is surprisingly found that flexible and/or resilient absorbent core structures and/or absorbent articles can efficiently manage fluid as it exits the body without the need for typical densification/stiffening. Ex. 11-17 have comparable Total IFF+SFF and Light Touch Rewet values as Comp. Ex. M-O which have a significantly higher CD Dry Bending Stiffness as a result of densification (Table 10).

Figure 18:
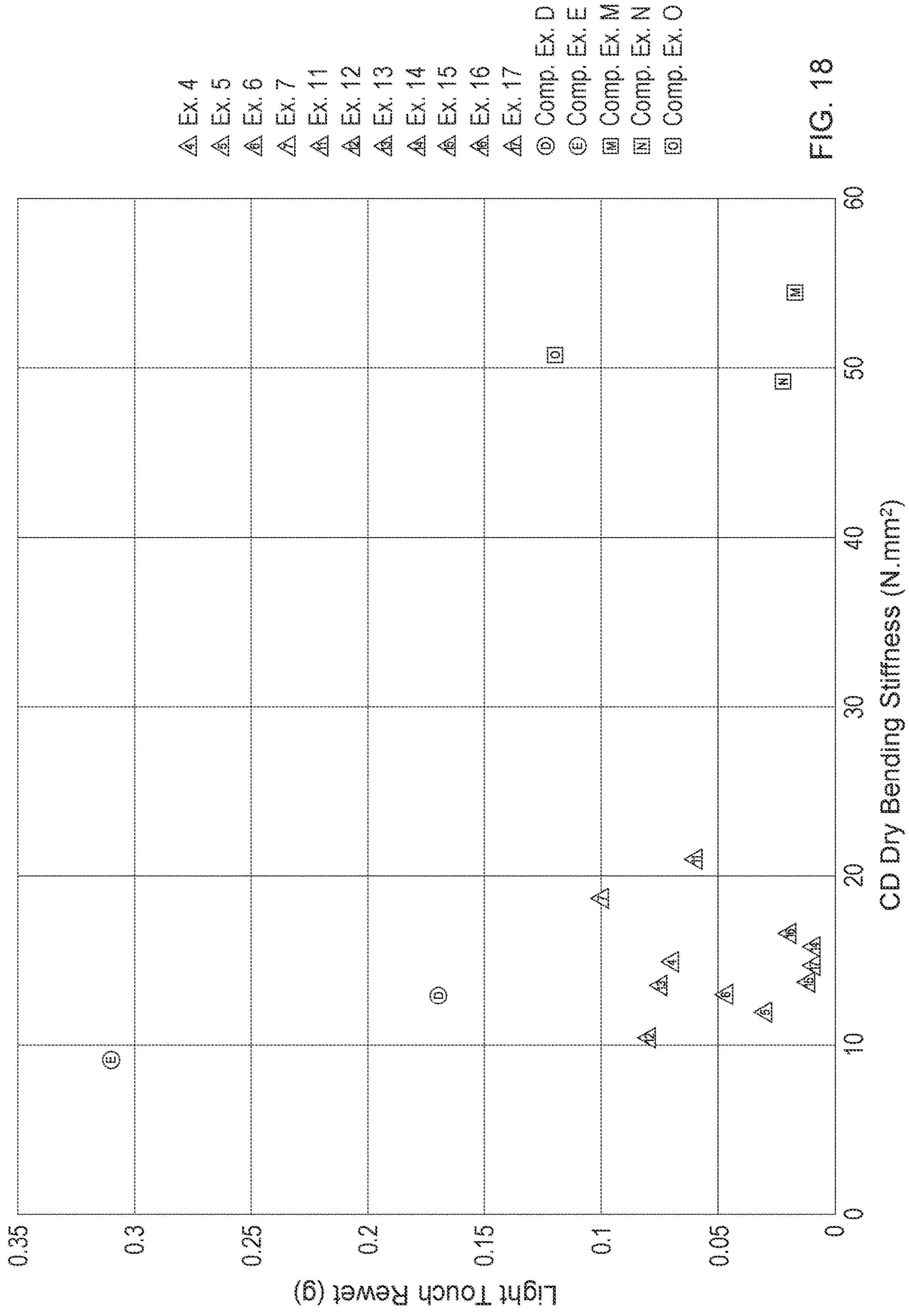
FIG. 18 is a graph depicting Light Touch Rewet in grams (g) versus the CD Dry Bending Stiffness in N·mm2 of a plurality of measured samples.

The Light Touch Rewet in grams (g) is shown versus the CD Dry Bending Stiffness in N·mm$^2$ in the graph shown in FIG. 18. In some aspects, the absorbent article can have a Light Touch Rewet value of from about 0 g to about 0.15 g as measured according to the Light Touch Rewet Method and a CD Dry Bending Stiffness of from about 10 N·mm$^2$ to about 30 N·mm$^2$ as measured according to the Wet & Dry CD & MD 3 Point Bend Method.

Figure 19:
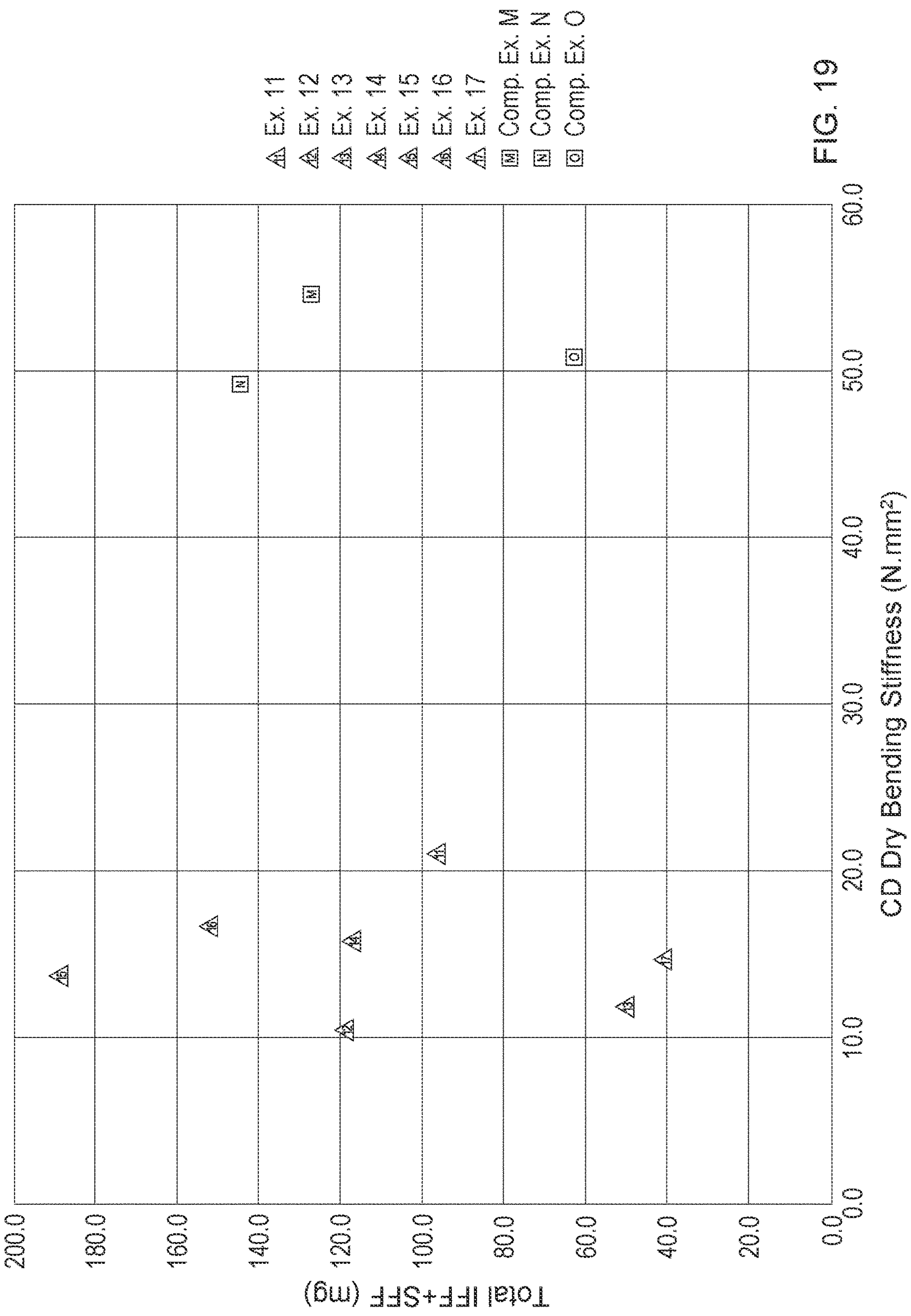
FIG. 19 is a graph depicting Total IFF+SFF in milligrams (mg) versus CD Dry Bending Stiffness in N·mm2 of a plurality of measured samples.

The Total IFF+SFF in milligrams (mg) is shown versus CD Dry Bending Stiffness in N·mm$^2$ in the graph shown in FIG. 19. In some aspects, the absorbent article can have a CD Dry Bending Stiffness of from about 10 N·mm$^2$ to about 30 N·mm$^2$ as measured according to the Wet & Dry CD & MD 3 Point Bend Method and a Total IFF+SFF of from about 20 mg to about 200 mg as measured according to the Acquisition Time and Rewet Method.

Combinations/Examples

Paragraph A. A disposable absorbent article comprising:

a topsheet;

a backsheet; and an absorbent core structure disposed between the topsheet and backsheet, wherein the absorbent core structure comprises:

(a) an upper nonwoven layer comprising polymer fibers;

(b) a lower nonwoven layer comprising polymer fibers; and (c) an inner core layer disposed between the upper nonwoven layer and the lower nonwoven layer, wherein the inner core layer comprises from about 50% to about 85% cellulosic fibers, by weight of the inner core layer, and superabsorbent particles;

wherein the inner core layer is contained within the nonwoven layers by substantially sealing at least a left side region and a right side region of the upper nonwoven layer and the lower nonwoven layer at a perimeter seal;

wherein the absorbent article has a CD Dry Bending Stiffness between about 10 N·mm$^2$ to about 30 N·mm$^2$ as measured according to the Wet and Dry CD and MD 3 Point Bend Method and a Total IFF+SFF value of between about 20 mg and about 200 mg as measuring according to the Acquisition Time and Rewet Method.

Paragraph B. The disposable absorbent article of Paragraph A, wherein the absorbent article has a 5$^{th}$ Cycle Wet % Recovery of between about 29% and about 40% as measured according to the Wet and Dry Bunched Compression Method.

Paragraph C. The disposable absorbent article of Paragraph A or B, wherein at least one of the upper nonwoven layer and the lower nonwoven layer is an air through bonded nonwoven or a hydroentangled nonwoven.

Paragraph D. The disposable absorbent article of any of Paragraphs A-C, wherein the polymer fibers of the upper nonwoven layer have a fiber length of from 10 mm to 100 mm, preferably from 20 mm to 50 mm.

Paragraph E. The disposable absorbent article of any of Paragraphs A-D, wherein the polymer fibers of the upper nonwoven layer have a fiber diameter of from 2.0 DTex to 10 DTex and the polymer fibers of the lower nonwoven layer have a fiber diameter of from 1.7 DTex to 5 DTex.

Paragraph F. The disposable absorbent article of any of Paragraphs A-E, wherein the topsheet is in direct contact with the upper nonwoven layer, and the upper nonwoven layer is in direct contact with the inner core layer.

Paragraph G. The disposable absorbent article of any of Paragraphs A-F, wherein the absorbent article has a Dry Caliper of from about 2.0 mm to about 6.0 mm as measured according to the Wet and Dry CD and MD 3-Point Method.

Paragraph H. The disposable absorbent article of any of Paragraphs A-G, wherein the absorbent article has an average density of between about 0.045 g/cm3 and about 0.16 g/cm3.

Paragraph I. The disposable absorbent article of any of Paragraphs A-H, wherein the upper nonwoven layer fibers comprise from about 70 to about 100% synthetic fibers, and from about 0 to about 40% regenerated cellulosic fibers comprising rayon.

Paragraph J. The disposable absorbent article of any of Paragraphs A-I, wherein at least a portion of the topsheet comprises an anti-stick agent.

Paragraph K. A disposable absorbent article comprising:
- a topsheet;
- a backsheet; and
- an absorbent core structure disposed between the topsheet and backsheet, wherein the absorbent core structure comprises:
  - (a) an upper nonwoven layer comprising polymer fibers, wherein the upper nonwoven layer has a Thickness at 7 g/cm2 pressure of from about 0.3 mm to about 1.3 mm as measured according to the Thickness-Pressure Method;
  - (b) a lower nonwoven layer comprising polymer fibers, wherein the lower nonwoven layer has a Thickness at 7 g/cm2 pressure of from about 0.1 mm to about 1.3 mm as measured according to the Thickness-Pressure Method and a basis weight equal to or less than a basis weight of the resilient upper nonwoven layer; and
  - (c) an inner core layer disposed between the upper nonwoven layer and the lower nonwoven layer;
- wherein the inner core layer comprises from about 125 gsm to about 400 gsm cellulosic fibers;
- wherein the absorbent core structure has an average density of between about 0.045 g/cm3 and about 0.15 g/cm3; and
- wherein the upper nonwoven layer has a Wet Penetration Time of less than about 4 seconds as measured according to the Wet Penetration Time Method.

Paragraph L. The disposable absorbent article of Paragraph K, wherein the inner core layer comprises from about 20 gsm to about 100 gsm superabsorbent particles.

Paragraph M. The disposable absorbent article of Paragraph K or L, wherein the upper nonwoven layer has a Thickness at 70 g/cm2 pressure of from about 0.2 mm to about 0.7 mm as measured according to the Thickness-Pressure Method.

Paragraph N. The disposable absorbent article of any one Paragraphs K-M, wherein the upper nonwoven layer has a permeability of from about 150 Darcy to about 1000 Darcy as measured according to the Permeability Measurement Method.

Paragraph O. The disposable absorbent article of any one Paragraphs K-N, wherein the upper nonwoven layer has a Capillary Work Potential of from about 200 mJ/m2 to about 400 mJ/m2 as measured according to the Pore Volume Distribution Method.

Paragraph P. The disposable absorbent article of any one Paragraphs K-O, wherein the upper nonwoven polymer fibers have a fiber diameter of from about 2.0 DTex to about 10 DTex, and the lower nonwoven polymer fibers have a fiber diameter of from about 1.7 DTex to about 5 DTex.

Paragraph Q. The disposable absorbent article of any one Paragraphs K-P, wherein the polymer fibers of the upper nonwoven layer are selected from polyethylene terephthalate, polypropylene, polylactic acid, bicomponent fiber comprising polyethylene/polypropylene or polyethylene/polyethylene terephthalate, and combinations thereof.

Paragraph R. The disposable absorbent article of any one Paragraphs K-Q, wherein the polymer fibers of the lower nonwoven layer are selected from polyethylene terephthalate, polypropylene, polylactic acid, bicomponent fiber comprising polyethylene/polypropylene or polyethylene/polyethylene terephthalate, and combinations thereof.

Paragraph S. The disposable absorbent article of any one Paragraphs K-R, wherein the polymer fibers of the upper nonwoven layer have a fiber length of from about 10 mm to about 100 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
- a topsheet;
- a backsheet; and
- an absorbent core structure disposed between the topsheet and the backsheet, wherein the absorbent core structure comprises:
- a. an upper nonwoven layer comprising polymer fibers, wherein the polymer fibers comprise a sheath-core configuration, wherein a sheath of the sheath-core configuration comprises a lower melting temperature than a core component of the sheath-core configuration, and wherein the polymer fibers comprise inter-fiber bonds, the polymer fibers comprising a thickness of from greater than about 2.0 DTex to about 10.0 DTex, wherein the polymer fibers comprise crimped fibers, wherein the crimped fibers comprise an average crimp count of 4 to 12 crimps per inch; wherein the upper nonwoven layer has a density at 7 g/cm$^2$ of less than about 0.09 g/cm$^3$ and a thickness at 7 g/cm$^2$ of at least 0.80 mm;
- b. a lower nonwoven layer comprising polymer fibers, the polymer fibers comprising a thickness of from about 1.7 DTex to about 5.0 DTex; and
- c. an inner core layer disposed between the upper nonwoven layer and the lower nonwoven layer, wherein the inner core layer comprises from about 50% to about 85% cellulosic fibers, by weight of the inner core layer, and superabsorbent particles;

wherein the inner core layer is contained within the nonwoven layers by substantially sealing at least a left side region and a right side region of the upper nonwoven layer and the lower nonwoven layer at a perimeter seal;

wherein a middle region disposed intermediate a front region and a back region of the absorbent core structure is substantially free of structural bond sites, and wherein the middle region is at least partially surrounded by structural bond sites and/or embossing in the front region and back region;

wherein the absorbent article has a CD Dry Bending Stiffness between about 10 N·mm$^2$ to about 30 N·mm$^2$ as measured according to the Wet and Dry CD and MD 3 Point Bend Method and a Total IFF+SFF value of between about 20 mg and about 200 mg as measured according to the Acquisition Time and Rewet Method.

2. The disposable absorbent article of claim 1, wherein the absorbent article has a 5$^{th}$ Cycle Wet % Recovery of between about 29% and about 40% as measured according to the Wet and Dry Bunched Compression Method.

3. The disposable absorbent article of claim 1, wherein the upper nonwoven layer is an air through bonded nonwoven or a hydroentangled nonwoven.

4. The disposable absorbent article of claim 3, wherein the lower nonwoven layer is an air through bonded nonwoven or a hydroentangled nonwoven.

5. The disposable absorbent article of claim 1, wherein the topsheet is in direct contact with the upper nonwoven layer, and the upper nonwoven layer is in direct contact with the inner core layer.

6. The disposable absorbent article of claim 1, wherein the absorbent article has a Dry Caliper of from about 2.0 mm to about 6.0 mm as measured according to the Wet and Dry CD and MD 3-Point Method.

7. The disposable absorbent article of claim 1, wherein the absorbent article has an average density of between about 0.045 g/cm$^3$ and about 0.15 g/cm$^3$.

8. The disposable absorbent article of claim 1, wherein the polymer fibers of the upper nonwoven layer comprise from about 70 to about 100% synthetic fibers, and from about 0 to about 40% regenerated cellulosic fibers comprising rayon.

9. A disposable absorbent article comprising:

a topsheet;

a backsheet; and an absorbent core structure disposed between the topsheet and the backsheet, wherein the absorbent core structure comprises:

a. an upper nonwoven layer comprising polymer fibers, wherein the polymer fibers comprise crimped fibers, wherein the crimped fibers comprise an average crimp count of 4 to 12 crimps per inch; wherein the upper nonwoven layer has a density at 7 g/cm$^2$ of less than about 0.09 g/cm$^3$ and a thickness at 7 g/cm$^2$ of at least 0.80 mm, and having a basis weight of from about 35 gsm to about 85 gsm;

b. a lower nonwoven layer comprising polymer fibers and having a basis weight of from about 10 gsm to about 40 gsm, wherein the polymer fibers comprise crimped fibers, wherein the crimped fibers comprise an average crimp count of 4 to 12 crimps per inch; and c. an inner core layer disposed between the upper nonwoven layer and the lower nonwoven layer, wherein the inner core layer comprises a mixture of cellulosic fibers and superabsorbent particles;

wherein the inner core layer is contained within the nonwoven layers by substantially sealing at least a left side region and a right side region of the upper nonwoven layer and the lower nonwoven layer at a perimeter seal, wherein the perimeter seal comprises a seal width of from about 1 mm to about 10 mm;

wherein a middle region disposed intermediate a front region and a back region of the absorbent core structure is substantially free of structural bond sites, and wherein the middle region is at least partially surrounded by structural bond sites and/or embossing in the front region and back region;

wherein the polymer fibers of the upper nonwoven layer have a fiber thickness of from about 2.0 DTex to about 10 DTex, and the polymer fibers of the lower nonwoven layer have a fiber thickness of from about 1.7 DTex to about 5 DTex; and wherein the absorbent article has a CD Dry Bending Stiffness between about 10 N·mm$^2$ to about 30 N·mm$^2$ as measured according to the Wet and Dry CD and MD 3 Point Bend Method and a Light Touch Rewet of from 0 to about 0.15 grams as measured according to the Light Touch Rewet Method.

10. The disposable absorbent article of claim 9, wherein the inner core layer comprises from about 50% to about 85% cellulosic fibers, by weight of the inner core layer, and from about 15% to about 50% superabsorbent particles, by weight of the inner core layer.

11. The disposable absorbent article of claim 9, wherein the upper nonwoven layer has a Thickness at 7 g/cm$^2$ pressure of from about 0.3 mm to about 1.3 mm as measured according to the Thickness-Pressure Method.

12. The disposable absorbent article of claim 9, wherein the upper nonwoven layer has a Thickness at 70 g/cm$^2$ pressure of from about 0.2 mm to about 0.7 mm as measured according to the Thickness-Pressure Method.

13. The disposable absorbent article of claim 9, wherein the absorbent article has a 5$^{th}$ Cycle Wet % Recovery of between about 29% and about 40% as measured according to the Wet and Dry Bunched Compression Method.

14. The disposable absorbent article of claim 9, wherein at least a portion of the topsheet comprises an anti-stick agent.

15. A disposable absorbent article comprising:

a topsheet;

a backsheet; and an absorbent core structure disposed between the topsheet and the backsheet, wherein the absorbent core structure comprises:

a. an upper nonwoven layer comprising polymer fibers, the polymer fibers comprising a thickness of from greater than about 2.0 DTex to about 10.0 DTex, wherein the upper nonwoven layer has a Thickness at 7 g/cm$^2$ pressure of from about 0.3 mm to about 1.3 mm as measured according to the Thickness-Pressure Method, wherein the polymer fibers comprise crimped fibers, wherein the crimped fibers comprise an average crimp count of 4 to 12 crimps per inch;

b. a lower nonwoven layer comprising polymer fibers, the polymer fibers comprising a thickness of from about 1.7 DTex to about 5.0 DTex, wherein the lower nonwoven layer has a Thickness at 7 g/cm$^2$ pressure of from about 0.1 mm to about 1.3 mm as measured according to the Thickness-Pressure Method and a basis weight equal to or less than a basis weight of the upper nonwoven layer; and c. an inner core layer disposed between the upper nonwoven layer and the lower nonwoven layer;

wherein the inner core layer comprises from about 125 gsm to about 400 gsm cellulosic fibers;

wherein the upper nonwoven layer has a density at 7 $g/cm^2$ of less than about 0.09 $g/cm^3$ and a thickness at 7 $g/cm^2$ of at least 0.80 mm;

wherein the absorbent core structure has an average density of between about 0.045 $g/cm^3$ and about 0.15g/$cm^3$; and wherein the upper nonwoven layer has a Wet Penetration Time of less than about 4 seconds as measured according to the Wet Penetration Time Method.

16. The disposable absorbent article of claim 15, wherein the inner core layer comprises from about 20 gsm to about 100 gsm superabsorbent particles.

17. The disposable absorbent article of claim 15, wherein the upper nonwoven layer has a permeability of from about 150 Darcy to about 1000 Darcy as measured according to the Permeability Measurement Method.

18. The disposable absorbent article of claim 15, wherein the upper nonwoven layer has a Capillary Work Potential of from about 200 $mJ/m^2$ to about 400 $mJ/m^2$ as measured according to the Pore Volume Distribution Method.

19. The disposable absorbent article of claim 1, wherein the upper nonwoven layer comprises a Permanent Strain of about 0.005 mm/mm to about 0.013 mm/mm.

20. The disposable absorbent article of claim 1, wherein the polymer fibers in the upper nonwoven layer and the polymer fibers of the lower nonwoven layer are different.

* * * * *